US006436966B1

(12) United States Patent
Ohkawa et al.

(10) Patent No.: US 6,436,966 B1
(45) Date of Patent: Aug. 20, 2002

(54) ADENOSINE $A_3$ RECEPTOR ANTAGONISTS

(75) Inventors: Shigenori Ohkawa, Takatsuki; Hiroyuki Kimura, Sakai; Naoyuki Kanzaki, Ibaraki, all of (JP)

(73) Assignee: Takeda Chemical Ind., Ltd., Osaka (JP)

( * ) Notice: Subject to any disclaimer, the term of this patent is extended or adjusted under 35 U.S.C. 154(b) by 0 days.

(21) Appl. No.: 09/463,639

(22) PCT Filed: Oct. 26, 1998

(86) PCT No.: PCT/JP98/04837

§ 371 (c)(1),
(2), (4) Date: Jan. 27, 2000

(87) PCT Pub. No.: WO99/21555

PCT Pub. Date: May 6, 1999

(30) Foreign Application Priority Data

Oct. 27, 1997 (JP) .............................................. 9-294485

(51) Int. Cl.[7] ................................................ A01N 43/40

(52) U.S. Cl. ........................ 514/340; 514/341; 514/342; 546/270.4; 546/271.4; 546/274.4

(58) Field of Search ........................... 546/270.4, 271.4, 546/274.1; 514/340, 341, 342

(56) References Cited

U.S. PATENT DOCUMENTS 4,199,592 A * 4/1980 Cherkofsky
4,238,496 A * 12/1980 Hess
4,251,535 A * 2/1981 Cherkofsky
5,296,495 A * 3/1994 Matsuo
5,486,526 A * 1/1996 Durant
5,620,999 A * 4/1997 Weier
5,633,382 A * 5/1997 Durant
5,717,100 A * 2/1998 Selnick
5,739,143 A * 4/1998 Adams
5,756,499 A * 5/1998 Adams
5,891,892 A * 4/1999 Cheng
5,958,950 A * 9/1999 Padia
5,965,583 A * 10/1999 Beers
5,969,184 A * 10/1999 Adams
5,972,980 A * 10/1999 Cornicelli
5,977,103 A * 11/1999 Adams
6,001,866 A * 12/1999 Cornicelli
6,040,320 A * 3/2000 Beers
6,069,162 A * 5/2000 Itoh
6,080,764 A * 6/2000 Chihiro
6,083,949 A * 7/2000 Liverton
6,096,739 A * 8/2000 Feuerstein
6,103,639 A * 8/2000 Adams
6,150,557 A * 11/2000 Adams

FOREIGN PATENT DOCUMENTS

EP 149884 * 7/1985
EP 384271 * 8/1990
JP 60058981 * 4/1985
JP 05070446 * 3/1993
JP 10087490 * 4/1998
WO WO-9735855 A1 * 10/1997
WO WO-9735856 A1 * 10/1997
WO WO-9807425 A1 * 2/1998

* cited by examiner

*Primary Examiner*—D. Margaret Seaman
(74) *Attorney, Agent, or Firm*—Mark Chao; Elaine M. Ramesh

(57) ABSTRACT

A pharmaceutical composition for antagonizing adenosine at adenosine $A_3$ receptors which comprises a 1,3-azole compound substituted on the 4- or 5-position, or both, by a pyridyl which may be substituted is provided and can be used as a prophylactic and therapeutic agent for asthma, allergosis, inflammation, and so on.

9 Claims, No Drawings

ADENOSINE $A_3$ RECEPTOR ANTAGONISTS

This Application is the National Stage of International Application Serial No. PCT/JP98/04837, filed Oct. 26, 1998.

TECHNICAL FIELD

The present invention relates to an agent for antagonizing adenosine at adenosine $A_3$ receptors and a novel thiazole compound having a superior antagonistic activity at adenosine $A_3$ receptor.

BACKGROUND ART

As subtypes of adenosine receptors, $A_1$, $A_{2a}$, $A_{2b}$ and $A_3$ are known. Adenosine induces bronchial constriction in asthma patients, while theophylline, which is known as an antiasthmatic, antagonizes adenosine. Recently several reports showed that activation of adenosine A3 receptors in rats promotes degranulation of mast cells [Journal of Biological Chemistry, 268, 16887–16890 (1993)], that adenosine $A_3$ receptors exist on peripheral blood eosinophils and that the stimulation of adenosine $A_3$ receptors activates phospholipase C and elevates intracellular calcium [Blood, 88, 3569–3574 (1996)].

Currently, as selective $A_3$ adenosine receptor antagonists, xanthine derivatives are reported in GB-A-2288733 and WO 95/11681, and the following compounds are reported in Journal of Medicinal Chemistry, 40, 2596–2608(1997).

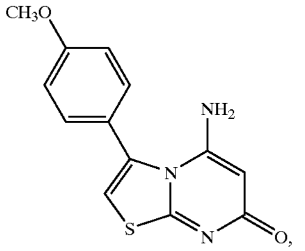

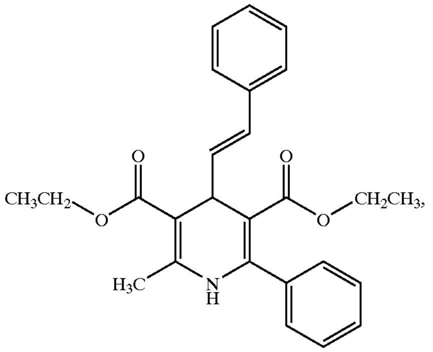

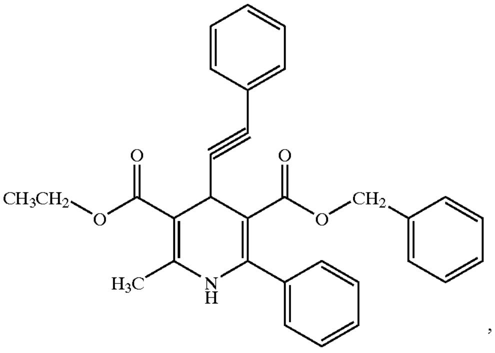

,

-continued

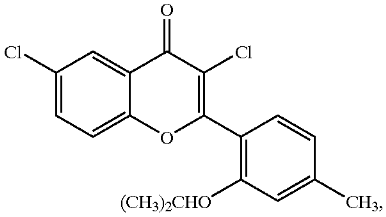

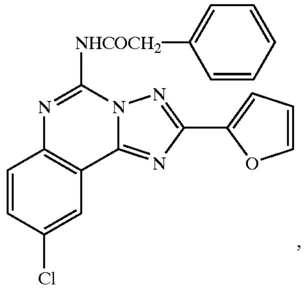

,

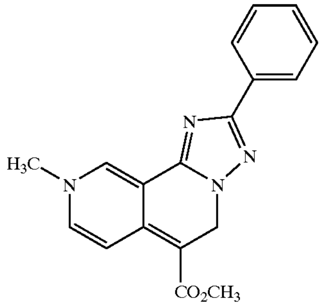

The following thiazole compounds are known.

1) A thiazole derivative of the formula:

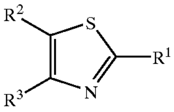

wherein $R^1$ represents i) cycloalkyl, ii) cyclic amino, iii) amino which may be substituted by 1 or 2 substituents selected from the group consisting of lower alkyl, phenyl, acetyl and lower alkoxycarbonylacetyl, iv) alkyl which may be substituted by a substituent selected from the group consisting of hydroxy, carboxy and lower alkoxycarbonyl or v) phenyl which may be substituted by a substituent selected from the group consisting of carboxy, 2-carboxyethenyl and 2-carboxy-1-propenyl; $R^2$ represents pyridyl which may be substituted by a lower alkyl; and $R^3$ represents phenyl which may be substituted by a substituent selected from the group consisting of lower alkoxy, lower alkyl, hydroxy, halogen and methylenedioxy, or a salt thereof, which has analgesic, anti-pyretic, anti-inflammatory, anti-ulcer, thromboxane $A_2$ ($TXA_2$) synthetase inhibitory and platelet aggregation inhibiting actions (JP-A-60-58981).

2) A 1,3-thiazole derivative of the formula:

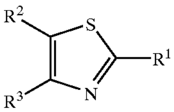

wherein $R^1$ represents an optionally substituted alkyl, alkenyl, aryl, aralkyl, cycloalkyl, heterocyclic group having carbon as the attachment point or amino; $R^2$ represents pyridyl which may be substituted by an alkyl; and $R^3$ represents phenyl which may be substituted, or a salt thereof, which has analgesic, anti-pyretic, anti-inflammatory, anti-ulcer, thromboxane $A_2$ ($TXA_2$) synthetase inhibitory and platelet aggregation inhibiting actions (JP-A-61-10580).

3) A 1,3-thiazole derivative of the formula:

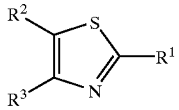

wherein $R^1$ represents an optionally substituted alkyl, alkenyl, aryl, aralkyl, cycloalkyl, heterocyclic group having carbon as the attachment point or amino; $R^2$ represents pyridyl which may be substituted by an alkyl; and $R^3$ represents aryl which may be substituted, or a salt thereof, which has analgesic, anti-pyretic, anti-inflammatory, anti-ulcer, thromboxane $A_2$ ($TXA_2$) synthetase inhibitory and platelet aggregation inhibiting actions (U.S. Pat. No. 4,612, 321).

4) A compound of the formula:

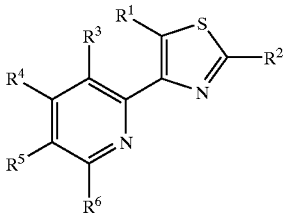

wherein $R^1$ is an optionally substituted phenyl, $R^2$ is $C_{1-6}$ alkyl or $(CH_2)_nAr$, n is 0–2, Ar is an optionally substituted phenyl, $R^3$ is hydrogen or $C_{1-4}$ alkyl, $R^4$ is hydrogen, $C_{1-4}$ alkyl, etc, $R^5$ is hydrogen or $C_{1-4}$ alkyl, $R^6$ is hydrogen, $C_{1-4}$ alkyl, etc, or salt thereof, which has an activity of inhibiting gastric acid secretion (JP-A-07-503023, WO 93/15071).

5) A compound of the formula:

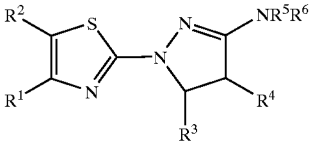

wherein $R^1$ is pyridyl, etc, $R^2$ is phenyl, etc, $R^3$ and $R^4$ are hydrogen or methyl, $R^5$ is methyl, etc, $R^6$ is hydrogen or methyl, etc, or a salt thereof, which is useful as anti-inflammatory and anti-allergic agents (DE-A-3601411).

6) A compound of the formula:

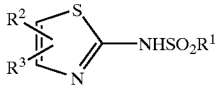

wherein $R^1$ is lower alkyl substituted by halogen, $R^2$ is pyridyl, etc, $R^3$ is phenyl, etc, or a salt thereof, which has anti-inflammatory, antipyretic, analgesic and anti-allergic activities (JP-A-5-70446).

From the prior art described above, it is thought that adenosine causes asthma through its binding to adenosine $A_3$ receptor, therefore $A_3$ adenosine receptor antagonists are expected to become a new type of antiasthma drug. Accordingly, an agent for antagonizing adenosine at adenosine $A_3$ receptors which has potent antagonistic activity, good bioavailability upon administration and good metabolical stability are expected to have potent therapeutic effects for asthma, inflammation, Addison's diseases, autoallergic hemolytic anemia, Crohn's diseases, psoriasis, rheumatism and diabetes. However, as a prophylactic and therapeutic agent for adenosine $A_3$ receptor-related diseases, no good agents for antagonising adenosine at gadenosine $A_3$ receptors are known in terms of potency, safety, bioavailability, and metabolic'stability. Therefore a good agent for antagonising adenosine at adenosine $A_3$ receptor is expected to be developed.

DISCLOSURE OF INVENTION

We, the present inventors, have studied various compounds having an antagonistic activity at adenosine $A_3$ receptors, and as a result, have found for the first time that a 1,3-azole compound substituted on the 4- or 5-position, or both, by a pyridyl which may be substituted (hereinafter sometimes referred to briefly as compound (I)], has an unexpected, excellent selective affinity to adenosine $A_3$ receptor, antagonistic activity at adenosine $A_3$ receptor and high stability, and is therefore satisfactory as a medicine.

Compound (I) comprises, for example, a compound of the formula:

(Ia)

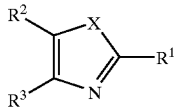

wherein $R^1$ represents a hydrogen atom, a hydrocarbon group which may be substituted, a heterocyclic group which may be substituted, an amino which may be substituted or an acyl;

at least one of $R^2$ and $R^3$ represents a hydrogen atom, a pyridyl which may be substituted or an aromatic hydrocarbon group which may be substituted, and the other represents a pyridyl which may be substituted; and X represents a sulfur atom which may be oxidized, an oxygen atom or a group of the formula: $NR^4$ wherein $R^4$ represents a hydrogen atom, a hydrocarbon group which may be substituted or an acyl;

or a salt thereof, which may be N-oxidized [hereinafter sometimes referred to briefly as compound (Ia)], and a novel compound of the formula:

(Ib)

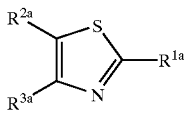

wherein $R^{1a}$ represents (i) an aromatic heterocyclic group which may be substituted, (ii) an amino which may be substituted by substituent(s) selected from the group consisting of a substituted carbonyl and a hydrocarbon group which may be substituted, (iii) a cyclic amino which may be substituted or (iv) an acyl;

$R^{2a}$ represents an aromatic hydrocarbon group which may be substituted; and $R^{3a}$ represents a pyridyl which may be substituted, or a salt thereof [hereinafter sometimes referred to briefly as compound (Ib)] being within the scope of compound (Ia).

On the basis of these findings, the inventors have completed the present invention.

Specifically, the present invention relates to:

(1) A pharmaceutical composition for antagonizing adenosine at adenosine $A_3$ receptors which comprises compound (I);

(2) a composition of the above (1), wherein the 1,3-azole compound is compound (Ia);

(3) a composition of the above (2), wherein $R^1$ is (i) a hydrogen atom, (ii) a $C_{1-8}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents, (iii) a 5- to 14-membered heterocyclic group containing 1 to 4 hetero atoms selected from the group consisting of nitrogen, sulfur and oxygen atoms in addition to carbon atoms, which group may be substituted by 1 to 5 substituents, (iv) an amino which may be substituted by 1 or 2 substituents selected from the group consisting of (a) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents, (b) a $C_{1-6}$ alkylidene group which may be substituted by 1 to 5 substituents, (c) a 5- to 14-membered heterocyclic group containing 1 to 4 hetero atoms selected from the group consisting of nitrogen, sulfur and oxygen atoms in addition to carbon atoms, which group may be substituted by 1 to 5 substituents, and (d) an acyl of the formula: —(C═O)—$R^5$, —(C═O)—$OR^5$, —(C═O)—$NR^5R^6$, —(C═S)—$NHR^5$ or —$SO_2$—$R^7$ wherein $R^5$ is (i') a hydrogen atom, (ii') a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents or (iii') a 5- to 14-membered heterocyclic group containing 1 to 4 hetero atoms selected from the group consisting of nitrogen, sulfur and oxygen atoms in addition to carbon atoms, which group may be substituted by 1 to 5 substituents; $R^6$ is a hydrogen atom or $C_{1-6}$ alkyl; and $R^7$ is (i') a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents or (ii') a 5- to 14-membered heterocyclic group containing 1 to 4 heteroatoms selected from the group consisting of nitrogen, sulfur and oxygen atoms in addition to carbon atoms, which group may be substituted by 1 to 5 substituents, (v) a 5- to 7-membered non-aromatic cyclic amino optionally containing 1 to 4 hetero atoms selected from the group consisting of nitrogen, sulfur and oxygen atoms in addition to carbon atoms and at least one nitrogen atom, which may be substituted by 1 to 3 substituents selected from the group consisting of $C_{1-6}$ alkyl, $C_{6-14}$ aryl, $C_{1-6}$ alkyl-carbonyl, 5- to 10-membered aromatic heterocyclic group and oxo, or (vi) an acyl of the formula: —(C═O)—$R^5$, —(C═O)—$OR^5$, —(C═O)—$NR^5R^6$, —(C═S)—$NHR^5$ or —$SO_2$—$R^7$ wherein each symbol is as defined above;

at least one of $R^2$ and $R^3$ is (i) a hydrogen atom, (ii) a pyridyl which may be substituted by 1 to 5 substituents or (iii) a $C_{6-14}$ aryl which may be substituted by 1 to 5 substituents in which a substituent can form, together with a neighboring substituent, a 4- to 7-membered non-aromatic carbocyclic ring;

and the other is a pyridyl which may be substituted by 1 to 5 substituents; and

X is a sulfur atom which may be oxidized, an oxygen atom or a group of the formula: $NR^4$ wherein $R^4$ is (i) a hydrogen atom, (ii) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents or (iii) an acyl of the formula: —(C═O)—$R^5$; —(C═O)—$OR^5$, —(C═O)—$NR^5R^6$, —(C═S)—$NHR^5$ or —$SO_2$—$R^7$ wherein each symbol is as defined above, wherein the above "substituents" are selected from the group consisting of (1) halogen atoms, (2) $C_{1-3}$ alkylenedioxy, (3) nitro, (4) cyano, (5) optionally halogenated $C_{1-6}$ alkyl, (6) optionally halogenated $C_{2-6}$ alkenyl, (7) carboxy $C_{2-6}$ alkenyl, (8) optionally halogenated $C_{2-6}$ alkynyl, (9) optionally halogenated $C_{3-6}$ cycloalkyl, (10) $C_{6-14}$ aryl, (11) optionally halogenated $C_{1-8}$ alkoxy, (12) $C_{1-6}$ alkoxy-carbonyl-$C_{1-6}$ alkoxy, (13) hydroxy, (14) $C_{6-14}$ aryloxy, (15) $C_{7-16}$ aralkyloxy,(16) mercapto, (17) optionally halogenated $C_{1-6}$ alkylthio, (18) $C_{6-14}$ arylthio, (19) $C_{7-16}$ aralkylthio, (20) amino, (21) mono-$C_{1-6}$ alkylamino, (22) mono-$C_{6-14}$ arylamino, (23) di-$C_{1-6}$ alkylamino, (24) di-$C_{6-14}$ arylamino, (25) formyl, (26) carboxy, (27) $C_{1-6}$ alkyl-carbonyl, (28) $C_{3-6}$ cycloalkyl-carbonyl, (29) $C_{1-6}$ alkoxy-carbonyl, (30) $C_{6-14}$ aryl-carbonyl, (31) $C_{7-16}$ aralkyl-carbonyl, (32) $C_{6-14}$ aryloxy-carbonyl, (33) $C_{7-16}$ aralkyloxy-carbonyl, (34) 5- or 6-membered heterocycle carbonyl, (35) carbamoyl, (36) mono-$C_{1-6}$ alkyl-carbamoyl, (37) di-$C_{1-6}$ alkyl-carbamoyl, (38) $C_{6-14}$ aryl-carbamoyl, (39) 5- or 6-membered heterocycle carbamoyl, (40) $C_{1-6}$ alkylsulfonyl, (41) $C_{6-14}$ arylsulfonyl, (42) formylamino, (43) $C_{1-6}$ alkyl-carbonylamino, (44) $C_{6-14}$ aryl-carbonylamino, (45) $C_{1-6}$ alkoxy-carbonylamino, (46) $C_{1-6}$ alkylsulfonylamino, (47) $C_{6-14}$ arylsulfonylamino, (48) $C_{1-6}$ alkyl-carbonyloxy, (49) $C_{6-14}$ aryl-carbonyloxy, (50) $C_{1-6}$ alkoxy-carbonyloxy, (51) mono-$C_{1-6}$ alkyl-carbamoyloxy, (52) di-$Ci_6$ alkyl-carbamoyloxy, (53) $C_{6-14}$ aryl-carbamoyloxy, (54) nicotinoyloxy, (55) 5- to 7-membered saturated cyclic amino which may be substituted by 1 to 3 substituents selected from the group consisting of $C_{1-6}$ alkyl, $C_{6-14}$ aryl, $C_{1-6}$ alkyl-carbonyl, 5- to 10-membered aromatic heterocyclic group and oxo, (56) 5- to 10-membered aromatic heterocyclic group and (57) sulfo;

(4) a composition of the above (2), wherein $R^1$ is an amino which may be substituted;

(5) a composition of the above (3), wherein $R^1$ is an amino which may be substituted by 1 or 2 acyl of the formula: —(C═O)—$R^5$, —(C═O)—$OR^5$, —(C═O)—$NR^5R^6$, —(C═S)—$NHR^5$ or —$SO_2$—$R^7$;

(6) a composition of the above (3), wherein $R^1$ is an amino which may be substituted by 1 or 2 acyl of the formula: —(C═O)—$R^5$ or —(C═O)—$NR^5R^6$;

(7) a composition of the above (3), wherein $R^1$ is a 5- to 7-membered non-aromatic cyclic amino optionally containing 1 to 4 hetero atoms selected from the group consisting of nitrogen, sulfur and oxygen atoms in addition to carbon atoms and at least one nitrogen atom, which may be substituted by 1 to 3 substituents selected from the group consisting of $C_{1-6}$ alkyl, $C_{6-14}$ aryl, $C_{1-6}$ alkyl-carbonyl, 5- to 10-membered aromatic heterocyclic group and oxo;

(8) a composition of the above (2), wherein X is S;

(9) a composition of the above (2), wherein $R^2$ is a pyridyl which may be substituted;

(10) a composition of the above (2), wherein $R^3$ is a $C_{6-14}$ aryl which may be substituted;

(11) a composition of the above (3), wherein $R^1$ is an amino which may be substituted by 1 or 2 acyl of the formula: —(C=O)—$R^5$ or —(C=O)—$NR^5R^6$;

$R^2$ is a pyridyl which may be substituted by 1 to 5 $C_{1-6}$ alkyl;

$R^3$ is a $C_{6-14}$ aryl which may be substituted by 1 to 5 substituents selected from the group consisting of halogen atoms, optionally halogenated $C_{1-6}$ alkyl, optionally halogenated $C_{1-6}$ alkoxy and carboxy; and X is S;

(12) a composition of the above (2), wherein $R^1$ is (i) a $C_{1-8}$ alkyl, $C_{3-6}$ cycloalkyl or $C_{6-14}$ aryl group which may be substituted by 1 to 5 substituents selected from the group consisting of halogen atoms, optionally halogenated $C_{1-6}$ alkyl, carboxy $C_{2-6}$ alkenyl, optionally halogenated $C_{1-6}$ alkoxy, $C_{1-6}$ alkoxy-carbonyl-$C_{1-6}$ alkoxy, hydroxy, amino, mono-C-$_{1-6}$ alkylamino, carboxy, $C_{1-6}$ alkoxy-carbonyl, mono-$C_{1-6}$ alkyl-carbamoyl and $C_{6-14}$ aryl-carbonylamino, (ii) a 5-membered heterocyclic group, (iii) an amino which may be substituted by 1 or 2 substituents selected from the group consisting of (1) $C_{1-6}$ alkyl, (2) $C_{6-14}$ aryl, (3) $C_{7-16}$ aralkyl,(4) 6-membered heterocyclic group, (5) a $C_{1-6}$ alkyl-carbonyl, $C_{3-6}$ cycloalkyl-carbonyl, $C_{6-14}$ aryl-carbonyl, $C_{7-16}$ aralkyl-carbonyl, $C_{1-6}$ alkyl-carbamoyl or 5- or 6-membered heterocycle carbonyl group which may be substituted by 1 to 3 substituents selected from the group consisting of halogen atoms, $C_{1-6}$ alkyl, $C_{1-6}$ alkoxy, carboxy and $C_{1-6}$ alkoxy-carbonyl, and (6) di-$C_{1-6}$ alkylamino-$C_{1-6}$ alkylidene, (iv) a 5- or 6-membered non-aromatic cyclic amino which may be substituted by $C_{1-6}$ alkyl-carbonyl or oxo, or (v) carboxy;

$R^2$is a pyridyl which may be substituted by 1 to 3 $C_{1-6}$ alkyl;

$R^3$ is a $C_{6-10}$ aryl which may be substituted by 1 to 3 substituents selected from the group consisting of halogen atoms, $C_{1-3}$ alkylenedioxy, optionally halogenated $C_{1-6}$ alkyl, carboxy $C_{2-6}$ alkenyl, optionally halogenated $C_{1-8}$ alkoxy, hydroxy, $C_{7-16}$ aralkyloxy and $C_{1-6}$ alkyl-carbonyloxy, in which the alkyl group can form, together with a neighboring alkyl group, a 5-membered non-aromatic carbocyclic ring; and X is S;

(13) an adenosine $A_3$ receptor antagonist which comprises a 1,3-azole compound substituted on the 4- or 5-position, or both, by a pyridyl which may be substituted;

(14) a composition of the above (1), which is for preventing and/or treating asthma or allergosis;

(15) compound (Ib);

(16) a compound of the above (15), wherein $R^{1a}$ is an amino which may be substituted by 1 or 2 substituents selected from the group consisting of $C_{1-6}$ alkyl, $C_{1-6}$ alkyl-carbonyl, $C_{6-14}$ aryl-carbonyl and $C_{1-6}$ alkyl-carbamoyl;

$R^{2a}$ is a phenyl which may be substituted by 1 to 3 substituents selected from the group consisting of halogen atoms, optionally halogenated $C_{1-6}$ alkyl and optionally halogenated $C_{1-6}$ alkoxy; and $R^{3a}$ is a pyridyl;

(17) a process for producing compound (Ib), which comprises reacting a compound of the formula:

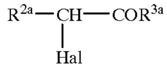

wherein Hal represents halogen atoms and other symbols are as defined above, or a salt thereof with a compound of the formula:

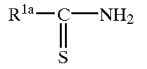

wherein $R^{1a}$ is as defined above, or a salt thereof, optionally in the presence of a base;

(18) a pharmaceutical composition which comprises compound (Ib);

(19) a composition of the above (18) which is an agent for antagonizing adenosine at adenosine $A_3$ receptors;

(20) a composition of the above (18) which is for preventing and/or treating asthma or allergosis;

(21) a method for preventing and/or treating diseases related to adenosine $A_3$ receptor in mammal, which comprises administering to said mammal an effective amount of a compound of the above (1) or a pharmaceutically acceptable salt thereof with a pharmaceutically acceptable excipient, carrier or diluent; and

(22) use of a compound of the above (1) or a salt thereof for manufacturing a pharmaceutical composition for preventing and/or treating diseases related to adenosine $A_3$ receptor, and so forth.

In this specification, the "acyl" includes, for example, an acyl of the formula: —(C=O)—$R^5$, —(C=O)—$OR^5$, —(C=O)—$NR^5R^6$, —(C=S)—$NHR^5$ or —$SO_2$—$R^7$ wherein $R^5$ represents a hydrogen atom, a hydrocarbon group which may be substituted or a heterocyclic group which may be substituted; $R^6$ represents a hydrogen atom or $C_{1-6}$ alkyl; and $R^7$ represents a hydrocarbon group which may be substituted or a heterocyclic group which may be substituted.

In the above formulae, the "hydrocarbon group" of the "hydrocarbon group which may be substituted" for $R^5$ includes, for example, an acyclic or cyclic hydrocarbon group such as alkyl, alkenyl, alkynyl, cycloalkyl, aryl, aralkyl, etc. Among them, $C_{1-16}$ acyclic or cyclic hydrocarbon group is preferable.

The preferred "alkyl" is for example $C_{1-6}$ alkyl such as methyl, ethyl, propyl, isopropyl, butyl, isobutyl, sec-butyl, tert-butyl, pentyl, hexyl, etc.

The preferred "alkenyl" is for example $C_{2-6}$ alkenyl such as vinyl, allyl, isopropenyl, 1-butenyl, 2-butenyl, 3-butenyl, 2-methyl-2-propenyl, 1-methyl-2-propenyl, 2-methyl-1-propenyl, etc.

The preferred "alkynyl" is for example $C_{2-6}$ alkynyl such as ethynyl, propargyl, 1-butynyl, 2-butynyl, 3-butynyl, 1-hexynyl, etc.

The preferred "cycloalkyl" is for example $C_{3-6}$ cycloalkyl such as cyclopropyl, cyclobutyl, cyclopentyl, cyclohexyl, etc.

The preferred "aryl" is for example $C_{6-14}$ aryl such as phenyl, 1-naphthyl, 2-naphthyl, 2-biphenylyl, 3-biphenylyl, 4-biphenylyl, 2-anthryl, etc.

The preferred "aralkyl" is for example $C_{7-16}$ aralkyl such as benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, etc.

Examples of the "substituents" of the "hydrocarbon group which may be substituted" for $R^5$ include halogen atoms (e.g., fluoro, chloro, bromo, iodo, etc.), $C_{1-3}$ alkylenedioxy (e.g., methylenedioxy, ethylenedioxy, etc.), nitro, cyano, optionally halogenated $C_{1-6}$ alkyl, optionally halogenated $C_{2-6}$ alkenyl, carboxy $C_{2-6}$ alkenyl (e.g., 2-carboxyethenyl, 2-carboxy-2-methylethenyl, etc.), optionally halogenated $C_{2-6}$ alkynyl, optionally halogenated $C_{3-6}$ cycloalkyl, $C_{6-14}$ aryl (e.g., phenyl, 1-naphthyl, 2-naphthyl, 2-biphenylyl, 3-biphenylyl, 4-biphenylyl, 2-anthryl, etc.), optionally halogenated $C_{1-8}$ alkoxy, $C_{1-6}$ alkoxy-carbonyl-$C_{1-6}$ alkoxy (e.g., ethoxycarbonylmethyloxy, etc.), hydroxy, $C_{6-14}$ aryloxy (e.g., phenyloxy, 1-naphthyloxy, 2-naphthyloxy, etc.), $C_{7-16}$ aralkyloxy (e.g., benzyloxy, phenethyloxy, etc.), mercapto, optionally halogenated $C_{1-6}$ alkylthio, $C_{6-14}$ arylthio (e.g., phenylthio, 1-naphthylthio, 2-naphthylthio, etc.), $C_{7-16}$ aralkylthio (e.g., benzylthio, phenethylthio, etc.), amino, mono-$C_{1-6}$ alkylamino (e.g., methylamino, ethylamino, etc.), mono-$C_{6-14}$ arylamino (e.g., phenylamino, 1-naphthylamino, 2-naphthylamino, etc.), di-$C_{1-6}$ alkylamino (e.g., dimethylamino, diethylamino, ethylmethylamino, etc.), di-$C_{6-14}$ arylamino (e.g., diphenylamino, etc.), formyl, carboxy, $C_{1-6}$ alkyl-carbonyl (e.g., acetyl, propionyl, etc.), $C_{3-6}$ cycloalkyl-carbonyl (e.g., cyclopropylcarbonyl, cyclopentylcarbonyl, cyclohexylcarbonyl, etc.), $C_{1-6}$ alkoxy-carbonyl (e.g., methoxycarbonyl, ethoxycarbonyl, propoxycarbonyl, tert-butoxycarbonyl, etc.), $C_{6-14}$ aryl-carbonyl (e.g., benzoyl, 1-naphthoyl, 2-naphthoyl, etc.), $C_{7-16}$ aralkyl-carbonyl (e.g., phenylacetyl, 3-phenylpropionyl, etc.), $C_{6-14}$ aryloxy-carbonyl (e.g., phenoxycarbonyl, etc.), $C_{7-16}$ aralkyloxy-carbonyl (e.g., benzyloxycarbonyl, phenethyloxycarbonyl, etc.), 5- or 6-membered heterocycle carbonyl (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl, etc.), carbamoyl, mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamroyl, diethylcarbamoyl, ethylmethylcarbamoyl, etc.), $C_{6-14}$ aryl-carbamoyl (e.g., phenylcarbamoyl, 1-naphthylcarbamoyl, 2-naphthylcarbamoyl, etc.), 5- or 6-membered heterocycle carbamoyl (e.g., 2-pyridylcarbamoyl, 3-pyridylcarbamoyl, 4-pyridylcarbamoyl, 2-thienylcarbamoyl, 3-thienylcarbamoyl, etc.), $C_{1-6}$ alkylsulfonyl (e.g., methylsulfonyl, ethylsulfonyl, etc.), $C_{6-14}$ arylsulfonyl (e.g., phenylsulfonyl, 1-naphthylsulfonyl, 2-naphthylsulfonyl, etc.), formylamino, $C_{1-6}$ alkyl-carbonylamino (e.g., acetylamino, etc.), $C_{6-14}$ aryl-carbonylamino (e.g., benzoylamino, naphthoylamino, etc.), $C_{1-6}$ alkoxy-carbonylamino (e.g., methoxycarbonylamino, ethoxycarbonylamino, propoxycarbonylamino, butoxycarbonylamino, etc.), $C_{1-6}$ alkylsulfonylamino (e.g., methylsulfonylamino, ethylsulfonylamino, etc.), $C_{6-14}$ arylsulfonylamino (e.g., phenylsulfonylamino, 2-naphthylsulfonylamino, 1-naphthylsulfonylamino, etc.), $C_{1-6}$ alkyl-carbonyloxy (e.g., acetoxy, propionyloxy, etc.), $C_{6-14}$ aryl-carbonyloxy (e.g., benzoyloxy, naphthylcarbonyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono-$C_{1-6}$ alkyl-carbamoyloxy (e.g., methylcarbamoyloxy, ethylcarbamoyloxy, etc.), di-$C_{1-6}$ alkyl-carbamoyloxy (e.g., dimethylcarbamoyloxy, diethylcarbamoyloxy, etc.), $C_{6-14}$ aryl-carbamoyloxy (e.g., phenylcarbamoyloxy, naphthylcarbamoyloxy, etc.), nicotinoyloxy, 5- to 7-membered saturated cyclic amino which may be substituted, 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.), sulfo, and so forth.

The "hydrocarbon group" may have 1 to 5, preferably 1 to 3 substituents as mentioned above at possible positions of the hydrocarbon group and, when the number of substituents is two or more, those substituents may be the same as or different from one another.

The above-mentioned "optionally halogenated $C_{1-6}$ alkyl" includes, for example, $C_{1-6}$ alkyl (e.g., methyl, ethyl, propyl, isopropyl, butyl, isobutyl, sec-butyl, tert-butyl, pentyl, hexyl, etc.) which may have 1 to 5, preferably 1 to 3 halogen atoms (e.g., fluoro, chloro, bromo, iodo, etc.). Concretely mentioned is methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.

The above-mentioned "optionally halogenated $C_{2-6}$ alkenyl" includes, for example, $C_{2-6}$ alkenyl (e.g., vinyl, propenyl, isopropenyl, 2-buten-1-yl, 4-penten-1-yl, 5-hexen-1-yl, etc.) which may have 1 to 5, preferably 1 to 3 halogen atoms (e.g., fluoro, chloro, bromo, iodo, etc.).

The above-mentioned "optionally halogenated $C_{2-6}$ alkynyl" includes, for example, $C_{2-6}$ alkynyl (e.g., 2-butyn-1-yl, 4-pentyn-1-yl, 5-hexyn-1-yl, etc.) which may have 1 to 5, preferably 1 to 3 halogen atoms (e.g., fluoro, chloro, bromo, iodo, etc.).

The above-mentioned "optionally halogenated $C_{3-6}$ cycloalkyl" includes, for example, $C_{3-6}$ cycloalkyl (e.g., cyclopropyl, cyclobutyl, cyclopentyl, cyclohexyl, etc.) which may have 1 to 5, preferably 1 to 3 halogen atoms (e.g., fluoro, chloro, bromo, iodo, etc.). Concretely mentioned is cyclopropyl, cyclobutyl, cyclopentyl, cyclohexyl, 4, 4 -dichlorocyclohexyl, 2,2,3,3-tetrafluorocyclopentyl, 4-chlorocyclohexyl, etc.

The above-mentioned "optionally halogenated $C_{1-8}$ alkoxy" includes, for example, $C_{1-8}$ alkoxy (e.g., methoxy, ethoxy, propoxy, isopropoxy, butoxy, isobutoxy, sec-butoxy, pentyloxy, hexyloxy, etc.) which may have 1 to 5, preferably 1 to 3 halogen atoms (e.g., fluoro, chloro, bromo, iodo, etc.). Concretely mentioned is methoxy, difluoromethoxy, trifluoromethoxy,ethoxy, 2,2,2-trifluoroethoxy, propoxy, isopropoxy, butoxy, 4,4,4-trifluorobutoxy, isobutoxy, sec-butoxy, pentyloxy, hexyloxy, etc.

The above-mentioned "optionally halogenated $C_{1-6}$ alkylthio" includes, for example, $C_{1-6}$ alkylthio (e.g., methylthio, ethylthio, propylthio, isopropylthio, butylthio, sec-butylthio, tert-butylthio, etc.) which may have 1 to 5, preferably 1 to 3 halogen atoms (e.g., fluoro, chloro, bromo, iodo, etc.). Concretely mentioned is methylthio, difluoromethylthio, trifluoromethylthio, ethylthio, propylthio, isopropylthio, butylthio, 4,4,4-trifluorobutylthio, pentylthio, hexylthio, etc.

The above-mentioned "5- to 7-membered saturated cyclic amino" of the "5- to 7-membered saturated cyclic amino which may be substituted" includes, for example, 5- to 7-membered saturated cyclic amino optionally containing 1 to 4 hetero atoms selected from the group consisting of nitrogen, sulfur and oxygen atoms in addition to carbon atoms and at least one nitrogen atom, such as pyrrolidin-1-yl, piperidino, piperazin-1-yl, morpholino, thiomorpholino, tetrahydroazepin-1-yl, etc.

The "substituents" of the "5- to 7-membered saturated cyclic amino which may be substituted" include, for example, 1 to 3 substituents selected from the group consisting of $C_{1-6}$ alkyl (e.g., methyl, ethyl, propyl, isopropyl, butyl, isobutyl, sec-butyl, tert-butyl, pentyl, hexyl, etc.), $C_{6-14}$ aryl (e.g., phenyl, 1-naphthyl, 2-naphthyl, 2-biphenylyl, 3-biphenylyl, 4-biphenylyl, 2-anthryl, etc.), $C_{1-6}$ alkyl-carbonyl (e.g., acetyl, propionyl, etc.), and 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.), oxo, and so forth.

The "heterocyclic group" of the "heterocyclic group which may be substituted" for $R^5$ includes, for example, a monovalent group formed by removing an optional hydrogen atom from a 5- to 14-membered (monocyclic, bicyclic or tricyclic) heterocyclic ring containing 1 to 4 hetero atoms of 1 or 2 species selected from the group consisting of nitrogen, sulfur and oxygen atoms in addition to carbon atoms, preferably, (i) a 5- to 14-membered, preferably, 5- to 10-membered aromatic heterocyclic ring, (ii) a 5- to 10-membered non-aromatic heterocyclic ring and (iii) a 7- to 10-membered bridged heterocyclic ring, etc.

The above-mentioned "5- to 14-membered, preferably 5- to 10-membered aromatic heterocyclic ring" includes, for example, an aromatic heterocyclic ring such as thiophene, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolidine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine, etc.; and a ring as formed through condensation of those. rings, preferably a monocyclic ring, with one or more, preferably one or two aromatic rings (e.g., benzene ring, etc.), etc.

The above-mentioned "5- to 10-membered non-aromatic heterocyclic ring" includes, for example, pyrrolidine, imidazoline, pyrazolidine, pyrazoline, piperidine, piperazine, morpholine, thiomorpholine, dioxazole, oxadiazoline, oxathiazole, thiadiazoline, triazoline, thiadiazole, dithiazole, etc.

The above-mentioned "7- to 10-membered bridged heterocyclic ring" includes, for example, quinuclidine, 7-azabicyclo[2.2.1]heptane, etc.

Preferable examples of the "heterocyclic group" include, for example, a 5- to 14-membered (preferably 5- to 10-membered) (monocyclic or bicyclic) heterocyclic group containing 1 to 4 hetero atoms of 1 or 2 species selected from the group consisting of nitrogen, sulfur and oxygen atoms in addition to carbon atoms. Concretely mentioned are an aromatic heterocyclic group such as 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isoxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc; and a non-aromatic heterocyclic group such as 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino, etc.

Among these groups, a 5- or 6-membered heterocyclic group containing 1 to 3 hetero atoms selected from the group consisting of nitrogen, sulfur and oxygen atoms in addition to carbon atoms. Concretely mentioned are 2-thienyl, 3-thienyl, 2-pyridyl, 3-pyridyl, 4-pyridyl, 2-furyl, 3-furyl, pyrazinyl, 2-pyrimidinyl, 3-pyrrolyl, 3-pyridazinyl, 3-isothiazolyl, 3-isoxazolyl, 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino, etc.

The "substituents" of the "heterocyclic group which may be substituted" are the same as those mentioned above for the "substituents" of the "hydrocarbon group which may be substituted" for $R^5$.

The "heterocyclic group" may have 1 to 5, preferably 1 to 3 substituents as mentioned above at possible positions of the heterocyclic group and, when the number of substituents is two or more, those substituents may be the same as or different from one another.

The "$C_{1-6}$ alkyl" for $R^6$ includes, for example, methyl, ethyl, propyl, isopropyl, butyl, isobutyl, sec-butyl, tert-butyl, pentyl, hexyl, etc.

The "hydrocarbon group which may be substituted" and the "heterocyclic group which may be substituted" for $R^7$ include, for example, the "hydrocarbon group which may be substituted" and the "heterocyclic group which may be substituted" for $R^5$ above, respectively.

The "1,3-azole compound" of the "1,3-azole compound substituted on the 4- or 5-position, or both, by a pyridyl which may be substituted" in the above compound (I) includes, for example, 1,3-thiazole, 1,3-oxazole, 1,3-imidazole, and so forth.

The "substituents" of the "pyridyl which may be substituted" in the "1,3-azole compound substituted on the 4- or 5-position, or both, by a pyridyl which may be substituted" are, for example, the same as those mentioned above for the "substituents" of the "hydrocarbon group which may be substituted" for $R^5$.

The "pyridyl" may have 1 to 5, preferably 1 to 3 substituents as mentioned above at possible positions thereof and, when the number of substituents is two or more, those substituents may be the same as or different from one another. The ring-constituting nitrogen atom in the "pyridyl" may be oxidized (N-oxidized).

The above-mentioned "1,3-azole compound substituted on the 4- or 5-position, or both, by a pyridyl which may be substituted" may further have 1 to 4, preferably 1 to 3 substituents. When the number of substituents is two or more, those substituents may be the same as or different from one another.

Such "substituents" include, for example, a hydrocarbon group which may be substituted, a heterocyclic group which may be substituted, amino which may be substituted, acyl, and so forth.

The above-mentioned "hydrocarbon group which may be substituted" and the "heterocyclic group which may be substituted" includes, for example, the "hydrocarbon group which may be substituted" and the "heterocyclic group which may be substituted" for $R^5$ above, respectively.

The above-mentioned "amino which may be substituted" includes, for example, (1) an amino which may be substituted by 1 or 2 substituents and (2) a cyclic amino which may be substituted.

The "substituents" of the above (1) "amino which may be substituted by 1 or 2 substituents" include, for example, a hydrocarbon group which may be substituted, a heterocyclic group which may be substituted, acyl, alkylidene which may be substituted, and so forth. The "hydrocarbon group which may be substituted" and the "heterocyclic group which may be substituted" include, for example, the "hydrocarbon group which may be substituted" and the "heterocyclic group which may be substituted" for $R^5$ above, respectively.

The above-mentioned "alkylidene" of the "alkylidene which may be substituted" include, for example, $C_{1-6}$ alkylidene such as methylidene, ethylidene, propylidene, etc. The "substituents" of the "alkylidene which may be substituted" includes, for example, the same as those mentioned above for the "substituents" of the "hydrocarbon group which may be substituted" for $R^5$. The number of such substituent is 1 to 5, preferably 1 to 3.

When the number of substituents of the above "amino which may be substituted by 1 or 2 substituents" is two, those substituents may be the same as or different from one another.

The "cyclic amino" of the above-mentioned (2) "cyclic amino which may be substituted" includes, for example, 5- to 7-membered non-aromatic cyclic amino optionally containing 1 to 4 hetero atoms selected from the group consisting of nitrogen, sulfur and oxygen atoms in addition to carbon atoms and at least one nitrogen atom, such as pyrrolidin-1-yl, piperidino, piperazin-1-yl, morpholino, thiomorpholino, tetrahydroazepin-1-yl, imidazolidin-1-yl, 2,3-dihydro-1H-imidazol-1-yl, tetrahydro-1(2H)-pyrimidinyl, 3,6-dihydro-1(2H)-pyrimidinyl, 3,4-dihydro-1(2H)-pyrimidinyl, etc. The "substituents" of the "cyclic amino which may be substituted" include, for example, 1 to 3 of the "substituents" of the "5- to 7-membered saturated cyclic amino which may be substituted" described in detail in the foregoing referring to the "substituents" of the "hydrocarbon group which may be substituted" for $R^5$.

Examples of the 5- to 7-membered non-aromatic cyclic amino substituted by an oxo are 2-oxoimidazolidin-1-yl, 2-oxo-2,3-dihydro-1H-imidazol-1-yl, 2-oxotetrahydro-1(2H)-pyrimidinyl, 2-oxo-3,6-dihydro-1(2H)-pyrimidinyl, 2-oxo-3,4-dihydro-1(2H)-pyrimidinyl, etc.

Preferable example of compound (I) is compound (Ia).

The ring-constituting nitrogen atom in the 1,3-azole in compound (Ia) may be oxidized (N-oxidized).

The "hydrocarbon group which may be substituted" the "heterocyclic group which may be substituted" and the "amino which may be substituted" for $R^1$, include, for example, the "hydrocarbon group which may be substituted" the "heterocyclic group which may be substituted" and the "amino which may be substituted" which the above compound (I) may have, respectively.

$R^1$ is preferably an amino which may be substituted. More preferred is an amino which may be substituted by 1 or 2 acyl of the formula: $-(C{=}O)-R^5$, $-(C{=}O)-OR^5$, $-(C{=}O)-NR^5R^6$, $-(C{=}S)-NHR^5$ or $-SO_2-R^7$ (more preferably, $-(C{=}O)-R^5$ or $-(C{=}O)-NR^5R^6$) wherein each symbol is as defined above. Among others, especially preferred is a 5- to 7-membered non-aromatic cyclic amino optionally containing 1 to 4 hetero atoms selected from the group consisting of nitrogen, sulfur and oxygen atoms in addition to carbon atoms and at least one nitrogen atom, which may be substituted by 1 to 3 substituents selected from the group consisting of $C_{1-6}$ alkyl, $C_{6-14}$ aryl, $C_{1-6}$ alkyl-carbonyl, 5- to 10-membered aromatic heterocyclic group and oxo.

The "pyridyl which may be substituted" for $R^2$ or $R^3$ includes, for example, the "pyridyl which may be substituted" which the above compound (I) has.

The "aromatic hydrocarbon group" of the "aromatic hydrocarbon group which may be substituted" for $R^2$ or $R^3$ includes, for example, a $C_{6-14}$ monocyclic or fused polycyclic (e.g., bi- or tri-cyclic) aromatic hydrocarbon group, etc. Concretely mentioned is $C_{6-14}$ aryl such as phenyl, 1-naphthyl, 2-naphthyl, 2-biphenylyl, 3-biphenylyl, 4-biphenylyl, 2-anthryl, etc.

The "substituents" of the "aromatic hydrocarbon group which may be substituted" include, for example, the same as those mentioned above for the "substituents" of the "hydrocarbon group which may be substituted" for $R^5$. The number of such substituent is 1 to 5, preferably 1 to 3. When the number of substituents is two or more, those substituents may be the same as or different from one another. The two substituents (preferably alkyl groups) can form, together with a neighboring substituent, a 4- to 7-membered (preferably, 5-membered) non-aromatic carbocyclic ring.

It is preferred that at least one of $R^2$ and $R^3$ is a pyridyl which may be substituted or an aromatic hydrocarbon group which may be substituted, and the other is a pyridyl which may be substituted.

$R^2$ is preferably a pyridyl which may be substituted.

$R^3$ is preferably a $C_{6-14}$ (preferably $C_{6-10}$) aryl which may be substituted.

The "sulfur atom which may be oxidized" for X includes S, SO and $SO_2$.

The "hydrocarbon group which may be substituted" for $R^4$ includes, for example, the "hydrocarbon group which may be substituted" for $R^5$ above.

X is preferably a sulfur atom which may be oxidized. More preferred is S.

In compound (Ia), preferred is a compound wherein $R^1$ is an amino which may be substituted, preferably a monoacylamino;

at least one of $R^2$ and $R^3$ is a pyridyl which may be substituted or an aromatic hydrocarbon group which may be substituted, and the other is a pyridyl which may be substituted; and X is S.

More preferred is a compound wherein $R^1$ is an amino which may be substituted by 1 or 2 acyl of the formula: $-(C{=}O)-R^5$ or $-(C{=}O)-NR^5R^6$ wherein each symbol is as defined above;

$R^2$ is a pyridyl which may be substituted by 1 to 5 $C_{1-6}$ alkyl;

$R^3$ is a $C_{6-14}$ aryl which may be substituted by 1 to 5 substituents selected from the group consisting of halogen atoms, optionally halogenated $C_{1-6}$ alkyl, optionally halogenated $C_{1-6}$ alkoxy and carboxy; and X is S.

Another preferred example is a compound, wherein $R^1$ is (i) a $C_{1-8}$ alkyl; $C_{3-6}$ cycloalkyl or $C_{6-14}$ aryl group which may be substituted by 1 to 5 substituents selected from the group consisting of halogen atoms, optionally halogenated $C_{1-6}$ alkyl, carboxy $C_{2-6}$ alkenyl, optionally halogenated $C_{1-6}$ alkoxy, $C_{1-6}$ alkoxy-carbonyl-$C_{1-6}$ alkoxy, hydroxy, amino, mono-$C_{1-6}$ alkylamino, carboxy, $C_{1-6}$ alkoxy-carbonyl, mono-$C_{1-6}$ alkyl-carbamoyl and $C_{6-14}$ aryl-carbonylamino, (ii) a 5-membered heterocyclic group, (iii) an amino which may be substituted by 1 or 2 substituents selected from the group consisting of (1) $C_{1-6}$ alkyl,(2) $C_{6-14}$ aryl, (3) $C_{7-16}$ aralkyl, (4) 6-membered heterocyclic group, (5) a $C_{1-6}$ alkyl-carbonyl, $C_{3-6}$ cycloalkyl-carbonyl, $C_{6-14}$ aryl-carbonyl, $C_{7-16}$ aralkyl-carbonyl, $C_{1-6}$ alkyl-carbamoyl or 5- or 6-membered heterocycle carbonyl group which may be substituted by 1 to 3 substituents selected from the group consisting of halogen atoms, $C_{1-6}$ alkyl, $C_{1-6}$ alkoxy, carboxy and $C_{1-6}$ alkoxy-carbonyl, and (6) di-$C_{1-6}$ alkylamino-$C_{1-6}$ alkylidene, (iv) a 5- or 6-membered non-aromatic cyclic amino which may be substituted by $C_{1-6}$ alkyl-carbonyl or oxo, or (v) carboxy;

$R^2$ is a pyridyl which may be substituted by 1 to 3 $C_{1-6}$ alkyl;

$R^3$ is a $C_{6-10}$ aryl which may be substituted by 1 to 3 substituents selected from the group consisting of halogen atoms, $C_{1-3}$ alkylenedioxy, optionally halogenated $C_{1-6}$ alkyl, carboxy $C_{2-6}$ alkenyl, optionally halogenated $C_{1-8}$ alkoxy, hydroxy, $C_{7-16}$ aralkyloxy and $C_{1-6}$ alkyl-carbonyloxy, and the alkyl group can form, together with the neighboring alkyl group, a 5-membered non-aromatic carbocyclic ring; and X is S.

More preferred examples of compound (Ia) are

N-[4-(4-methoxyphenyl)-5-(3-pyridyl)-1,3-thiazol-2-yl]acetamide,

N-[4-(4-methoxyphenyl)-5-(4-pyridyl)-1,3-thiazol-2-yl]acetamide,

N-[4-(4-methoxyphenyl)-5-(4-pyridyl)-1,3-thiazol-2-yl]propionamide,

N-[4-(4-methoxyphenyl)-5-(4-pyridyl)-1,3-thiazol-2-yl]-2-methylpropionamide,

N-[4-(4-methoxyphenyl)-5-(4-pyridyl)-1,3-thiazol-2-yl]butyramide,

N-[4-(4-methoxyphenyl)-5-(4-pyridyl)-1,3-thiazol-2-yl]benzamide,

N-[4-(4-methoxyphenyl)-5-(4-pyridyl)-1,3-thiazol-2-yl]nicotinamide,

N-[4-(4-methoxyphenyl)-5-(4-pyridyl)-1,3-thiazol-2-yl]-N'-ethylurea,

N-(4-(4-methoxyphenyl)-5-(4-pyridyl)-1,3-thiazol-2-yl]-N'-propylurea, 4-(4-methoxyphenyl)-2-(2-oxoimidazolidin-1-yl)-5-(4-pyridyl)-1,3-thiazole, 4-(4-methoxyphenyl)-2-(2-oxo-2,3-dihydro-1H-imidazol-1-yl)-5-(4-pyridyl)-1,3-thiazole, 4-(4-methoxyphenyl)-2-[2-oxotetrahydro-1(2H)-pyrimidinyl)-5-(4-pyridyl)-1,3-thiazole, 4-(4-methoxyphenyl)-2-(2-oxopyrrolidin-1-yl)-5-(4-pyridyl)-1,3-thiazole, N-[4-(4-ethylphenyl)-5-(4-pyridyl)-1,3-thiazol- 2-yl]acetamide, N-[4-(4-ethylphenyl)-5-(4-pyridyl)-1,3-thiazol-2-yl]propionamide, N-[4-[4-(1,1-dimethylethyl)phenyl]-5-(3-pyridyl)-1,3-thiazol-2-yl]acetamide, N-[4-[4-(1,1-dimethylethyl)phenyl]-5-(4-pyridyl)-1,3-thiazol-2-yl]acetamide, N-[4-[4-(1,1-dimethylethyl)phenyl]-5-(4-pyridyl)-1,3-thiazol-2-yl]propionamide, N-[4-[4-(1,1-dimethylethyl)phenyl]-5-(4-pyridyl)-1,3-thiazol-2-yl]-2-methylpropionamide, N-[4-[4-(1,1-dimethylethyl)phenyl]-5-(4-pyridyl)-1,3-thiazol-2-yl]butyramide, N-[4-[4-(1,1-dimethylethyl)phenyl]-5-(4-pyridyl)-1,3-thiazol-2-yl]benzamide, N-[4-[4-(1,1-dimethylethyl)phenyl]-5-(4-pyridyl)-1,3-thiazol-2-yl]nicotinamide, N-[4-[4-(1,1-dimethylethyl)phenyl]-5-(4-pyridyl)-1,3-thiazol-2-yl]-N'-ethylurea, N-[4-[4-(1,1-dimethylethyl)phenyl]-5-(4-pyridyl)-1,3-thiazol-2-yl]-N'-propylurea, 4-[4-(1,1-dimethylethyl)phenyl]-2-(2-oxoimidazolidin-1-yl)-5-(4-pyridyl)-1,3-thiazole, 4-[4-(1,1-dimethylethyl)phenyl]-2-(2-oxo-2,3-dihydro-1H-imidazol-1-yl)-5-(4-pyridyl)-1,3-thiazole, 4-[4-(1,1-dimethylethyl)phenyl]-2-[2-oxotetrahydro-1(2H)-pyrimidinyl]-5-(4-pyridyl)-1,3-thiazole, 4-[4-(1,1-dimethylethyl)phenyl]-2-(2-oxopyrrolidin-1-yl)-5-(4-pyridyl)-1,3-thiazole, N-[4-(3,5-dimethylphenyl)-5-(3-pyridyl)-1,3-thiazol-2-yl]acetamide, N-[4-(3,5-dimethylphenyl)-5-(4-pyridyl)-1,3-thiazol-2-yl]acetamide, N-[4-(3,5-dimethylphenyl)-5-(4-pyridyl)-1,3-thiazol-2-yl]propionamide, N-[4-(3,5-dimethylphenyl)-5-(4-pyridyl)-1,3-thiazol-2-yl]-2 -methylpropionamide, N-[4-(3,5-dimethylphenyl)-5-(4-pyridyl)-1,3-thiazol-2-yl]butyramide, N-[4-(3,5-dimethylphenyl)-5-(4-pyridyl)-1,3-thiazol-2-yl]benzamide, N-[4-(3,5-dimethylphenyl)-5-(4-pyridyl)-1,3-thiazol-2-yl]nicotinamide, N-[4-(3,5-dimethylphenyl)-5-(4-pyridyl)-1,3-thiazol-2-yl]-N'-ethylurea, N-[4-(3,5-dimethylphenyl)-5-(4-pyridyl)-1,3-thiazol-2-yl]-N'-propylurea, 4-(3,5-dimethylphenyl)-2-(2-oxoimidazolidin-1-yl)-5-(4-pyridyl)-1,3-thiazole, 4-(3,5-dimethylphenyl)-2-(2-oxo-2,3-dihydro-1H-imidazol-1-yl)-5-(4-pyridyl)-1,3-thiazole, 4-(3,5-dimethylphenyl)-2-[2-oxotetrahydro-1(2H)-pyrimidinyl]-5-(4-pyridyl)-1,3-thiazole, 4-(3,5-dimethylphenyl)-2-(2-oxopyrrolidin-1-yl)-5-(4-pyridyl)-1,3-thiazole, N-[5-(4-pyridyl)-4-(4-trifluoromethylphenyl)-1,3-thiazol-2-yl]acetamide, N-[5-(4-pyridyl)-4-(4-trifluoromethylphenyl)-1,3-thiazol-2-yl]propionamide, N-[5-(4-pyridyl)-4-(4-trifluoromethylphenyl)-1,3-thiazol-2-yl]-2-methylpropionamide, N-[5-(4-pyridyl)-4-(4-trifluoromethylphenyl)-1,3-thiazol-2-yl]benzamide, N-[5-(4-pyridyl)-4-(4-trifluoromethylphenyl)-1,3-thiazol-2-yl]nicotinamide, N-[5-(4-pyridyl)-4-(4-trifluoromethylphenyl)-1,3-thiazol-2-yl]-N'-ethylurea, N-[5-(4-pyridyl)-4-(4-trifluoromethylphenyl)-1,3-thiazol-2-yl]-N'-propylurea, salts thereof, and so forth.

In compound (Ia), compound (Ib) is novel compound.

The "aromatic heterocyclic group" of the "aromatic heterocyclic group which may be substituted" for $R^{1a}$includes, for example, a monovalent group formed by removing an optional hydrogen atom from a 5- to 14-membered preferably 5- to 10-membered (monocyclic, bicyclic or tricyclic) aromatic heterocyclic ring containing 1 to 4 hetero atoms of 1 or 2 species selected from the group consisting of nitrogen, sulfur and oxygen atoms in addition to carbon atoms, etc. Concretely mentioned are a monovalent group formed by removing an optional hydrogen atom from an aromatic heterocyclic ring such as thiophene, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, 1H-indazole, purine, 4H-quinolidine, isoquinoline, quinoline, phthalazine, naphthyridine, quinoxaline, quinazoline, cinnoline, carbazole, β-carboline, phenanthridine, acridine, phenazine, isothiazole, phenothiazine, isoxazole, furazan, phenoxazine, etc.; and a ring as formed through condensation of those rings, preferably a monocyclic ring, with one or more, preferably one or two aromatic rings (e.g., benzene ring, etc.), etc.

The preferred example of the "aromatic heterocyclic group" is a 5- or 6-membered aromatic heterocyclic group which may be fused with one benzene ring. Concretely mentioned are 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isoxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc. More preferred are 2-thienyl, 3-thienyl, 2-pyridyl, 3-pyridyl, 4-pyridyl, 2-quinolyl, 3-quinolyl, 1-isoquinolyl, 1-indolyl, 2-benzothiazolyl, etc.

The "substituents" of the "aromatic heterocyclic group which may be substituted" and their number are the same as those mentioned above for the "substituents" of the "hydrocarbon group which may be substituted" for $R^5$.

The "amino" of the "amino which may be substituted by substituent(s) selected from the group consisting of a substituted carbonyl and a hydrocarbon group which may be substituted" for $R^{1a}$ includes an amino which may be substituted by 1 or 2 substituents selected from the group consisting of a substituted carbonyl and a hydrocarbon group which may be substituted. When the number of substituents is two, those substituents may be the same as or different from one another.

The "substituted carbonyl" of the "amino which may be substituted by substituent(s) selected from the group consisting of a substituted carbonyl and a hydrocarbon group which may be substituted" includes, for example, a group of the formula: $-(C{=}O)-R^{5a}$, $-(C{=}O)\ OR^{5a}$ or $-(C{=}O)-NR^{Ra}R^{6a}$ wherein $R^{5a}$ represents a hydrogen atom, a hydrocarbon group which may be substituted or a heterocyclic group which may be substituted, and $R^{6a}$ represents a hydrogen atom or a $C_{1-6}$ alkyl.

The "hydrocarbon group which may be substituted" and the "heterocyclic group which may be substituted" for $R^{5a}$ include, for example, the "hydrocarbon group which may be substituted" and the "heterocyclic group which may be substituted" for $R^5$ above, respectively.

The "$C_{1-6}$ alkyl" for $R^{6a}$ includes, for example, the "$C_{1-6}$ alkyl" for $R^6$ above.

The examples of the "substituted carbonyl" are formyl carboxy, $C_{1-6}$ alkyl-carbonyl (e.g., acetyl, propionyl, etc.), $C_{3-6}$ cycloalkyl-carbonyl (e.g., cyclopropylcarbonyl, cyclopentylcarbonyl, cyclohexylcarbonyl, etc.), $C_{1-6}$ alkoxy-carbonyl (e.g., methoxycarbonyl, ethoxycarbonyl, propoxycarbonyl, tert-butoxycarbonyl, etc.), $C_{6-14}$ aryl-carbonyl (e.g., benzoyl, 1-naphthoyl, 2-naphthoyl, etc.), $C_{7-16}$ aralkyl-carbonyl (e.g., phenylacetyl, 3-phenylpropionyl, etc.), $C_{6-14}$ aryloxy-carbonyl (e.g., phenoxycarbonyl, etc.), $C_{7-16}$ aralkyloxy-carbonyl (e.g., benzyloxycarbonyl, phenethyloxycarbonyl, etc.), 5- or 6-membered heterocycle carbonyl (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl, etc.), carbamoyl, mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), $C_{6-14}$ aryl-carbamoyl (e.g., phenylcarbamoyl, 1-naphthylcarbamoyl, 2-naphthylcarbamoyl, etc.), 5- or 6-membered heterocycle carbamoyl (e.g., 2-pyridylcarbamoyl, 3-pyridylcarbamoyl, 4-pyridylcarbamoyl, 2-thienylcarbamoyl, 3-thienylcarbamoyl, etc.), etc.

The "hydrocarbon group which may be substituted" of the "amino which may be substituted by substituent(s) selected from the group consisting of a substituted carbonyl and a hydrocarbon group which may be substituted" for $R^{1a}$ includes, for example, the "hydrocarbon group which may be substituted" for $R^5$.

The "cyclic amino which may be substituted" for $R^{1a}$ includes, for example, the "cyclic amino which may be substituted" described in the "amino which may be substituted" for $R^1$.

$R^{1a}$ is preferably an amino which may be substituted by substituent(s) selected from the group consisting of a substituted carbonyl and a hydrocarbon group which may be substituted.

The "aromatic hydrocarbon group which may be substituted" for $R^{2a}$ includes, for example, the "aromatic hydrocarbon group which may be substituted" for $R^2$ or $R^3$ above.

The "pyridyl which may be substituted" for $R^{3a}$ includes, for example, the "pyridyl which may be substituted" which the above compound (I) has.

Preferred example of compound (Ib) is a compound wherein $R^{1a}$ is an amino which may be substituted by 1 or 2 substituents selected from the group consisting of $C_{1-6}$ alkyl, $C_{1-6}$ alkyl-carbonyl, $C_{6-14}$ aryl-carbonyl and $C_{1-6}$ alkyl-carbamoyl;

$R^{2a}$ is a phenyl which may be substituted by 1 to 3 substituents selected from the group consisting of halogen atoms, optionally halogenated $C_{1-6}$ alkyl and optionally halogenated $C_{1-6}$ alkoxy; and $R^{3a}$ is a pyridyl.

The examples of compound (Ib) are

N-methyl[5-phenyl-4-(3-pyridyl)-1,3-thiazol-2-yl]amine,

[5-phenyl-4-(3-pyridyl)thiazol-2-yl]amine,

N-[5-phenyl-4-(3-pyridyl)thiazol-2-yl]acetoamide,

N-[5-[4-(1,1-dimethylethyl)phenyl)-4-(4-pyridyl)-1,3-thiazol-2-yl]acetamide,

N-[5-[4-(1,1-dimethylethyl)phenyl]-4-(4-pyridyl)-1,3-thiazol-2-yl]propionamide,

N-[5-[4-(1,1-dimethylethyl)phenyl]-4-(4-pyridyl)-1,3-thiazol-2-yl]nicotinamide,

N-[5-(3,5-dimethylphenyl)-4-(4-pyridyl)-1,3-thiazol-2-yl]acetamide,

N-[5-(3,5-dimethylphenyl)-4-(4-pyridyl)-1,3-thiazol-2-yl]propionamide,

N-[5-(3,5-dimethylphenyl)-4-(4-pyridyl)-1,3-thiazol-2-yl]nicotinamide, salts thereof, and so forth.

A novel compound of the formula:

(Ic)

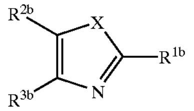

wherein $R^{1b}$ represents a hydrogen atom, a hydrocarbon group which may be substituted, a heterocyclic group which may be substituted, an amino which may be substituted or an acyl;

$R^{2b}$ represents a N-oxidized pyridyl which may be substituted; and $R^{3b}$ represents a hydrogen atom, a pyridyl which may be substituted or an aromatic hydrocarbon group which may be substituted; or a salt thereof, [hereinafter sometimes referred to briefly as compound (Ic)] is also within a scope of compound (Ia).

The "hydrocarbon group which may be substituted" the "heterocyclic group which may be substituted" the "amino which may be substituted" and the "acyl" for $R^{1b}$ include, for example, the "hydrocarbon group which may be substituted" the "heterocyclic group which may be substituted" the "amino which may be substituted" and the "acyl" for $R^1$ above, respectively.

$R^{1b}$ is preferably an amino which may be substituted. More preferred is an amino which may be substituted by 1 or 2 acyl of the formula: $-(C{=}O)-R^5$, $-(C{=}O)-OR^5$, $-(C{=}O)-NR^5R^6$, $-(C{=}S)-NHR^5$ or $-SO_2-R^7$ (more preferably, $-(C{=}O)-R^5$ or $-(C{=}O)-NR^5R^6$) wherein each symbol is as defined above.

The "substituents" of the "N-oxidized pyridyl which may be substituted" are the same as those mentioned above for the "substituents" of the "hydrocarbon group which may be substituted" for $R^5$ above. The "N-oxidized pyridyl" may have 1 to 4, preferably 1 to 3 substituents as mentioned above at possible positions of the pyridyl and, when the number of substituents is two or more, those substituents may be the same as or different from one another.

The "pyridyl which may be substituted" and the "aromatic hydrocarbon group which may be substituted" for $R^{3b}$ include, for example, the "pyridyl which may be substituted" and the "aromatic hydrocarbon group which may be substituted" for $R^3$ above, respectively.

$R^{3b}$ is preferably a $C_{6-14}$ (preferably $C_{6-10}$) aryl which may be substituted.

A perferred example of compound (Ic) is a compound wherein $R^{1b}$ is an amino which may be substituted by 1 or 2 acyl of the formula: $-(C{=}O)-R^5$ or $-(C{=}O)-NR^5R^6$ wherein each symbol is as defined above;

$R^{2b}$ is a N-oxidized pyridyl which may be substituted by 1 to 3 $C_{1-6}$ alkyl; and $R^{3b}$ is a $C_{6-10}$ aryl which may be substituted by 1 to 5 substituents selected from the group consisting of halogen atoms, optionally halogenated $C_{1-6}$ alkyl, optionally halogenated $C_{1-6}$ alkoxy and carboxy.

The examples of compound (Ic) are

3-[2-acetylamino-4-(4-methoxyphenyl)-1,3-thiazol-5-yl]pyridine 1-oxide,

4-[2-acetylamino-4-(4-methoxyphenyl)-1,3-thiazol-5-yl]pyridine 1-oxide,

4-[4-(4-methoxyphenyl)-2-propionylamino-1,3-thiazol-5-yl]pyridine 1-oxide,

4-[4-(4-methoxyphenyl)-2-(2-methylpropionyl)amino-1,3-thiazol-5-yl]pyridine 1-oxide, 4-[2-butyrylamino-4-(4-methoxyphenyl)-1,3-thiazol-5-yl]pyridine 1-oxide, 4-[2-benzoylamino-4-(4-methoxyphenyl)-1,3-thiazol-5-yl]pyridine 1-oxide, 4-[4-(4-methoxyphenyl)-2-nicotinoylamino-1,3-thiazol-5-yl]pyridine 1-oxide, 4-[2-(N'-ethylureido)-4-(4-methoxyphenyl)-1,3-thiazol-5-yl]pyridine 1-oxide, 4-[4-(4-methoxyphenyl)-2-(N'-propylureido)-1,3-thiazol-5-yl]pyridine 1-oxide, 4-[2-acetylamino-4-(4-ethylphenyl)-1,3-thiazol-5-yl]pyridine 1-oxide, 4-[4-(4-ethylphenyl)-2-propionylamino-1,3-thiazol-5-yl]pyridine 1-oxide, 3-[2-acetylamino-4-[4-(1,1-dimethylethyl)phenyl]-1,3-thiazol-5-yl]pyridine 1-oxide, 4-[2-acetylamino-4-[4-(1,1-dimethylethyl)phenyl]-1,3-thiazol-5-yl]pyridine 1-oxide, 4-[4-[4-(1,1-dimethylethyl)phenyl]-2-propionylamino-1,3-thiazol-5-yl]pyridine 1-oxide, 4-[4-[4-(1,1-dimethylethyl)phenyl]-2-(2-methylpropionyl)amino-1,3-thiazol-5-yl]pyridine 1-oxide, 4-[2-butyrylamino-4-[4-(1,1-dimethylethyl)phenyl]-1,3-thiazol-5-yl]pyridine 1-oxide, 4-[2-benzoylamino-4-[4-(1,1-dimethylethyl)phenyl]-1,3-thiazol-5-yl]pyridine 1-oxide, 4-[4-[4-(1,1-dimethylethyl)phenyl]-2-nicotinoylamino-1,3-thiazol-5-yl]pyridine 1-oxide, 4-[4-[4-(1,1-dimethylethyl)phenyl]-2-(N'-ethylureido)-1,3-thiazol-5-yl]pyridine 1-oxide, 4-[4-4-(1,1-dimethylethyl)phenyl]-2-(N'-propylureido)-1,3-thiazol-5-yl]pyridine 1-oxide, 3-[2-acetylamino-4-(3,5-dimethylphenyl)-1,3-thiazol-5-yl]pyridine 1-oxide, 4-[2-acetylamino-4-(3,5-dimethylphenyl)-1,3-thiazol-5-yl]pyridine 1-oxide, 4-[4-(3,5-dimethylphenyl)-2-propionylamino-1,3-thiazol-5-yl]pyridine 1-oxide, 4-[4-(3,5-dimethylphenyl)-2-(2-methylpropionyl)amino-1,3-thiazol-5-yl]pyridine 1-oxide, 4-[2-butyrylamino-4-(3,5-dimethylphenyl)-1,3-thiazol-5-yl]pyridine 1-oxide, 4-[2-benzoylamino-4-(3,5-dimethylphenyl)-1,3-thiazol-5-yl]pyridine 1-oxide, 4-[4-(3,5-dimethylphenyl)-2-nicotinoylamino-1,3-thiazol-5-yl]pyridine 1-oxide, 4-[4-(3,5-dimethylphenyl)-2-(N'-ethylureido)-1,3-thiazol-5-yl]pyridine 1-oxide, 4-(4-(3,5-dimethylphenyl)-2-(N'-propylureido)-1,3-thiazol-5-yl]pyridine 1-oxide, 4-[2-acetylamino-4-(4-trifluoromethylphenyl)-1,3-thiazol-5-yl]pyridine 1-oxide, 4-[2-propionylamino-4-(4-trifluoromethylphenyl)-1,3-thiazol-5-yl]pyridine 1-oxide, 4-[2-(2-methylpropionyl)amino-4-(4-trifluoromethylphenyl)-1,3-thiazol-5-yl]pyridine 1-oxide, 4-[2-butyrylamino-4-(4-trifluoromethylphenyl)-1,3-thiazol-5-yl]pyridine 1-oxide, 4-[2-benzoylamino-4-(4-trifluoromethylphenyl)-1,3-thiazol-5-yl]pyridine 1-oxide, 4-[2-nicotionylamino-4-(4-trifluoromethylphenyl)-1,3-thiazol-5-yl]pyridine 1-oxide, 4-[2-(N'-ethylureido)-4-(4-trifluoromethylphenyl)-1,3-thiazol-5-yl]pyridine 1-oxide, 4-[2-(N'-propylureido)-4-(4-trifluoromethylphenyl)-1,3-thiazol-5-yl]pyridine 1-oxide, and so forth.

Salts of compound (I), compound (Ia), compound (Ib) or compound (Ic) include, for example, metal salts, ammonium salts, salts with organic bases, salts with inorganic acids, salts with organic acids, salts with basic or acidic amino acids, etc. Preferred examples of metal salts include alkali metal salts such as sodium salts, potassium salts; alkaline earth metal salts such as calcium salts, magnesium salts, barium salts; aluminium salts, etc. Preferred examples of salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Preferred examples of salts with inorganic acids include hydrochlorides, hydrobromides, nitrates, sulfates, phosphates, etc. Preferred examples of salts with organic acids include formates, acetates, trifluoroacetates, fumarates, oxalates, tartrates, maleates, citrates, succinates, malates, methanesulfonates, benzenesulfonates, p-toluenesulfonates, etc. Preferred examples of salts with basic amino acids include salts with arginine, lysine, ornithine, etc. Preferred examples of salts with acidic amino acids include aspartates, glutamates, etc.

Among others, more preferred are pharmaceutically acceptable salts. For example, for the compound having an acidic functional group in the molecule, mentioned are their inorganic salts, such as alkali metal salts (e.g., sodium salts, potassium salts, etc.), and alkaline earth metal salts (e.g., calcium salts, magnesium salts, barium salts, etc.), ammonium salts, etc.; and for the compound having a basic functional group in the molecule, mentioned are their inorganic salts such as hydrobromides, nitrates, sulfates, phosphates, etc., and organic salts such as acetates maleates, fumarates, succinates, citrates, tartrates, methanesulfonates, p-toluenesulfonates, etc.

Process for producing compound (I) (including compounds (Ia), (Ib) and (Ic)) is mentioned below.

Compound (I) can be produced in any per se known manner, for example, according to the methods of the following processes 1 to 3 or analogous methods thereto as well as the methods disclosed in WO 95/13067 or analogous methods thereto in case that compound (I) is 1,3-oxazole compounds, the methods disclosed in U.S. Pat. No. 3,940,486, WO 88/01169, WO 93/14081, WO 95/02591, WO 97/12876 or analogous methods thereto in case that compound (I) is 1,3-imidazole compounds, and the methods disclosed in JP-A-60-58981, JP-A-61-10580, JP-A-7-503023, WO 93/15071, DE-A-3601411, JP-A-5-70446 or analogous methods thereto in case that compound (I) is 1,3-thiazole.

Each symbol in the compounds in the following processes 1 to 3 is same as defined above. The compounds described in the following processes include their salts. For their salts, for example, referred to are the same as the salts of compound (I).

Process 1

Process 1

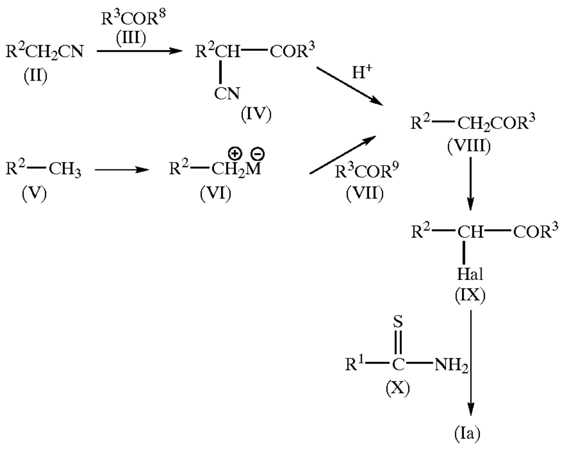

Compounds (II), (III), (V), (VII), (XI), (XIII) and (XIV) may be purchased from commercial sources if they are available on the market or can be produced in any per se known manner.

Compound (IV) is produced by subjecting compound (II) to condensation with compound (III) in the presence of a base.

In compound (III), $R^8$ represents, for example, (i) $C_{1-6}$ alkoxy (e.g., methoxy, ethoxy, etc.), (ii) di-$C_{1-6}$ alkylamino (e.g., dimethylamino, diethylamino, etc.), (iii) N-$C_{6-10}$ aryl-N-$C_{1-6}$ alkylamino (e.g., N-phenyl-N-methylamino, etc.), (iv) 3- to 7-membered cyclic amino 15 (e.g., pyrrolidino, morpholino, methylaziridin-1-yl, etc.) which may be substituted by $C_{6-10}$ aryl and/or $C_{1-6}$ alkyl, etc.

The amount of compound (III) to be used is 0.5 to 3.0 mols or so, preferably 0.8 to 2.0 mols or so, relative to one mol of compound (II).

The amount of the base to be used is 1.0 to 30 mols or so, preferably 1.0 to 10 mols or so, relative to one mol of compound (II).

The "base" includes, for example, basic salts such as sodium carbonate, potassium carbonate, cesium carbonate, etc.; inorganic bases such as sodium hydroxide, potassium hydroxide, etc.; aromatic amines such aspyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc.

This reaction is advantageously carried out in the absence of a solvent or in an inert solvent. There is no particular limitation on the kind of solvent that can be used unless the reaction is interfered with. Preferred are halogenated hydrocarbons, aliphatic hydrocarbons, aromatic hydrocarbons, ethers, amides, alcohols, water, and mixtures of those solvents.

The reaction temperature is generally −5 to 200° C. or so, preferably 5 to 150° C. or so. The reaction time is generally about 5 minutes to 72 hours, preferably about 0.5 to 30 hours.

The product as produced in the manner mentioned above may be applied to the next reaction while it is still crude in the reaction mixture, or may be isolated from the reaction mixture in any ordinary manner. This can be easily purified through separation means such as recrystallization, distillation, chromatography and the like.

Compound (VIII) is produced by treating compound (IV) with an acid.

The amount of the acid to be used is 1.0 to 100 mols or so, preferably 1.0 to 30 mols or so, relative to one mol of compound (IV).

The "acids" include, for example, mineral acids such as hydrochloric acid, hydrobromic acid, sulfuric acid, etc.

This reaction is advantageously carried out in an inert solvent. There is no particular limitation on the kind of solvent that can be used unless the reaction is interfered with. Preferred are water, mixtures of water and amides, mixtures of water and alcohols, etc.

The reaction temperature is generally 20 to 200° C. or so, preferably 60 to 150° C. or so. The reaction time is generally about 30 minutes to 72 hours, preferably about 1 to 30 hours.

The product as produced in the manner mentioned above may be applied to the next reaction while it is still crude in the reaction mixture, or may be isolated from the reaction mixture in any ordinary manner. This can be easily purified through separation means such as recrystallization, distillation, chromatography and the like.

Compound (VIII) is also produced by treating compound (V) with a base followed by subjecting the resultant compound (VI) to condensation with compound (VII).

In compound (VI), M represents, for example, an alkali metal such as lithium, sodium, potassium, etc.

In compound (VII), $R^9$ represents, for example, same as those mentioned above for $R^8$.

The amount of the base to be used is 1.0 to 30 mols or so, preferably 1.0 to 10 mols or so, relative to one mol of compound (V).

The "base" includes, for example, metal amides such as sodium amide, lithium diisopropylamide, lithium hexamethyldisilazide, etc.

This reaction is advantageously carried out in the absence of a solvent or in an inert solvent. There is no particular limitation on the kind of solvent that can be used unless the reaction is interfered with. Preferred are aliphatic hydrocarbons, aromatic. hydrocarbons, ethers, and mixtures of those solvents.

The reaction temperature is generally −78 to 60° C. or so, preferably −78 to 20° C. or so. The reaction time is generally about 5 minutes to 24 hours, preferably about 0.5 to 3 hours.

The product as produced in the manner mentioned above may be applied to the next reaction while it is still crude in the reaction mixture, or may be isolated from the reaction mixture in any ordinary manner. This can be easily purified through separation means such as recrystallization, distillation, chromatography and the like.

Compound (IX) is produced by treating compound (VIII) with a halogen. If desired, this reaction is carried out in the presence of a base or a basic salt.

The amount of the halogen to be used is 1.0 to 5.0 mols or so, preferably 1.0 to 2.0 mols or so, relative to one mol of compound (VIII).

The "halogen" includes, for example, bromine, chlorine, iodine, etc.

The amount of the base to be used is 1.0 to 10.0 mols or so, preferably 1.0 to 3.0 mols or so, relative to one mol of compound (VIII).

The "base" includes, for example, aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.

The amount of the basic salt to be used is 1.0 to 10.0 mols or so, preferably 1.0 to 3.0 mols or so, relative to one mol of compound (VIII).

The "basic salt" includes, for example, sodium carbonate, potassium carbonate, cesium carbonate, sodium hydrogencarbonate, sodium acetate, potassium acetate, etc.

This reaction is advantageously carried out in the absence of a solvent or in an inert solvent. There is no particular limitation on the kind of solvent that can be used unless the reaction is interfered with. Preferred are ethers, aromatic hydrocarbons, aliphatic hydrocarbons, amides, halogenated hydrocarbons, nitrites, sulfoxides, organic acids, aromatic amines and mixtures of those solvents.

The reaction temperature is −20 to 150° C. or so, preferably 0 to 100° C. or so. The reaction time is generally 5 minutes to 24 hours, preferably about 10 minutes to 5 hours.

The product as produced in the manner mentioned above may be applied to the next reaction while it is still crude in the reaction mixture, or may be isolated from the reaction mixture in any ordinary manner. This can be easily purified through separation means such as recrystallization, distillation, chromatography and the like.

Compound (Ia) is produced by subjecting compound (IX) to condensation with compound (X). If desired, this reaction is carried out in the presence of a base or a basic salt.

In compound (IX), Hal represents halogens.

Compound (X) may be purchased from commercial sources if they are available on the market or can be produced according to any per se known methods or analogous methods thereto as well as the methods disclosed in the following process 2.

The amount of compound (X) to be used is 0.5 to 3.0 mols or so, preferably 0.8 to 2.0 mols or so, relative to one mol of compound (IX).

The amount of the base to be used is 1.0 to 30 mols or so, preferably 1.0 to 10 mols or so, relative to one mol of compound (IX).

The "base" includes, for example, basic salts such as sodium carbonate, potassium carbonate, cesium carbonate, sodium hydrogencarbonate, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.

This reaction is advantageously carried out in the absence of a solvent or in an inert solvent. There is no particular limitation on the kind of solvent that can be used unless the reaction is interfered with. Preferred are halogenated hydrocarbons, aliphatic hydrocarbons, aromatic hydrocarbons, ethers, amides, alcohols, nitrites and mixtures of those solvents.

The reaction temperature is −5 to 200° C. or so, preferably 5 to 150° C. or so. The reaction time is generally 5 minutes to 72 hours, preferably about 0.5 to 30 hours.

The product as produced in the manner mentioned above may be applied to the next reaction while it is still crude in the reaction mixture, or may be isolated from the reaction mixture in any ordinary manner. This can be easily purified through separation means such as recrystallization, distillation, chromatography and the like.

Process 2

Process 2

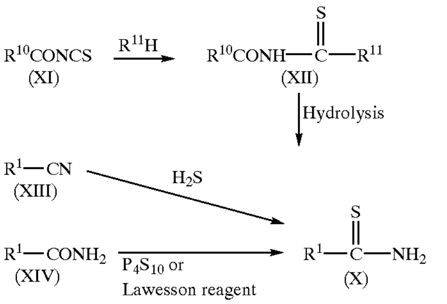

Compound (XII) is produced by subjecting compound (XI) to condensation with an amine of the formula: $R^{11}H$.

$R^{11}$ represents the "amine which may be substituted" for $R^1$ above.

In compound (XI), $R^{10}$ represents an alkoxy. The "alkoxy" includes, for example, a $C_{1-6}$ alkoxy such as methoxy, ethoxy, propoxy, isopropoxy, butoxy, etc.

The amount of the "amine" to be used is 1.0 to 30 mols or so, preferably 1.0 to 10 mols or so, relative to one mol of compound (XI).

This reaction is advantageously carried out in the absence of a solvent or in an inert solvent. There is no particular limitation on the kind of solvent that can be used unless the reaction is interfered with.

Preferred are halogenated hydrocarbons, aliphatic hydrocarbons, aromatic hydrocarbons, ethers, amides, alcohols, nitrites, ketones and mixtures-of those solvents. The reaction temperature is −5 to 200° C. or so, preferably 5 to 120° C. or so. The reaction time is generally 5 minutes to 72 hours, preferably about 0.5 to 30 hours.

The product as produced in the manner mentioned above may be applied to the next reaction while it is still crude in the reaction mixture, or may be isolated from the reaction mixture in any ordinary manner. This can be easily purified through separation means such as recrystallization, distillation, chromatography and the like.

Compound (X) is produced by subjecting compound (XII) to hydrolysis using an acid or a base.

The amount of the "acid" or "base" to be used is 0.1 to 50 mols or so, preferably 1 to 20 mols or so, relative to one mol of compound (XII), respectively.

The "acid" includes, for example, mineral acids such as hydrochloric acid, hydrobromic acid, sulfuric acid, etc; Lewis acids such as boron trichloride, boron tribromide, etc; thiols or sulfides in combination with Lewis acids; organic acids such as trifluoroacetic acid, p-toluenesulfonic acid, etc.

The "base" includes, for example, metal hydroxides such as sodium hydroxide, potassium hydroxide, barium hydroxide, etc.; metal alkoxides such as sodium methoxide, sodium ethoxide, potassium tert-butoxide, etc; organic bases such as triethylamine, imidazole, formamidine, etc.

This reaction is advantageously carried out in the absence of a solvent or in an inert solvent. There is no particular limitation on the kind of solvent that can be used unless the reaction is interfered with. Preferred are alcohols, ethers, aromatic hydrocarbons, aliphatic hydrocarbons, halogenated hydrocarbons, sulfoxides, water and mixtures of those solvents.

The reaction time is generally 10 minutes to 50 hours, preferably about 30 minutes to 12 hours. The reaction temperature is 0 to 200° C. or so, preferably 20 to 120° C. or so.

Compound (X) is also produced by treating compound (XIII) with a hydrogen sulfide in the presence of a base.

The amount of the hydrogen sulfide to be used is 1 to 30 mols or so, relative to one mol of compound (XIII).

The amount of the "base" to be used is 1.0 to 30 mols or so, preferably 1.0 to 10 mols or so, relative to one mol of compound (XIII).

The "base" includes, for example, aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.

This reaction is advantageously carried out in the absence of a solvent or in an inert solvent. There is. no particular limitation on the kind of solvent that can be used unless the reaction is interfered with. Preferred are halogenated hydrocarbons, aliphatic hydrocarbons, aromatic hydrocarbons, ethers, aromatic amines and mixtures of those solvents.

This reaction is carried out under atmospheric pressure or pressurized condition. The reaction temperature is −20 to 80° C. or so, preferably −10 to 30° C. or so. The reaction time is generally 5 minutes to 72 hours, preferably about 0.5 to 30 hours.

The product as produced in the manner mentioned above may be applied to the next reaction while it is still crude in the reaction mixture, or may be isolated from the reaction mixture in any ordinary manner. This can be easily purified through separation means such as recrystallization, distillation, chromatography and the like.

Compound (X) is also produced by treating compound (XIV) with a phosphorous pentasulfide or Lawesson's reagent.

The amount of the "phosphorous pentasulfide" or "Lawesson's reagent" to be used is 0.5 to 10 mols or so, preferably 0.5 to 3 mols or so, relative to one mol of compound (XIV).

This reaction is advantageously carried out in the absence of a solvent or in an inert solvent. There is no particular limitation on the kind of solvent that can be used unless the reaction is interfered with. Preferred are ethers, aromatic hydrocarbons, aliphatic hydrocarbons, halogenated hydrocarbons and mixtures of n those solvents.

The reaction time is generally 10 minutes to 50 hours, preferably about 30 minutes to 12 hours. The reaction temperature is 0 to 150° C. or so, preferably 20 to 120° C. or so.

The product (X) may be applied to the next reaction while it is still crude in the reaction mixture, or may be isolated from the reaction mixture in any ordinary manner. This can be easily purified through separation means such as recrystallization, distillation, chromatography and the like.

In case that compound (Ia) is an acylamino derivative, the desired product can be also obtained by subjecting the corresponded amine compound to any per se known acylation method.

For example, compound (Ia) wherein $R^1$ is an acylamino which may be substituted is produced by reacting a corresponding 2-thiazolyl amine with an acylating agent optionally in the presence of a base or an acid.

The amount of the "acylating agent" to be used is 1.0 to 5.0 mols or so, preferably 1.0 to 2.0 mols or so, relative to one mol of compound (Ia).

The “acylating agent” includes, for example, carboxylic acid or a reactive derivative thereof (e.g., acid halides, acid anhydrides, esters, etc.) corresponding to the desired product.

The amount of the “base” or “acid” to be used is 0.8 to 5.0 mols or so, preferably 1.0 to 2.0 mols or so, relative to one mol of compound (Ia).

The “base” includes, for example, triethylamine, pyridine, N,N-dimethylamino pyridine, etc.

The “acid” includes, for example, methanesulfonic acid, p-toluenesulfonic acid, camphor-sulfonic acid etc.

This reaction is advantageously carried out in the absence of a solvent or in an inert solvent. There is no particular limitation on the kind of solvent that can be used unless the reaction is interfered with. Preferred are ethers, aromatic hydrocarbons, aliphatic hydrocarbons, amides, halogenated hydrocarbons, nitrites, sulfoxides, aromatic amines and mixtures of those solvents.

The reaction temperature is −20 to 150° C. or so, preferably 0 to 100° C. or so. The reaction time is generally 5 minutes to 24 hours, preferably about 10 minutes to 5 hours.

The product may be applied to the next reaction while it is still crude in the reaction mixture, or may be isolated from the reaction mixture in any ordinary manner. This can be easily purified through separation means such as recrystallization, distillation, chromatography and the like.

Compound (Ic) can be also produced according to the methods of the following process 3 or analogous methods thereto.

Process 3

Process 3

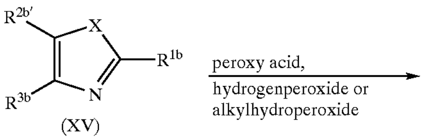

(XV) (Ic)

Compound (XV) can be produced according to any per se known methods or analogous methods thereto.

Compound (Ic) is produced by treating compound (XV) with a peroxy acid.

In compound (XV), $R^{2b'}$ represents a pyridyl which may be substituted. The “pyridyl which may be substituted” includes, for example, the “pyridyl which may be substituted” for $R^2$ above.

The amount of the “peroxy acid” to be used is 0.8 to 10 mols or so, preferably 1.0 to 3.0 mols or so, relative to one mol of compound (XV).

The “peroxy acid” includes, for example, peracetic acid, trifluoroperacetic acid, m-chloroperbenzoic acid, etc.

This reaction is advantageously carried out in the absence of a solvent or in an inert solvent. There is no particular limitation on the kind of solvent that can be used unless the reaction is interfered with. Preferred are halogenated hydrocarbons, aliphatic hydrocarbons, aromatic hydrocarbons, organic acids, ethers, amides, sulfoxides, alcohols, nitriles, ketones and mixtures of those solvents.

The reaction temperature is −20 to 130° C. or so, preferably 0 to 100° C. or so. The reaction time is generally 5 minutes to 72 hours, preferably about 0.5 to 12 hours.

Compound (Ic) is also produced by treating compound (XV) with a hydrogen peroxide or an alkylhydroperoxide, in the presence of a base, an acid or a metal oxide if desired.

The amount of the “hydrogen peroxide” or the “alkylhydroperoxide” to be used is 0.8 to 10 mols or so, preferably 1.0 to 3.0 mols or so, relative to one mol of compound (XV).

The “alkylhydroperoxide” includes, for example, tert-butylhydroperoxide, cumene hydroperoxide, etc.

The amount of the “base” the “acid” or the “metal oxides” to be used is 0.1 to 30 mols or so, preferably 0.8 to 5 mols or so, relative to one mol of compound (XV).

The “base” includes, for example, inorganic bases such as sodium hydroxide and potassium hydroxide, basic salts such as sodium carbonate and potassium carbonate, etc.

The “acid” includes, for example, mineral acids such as hydrochloric acid, sulfuric acid and perchloric acid, Lewis acids such as boron trifluoride and aluminum (III) chloride, titanium(IV) chloride, organic acids such as formic acid and acetic acid, etc.

The “metal oxides” includes, for example, vanadium oxide ($V_2O_5$), osmium oxide ($OSO_4$), tungsten oxide ($WO_3$), molybdenum oxide ($MoO_3$), selenium oxide ($SeO_2$), chromium oxide ($CrO_3$), etc.

This reaction is advantageously carried out in the absence of a solvent or in an inert solvent. There is no particular limitation on the kind of solvent that can be used unless the reaction is interfered with. Preferred are halogenated hydrocarbons, aliphatic hydrocarbons, aromatic hydrocarbons, organic acids, ethers, amides, sulfoxides, alcohols, nitrites, ketones and mixtures of those solvents.

The reaction temperature is −20 to 130° C. or so, preferably 0 to 100° C. or so. The reaction time is generally 5 minutes to 72 hours, preferably about 0.5 to 12 hours.

The product may be applied to the next reaction while it is still crude in the reaction mixture, or may be isolated from the reaction mixture in any ordinary manner. This can be easily purified through separation means such as recrystallization, distillation, chromatography and the like.

In the above-mentioned reactions where the starting compounds are substituted by any of amino, carboxy or hydroxy, those groups may be protected by ordinary protective groups which are generally used in peptide chemistry. The protective groups may be removed after the reaction to give the desired products.

The amino-protecting group includes, for example, formyl, $C_{1-6}$ alkyl-carbonyl (e.g., acetyl, propionyl, etc.) which may be substituted, phenylcarbonyl which may be substituted, $C_{1-6}$ alkoxy-carbonyl (e.g., methoxycarbonyl, ethoxycarbonyl, etc.) which may be substituted, phenyloxycarbonyl which may be substituted, $C_{7-10}$ aralkyloxycarbonyl (e.g., benzyloxycarbonyl, etc.) which may be substituted, trityl which may be substituted, phthaloyl which may be substituted, etc. These substituents include, for example, halogen atoms (e.g., fluoro, chloro, bromo, iodo, etc.), $C_{1-6}$ alkyl-carbonyl (e.g., acetyl, propionyl, valeryl, etc.), nitro, etc. The number of those substituents is 1 to 3.

The carboxy-protecting group includes, for example, $C_{1-6}$ alkyl (e.g., methyl, ethyl, propyl, isopropyl, butyl, tert-butyl, etc.) which may be substituted, phenyl which may be substituted, trityl which may be substituted, silyl which may be substituted, etc. These substituents include, for example, halogen atoms (e.g., fluoro, chloro, bromo, iodo, etc.), formyl, $C_{1-6}$ alkyl-carbonyl (e.g., acetyl, propionyl, butylcarbonyl, etc.), nitro, $C_{1-6}$ alkyl (e.g., methyl, ethyl, tert-butyl, etc.), $C_{6-10}$ aryl (e.g., phenyl, naphthyl, etc.), etc. The number of those substituents is 1 to 3.

The hydroxy-protecting group includes, for example, $C_{1-6}$ alkyl (e.g., methyl, ethyl, propyl, isopropyl, butyl, tert-butyl, etc.) which may be substituted, phenyl which may be substituted, $C_{7-11}$ aralkyl (e.g., benzyl, etc.) which may be substituted, formyl which may be substituted, $C_{1-6}$ alkyl-carbonyl (e.g., acetyl, propionyl, etc.) which may be substituted, phenyloxycarbonyl which may be substituted, $C_{7-11}$ aralkyloxy-carbonyl (e.g., benzyloxycarbonyl, etc.) which may be substituted, tetrahydropyranyl which may be substituted, tetrahydrofuranyl which may be substituted, silyl which may be substituted, etc. Those substituents include, for example, halogen atoms (e.g., fluoro, chloro, bromo, lodo, etc.), $C_{1-6}$ alkyl (e.g., methyl, ethyl, tert-butyl, etc.), $C_{7-11}$ aralkyl (e.g., benzyl, etc.), $C_{6-10}$ aryl(e.g., phenyl, naphthyl, etc.), nitro, etc. The number of those substituents is 1 to 4.

Those protective groups may be removed by any per se known methods or analogous methods thereto, such as methods using acids, bases, ultraviolet rays, hydrazine, phenylhydrazine, sodium N-methyldithiocarbamate, tetrabutylammonium fluoride, palladium acetate, etc.; and reduction, etc.

In any case, products formed in the reaction mixtures may be subjected to deprotection, acylation, alkylation, hydrogenation, oxidation, reduction, chain extension, substituents-exchange reaction and combined reactions thereof, to obtain compound (I). These methods include, for example, the methods described in "Shin Jikken Kagaku Kouza (New Edition of Lectures of Experimental Chemistry)" 14, 15 (1977) edited by Maruzen.

The above "alcohols" include, for example, methanol, ethanol, propanol, isopropanol, tert-butanol, etc.

The above "ethers" include, for example, diethyl ether, diisopropyl ether, diphenyl ether, tetrahydrofuran, dioxane, 1,2-dimethoxyethane, etc.

The above "halogenated hydrocarbons" include, for example, dichloromethane, chloroform, 1,2-dichloroethane, carbon tetrachloride, etc.

The above "aliphatic hydrocarbons" include, for example, hexane, pentane, cyclohexane, etc.

The above "aromatic hydrocarbons" include, for example, benzene, toluene, xylene, chlorobenzene, etc.

The above "aromatic amines" include, for example, pyridine, lutidine, quinoline, etc.

The above "amides" include, for example, N,N-dimethylformamide, N,N-dimethylacetamide, hexamethylphosphoric triamide, etc.

The above "ketones" include, for example, acetone, methyl ethyl ketone, etc.

The above "sulfoxides" include, for example, dimethylsulfoxide, etc.

The above "nitrites" include, for example, acetonitrile, propionitrile, etc.

The above "organic acids" include, for example, acetic acid, propionic acid, trifluoroacetic acid, etc.

Where the products are formed in their free form in the reaction, they may be converted into their salts in any ordinary manner. Where they are formed in the form of their salts, they may be converted into free compounds or other salts in any ordinary manner. The thus-obtained compound (I) may be isolated and purified from the reaction mixtures through any ordinary means of, for example, trans-solvation, concentration, solvent extraction, fractionation, crystallization, recrystallization, chromatography and the like.

Where compound (I), (Ia), (Ib) or (Ic) exists in the reaction mixtures in the form of its configurational isomers, diastereomers, conformers or the like, they may be optionally isolated into single isomers through the separation and isolation means mentioned above. Where compound (I), (Ia), (Ib) or (Ic) is in the form of its racemates, they may be resolved into S- and R-forms through any ordinary optical resolution.

Compound (I), (Ia), (Ib) or (Ic) includes stereoisomers, depending on the type of the substituents therein, and both single isomers and mixtures of different isomers are within the scope of the present invention.

Compounds (I), (Ia), (Ib) and (Ic) may be in any form of their hydrates and non-hydrates.

The agent (pharmaceutical composition) of the. present invention comprising compound (I), (Ia), (Ib) or (Ic) shows a high affinity for adenosine receptor, especially for adenosine $A_3$ receptor, while having low toxicity and few side effects. The agent is useful as a safe medicine.

The agent (pharmaceutical composition) of the present invention comprising compound (I), (Ia), (Ib) or (Ic) has a potent antagonistic activity on mammals (e.g., mouse, rat, hamster, rabbit, feline, canine, bovine, sheep, monkey, human, etc.), a good bioavailability upon administration, a good metabolical stability, and therefore, it can be used for preventing and/or treating diseases that may be related to adenosine $A_3$ receptor, for example, asthma, allergosis, inflammation, Addison's disease, autoallergic hemolytic anemia, Crohn's disease, psoriasis, rheumatism, diabetes, and so on. Among others, preferred is for asthma, allergosis, etc.

The agent (pharmaceutical composition) of the present invention comprising compound (I), (Ia), (Ib) or (Ic) has low toxicity, and therefore, compound (I), (Ia), (Ib) or (Ic) is, either directly as it is or after having been formulated into pharmaceutical compositions along with pharmaceutically acceptable carriers in any per se known manner, for example, into tablets (including sugar-coated tablets, film-coated tablets), powders, granules, capsules (including soft capsules), liquid preparations, injections, suppositories, sustained release preparations, etc., safely administered orally or parenterally (e.g., locally, rectally, intravenously, etc.). In the pharmaceutical composition of the present invention, the amount of compound (I), (Ia), (Ib) or (Ic) is from 0.01 to 100% by weight or so of the total weight of the composition. The dose of the composition varies, depending on the subject to which the composition is administered, the administration route employed, the disorder of the subject, etc. For example, as an adenosine $A_3$ receptor antagonist, oral composition for treating asthma, its dose for adults (body weight ca. 60 kg) may be from 0.1 to 30 mg/kg of body weight or so, preferably from 1 to 20 mg/kg of body weight or so, in terms of the active ingredient of compound (I), (Ia), (Ib) or (Ic), and this may be administered once or several times a day.

Any ordinary organic and inorganic carrier substances that are generally used in formulating medicines are usable as the carriers for formulating the pharmaceutical compositions of the present invention. For example, employable are ordinary excipients, lubricants, binders, disintegrators, etc. for formulating solid preparations; and solvents, solubilizers, suspending agents, isotonizing agents, buffers, soothing agents, etc. for formulating liquid preparations. If desired, further employable are other additives such as preservatives, antioxidants, colorants, sweeteners, absorbents, wetting agents, etc.

The excipients include, for example, lactose, white sugar, D-mannitol, starch, corn starch, crystalline cellulose, light silicic anhydride, etc.

The lubricants include, for example, magnesium stearate, calcium stearate, talc, colloidal silica, etc.

The binders include, for example, crystalline cellulose, white sugar, D-mannitol, dextrin, hydroxypropyl cellulose, hydroxypropylmethyl cellulose, polyvinyl pyrrolidone, starch, sucrose, gelatin, methyl cellulose, carboxymethyl cellulose sodium, etc.

The disintegrators include, for example, starch, carboxymethyl cellulose, carboxymethyl cellulose calcium, croscarmellose sodium, carboxymethyl starch sodium, L-hydroxypropyl cellulose, etc.

The solvents include, for example, water for injections, alcohol, propylene glycol, macrogol, sesame oil, corn oil, olive oil, etc. The solubilizers include, for example, polyethylene glycol, propylene glycol, D-mannitol, benzyl benzoate, ethanol, trisaminomethane, cholesterol, triethanolamine, sodium carbonate, sodium citrate, etc.

The suspending agents include, for example, surfactants such as stearyl triethanolamine, sodium lauryl sulfate, lauryl aminopropionic acid, lecithin, benzalkonium chloride, benzethonium chloride, glycerin monostearate, etc.; hydrophilic polymers such as polyvinyl alcohol, polyvinyl pyrrolidone, carboxymethyl cellulose sodium, methyl cellulose, hydroxymethyl cellulose, hydroxyethyl cellulose, hydroxypropyl cellulose, etc.

The isotonizing agents include, for example, glucose, D-sorbitol, sodium chloride, glycerin, D-mannitol, etc.

The buffers include, for example, liquid buffers of phosphates, acetates, carbonates, citrates, etc.

The soothing agents include, for example, benzyl alcohol, etc.

A The preservatives include, for example, parahydroxybenzoates, chlorobutanol, benzyl alcohol, phenethyl alcohol, dehydroacetic acid, sorbic acid, etc.

The antioxidants include, for example, sulfites, ascorbic acid, etc.

BEST MODE FOR CARRYING OUT THE INVENTION

The invention will be described in more detail hereinunder, with reference to the following Reference Examples, Examples, Formulation Examples and Experimental Examples, which, however, are to concretely illustrate some embodiments of the invention and are not intended to restrict the scope of the invention. Various changes and modifications can be made within the range that does not deviate the scope of the invention.

"Room temperature" as referred to in the following Reference Examples and Examples is meant to indicate a temperature falling between 10° C. and 35° C. Unless otherwise specifically indicated, "%" is by weight. The yield indicates mol/mol %.

The meanings of the abbreviations used hereinunder are as follows:

s: singlet d: doublet t: triplet q: quartet dd: double doublet ddd: double double doublet dt: double triplet br: broad J: coupling constant Hz: Hertz $CDCl_3$: deuterated chloroform $^1H$-NMR: proton nuclear magnetic resonance spectrum Me: methyl

REFERENCE EXAMPLE 1

1-(4-Methoxyphenyl)-2-(3-pyridyl)ethanone

To a stirred solution of diisopropylamine (33.2 mL) in dry tetrahydrofuran (300 mL) cooled at −78° C., was added a solution of 1.6 M n-butyllithium in hexane (148 mL) dropwise. After addition, the resulting mixture was stirred for 10 min at the same temperature, followed by the addition of β-picoline (20 g). The resulting mixture was allowed to warm up to −10–0° C. After an additional 20 min stirring, a solution of ethyl p-anisate (19.4 g) in dry tetrahydrofuran (40 mL) was added. After addition the mixture was stirred for another 1 h at ambient temperature, and water (100 mL) was added to the mixture. The solvent was removed under reduced pressure and the oily product was extracted with ethyl acetate. The extracts were washed with water, dried, and concentrated under reduced pressure. The crystalline residue was recrystallized from ethyl acetate—isopropyl ether to afford the title compound (20.8 g, yield 85%).

mp 71–72° C.

REFERENCE EXAMPLE 2

Using ethyl benzoate, ethyl 3,4-dimethoxybenzoate, ethyl 3,4,5-trimethoxybenzoate, ethyl 4-(methoxymethoxy) benzoate, ethyl 4-fluorobenzoate, ethyl 4-ethylbenzoate, ethyl 3,4-methylenedioxybenzoate, methyl 5-indanecarboxylate, methyl 5,6,7,8-tetrahydro-2-naphthoic acid, methyl 1,4-benzodioxane-6-carboxylate, and methyl 2-naphthoic acid instead of using ethyl p-anisate, the below Reference Example Compounds 2-1 to 2-11 were obtained in the same manner as described in the above Reference Example 1.

Reference Example Compound 2-1:
1-Phenyl-2-(3-pyridyl)ethanbne
mp 44.5–45.5° C.

Reference Example Compound 2-2:
1-(3,4-Dimethoxyphenyl)-2-(3-pyridyl)ethanone
mp 114–115° C.

Reference Example Compound 2-3:
2-(3-Pyridyl)-1-(3,4,5-trimethoxyphenyl)ethanone
mp 104–105° C.

Reference Example Compound 2-4:
1-(4-Methoxymethoxyphenyl)-2-(3-pyridyl)ethanone
mp 43–44° C.

Reference Example Compound 2-5:
1-(4-Fluorophenyl)-2-(3-pyridyl)ethanone
oil.

Reference Example Compound 2-6:
1-(4-Ethylphenyl)-2-(3-pyridyl)ethanone
mp 80–81° C.

Reference Example Compound 2-7:
1-(3,4-Methylenedioxyphenyl)-2-(3-pyridyl)ethanone
mp 98–99° C.

Reference Example Compound 2-8:
1-(5-Indanyl)-2-(3-pyridyl)ethanone
mp 55–56° C.

Reference Example Compound 2-9:
2-(3-Pyridyl)-1-(5,6,7,8-tetrahydro-2-naphthyl)ethanone
mp 65–66° C.

Reference Example Compound 2-10:
1-(1,4-Benzodioxan-6-yl)-2-(3-pyridyl)ethanone
mp 89–90° C.

Reference Example Compound 2-11:
1-(2-Naphtyl)-2-(3-pyridyl)ethanone
mp 69–70° C.

REFERENCE EXAMPLE 3

Using α-picoline, γ-picoline, and 3,5-lutidine instead of using β-picoline, the below Reference Example Compounds 3-1 to 3-5 were obtained in the same manner as described in the above Reference Example 2.

Reference Example Compound 3-1:
1-Phenyl-2-(2-pyridyl)ethanone
mp 59–60° C.
Reference Example Compound 3-2:
1-(4-Methoxyphenyl)-2-(2-pyridyl)ethanone
mp 77–78° C.
Reference Example Compound 3-3:
1-Phenyl-2-(4-pyridyl)ethanone
mp 109–110° C.
Reference Example Compound 3-4:
1-(4-Methoxyphenyl)-2-(4-pyridyl)ethanone
mp 103–104° C.
Reference Example Compound 3-5:
2-(5-Methyl-3-pyridyl)-1-phenylethanone
mp 53–54° C.

REFERENCE EXAMPLE 4

2-Cyano-2-phenyl-1-(3-pyridyl)ethanone

To a solution of ethyl nicotinate (10 g) and phenylacetonitrile (5.1 g) in tert-butyl alcohol (30 mL), was added potassium tert-butoxide (6.4 g), and the mixture was stirred at 100° C. for 3 h. After cooling, the resulting mixture was dissolved in water and washed with isopropyl ether. The aqueous phase was adjusted to pH 7.0 with 2 N hydrochloric acid and extracted with ethyl acetate. The extracts were washed with water, dried, and the solvent was evaporated. The crystalline residue was recrystallized from ethyl acetate-isopropyl ether to obtain the title compound (6.0 g, yield 62%).

mp 148–149° C.

REFERENCE EXAMPLE 5

2-Phenyl-1-(3-pyridyl)ethanone

2-Cyano-2-phenyl-1-(3-pyridyl)ethanone (5.0 g) was dissolved in 48% hydrobromic acid (50 mL) and the solution was stirred at 140° C. for 5 h. After the mixture was cooled, the mixture was neutralized with an aqueous saturated solution of sodium hydrogen carbonate and the product was extracted with ethyl acetate. The extracts were washed with water, dried, and the solvent was evaporated. The crystalline residue was recrystallized from isopropyl ether to obtain the title compound (3.9 g, yield 88%).

mp 61–62° C.

REFERENCE EXAMPLE 6

2-Bromo-1-(4-methoxyphenyl)-2-(3-pyridyl)ethanone Hydrobromide 1-(4-Methoxyphenyl)-2-(3-pyridyl)ethanone (6.85 g) was dissolved in acetic acid (36 mL), bromine (1.7 mL) was added to the solution and the resulting mixture was stirred at 80° C. for 3 h. After the mixture was cooled with ice-water, the crude crystalline mass was collected by filtration. The crude crystalline was recrystallized from ethanol-ethyl ether to afford the title compound (10.4 g, yield 89%).

mp 188–195° C.

REFERENCE EXAMPLE 7

Using 1-phenyl-2-(3-pyridyl)ethanone, 1-(3,4-dimethoxyphenyl)-2-(3-pyridyl)ethanone, 2-(3-pyridyl)-1-(3,4,5-trimethoxyphenyl)ethanone, 1-(4-methoxymethoxyphenyl)-2-(3-pyridyl)ethanone, 1-(4-fluorophenyl)-2-(3-pyridyl)ethanone, 1-phenyl-2-(2-pyridyl)ethanone, 1-(4-methoxyphenyl)-2-(2-pyridyl)ethanone, 1-phenyl-2-(4-pyridyl)ethanone, 1-(4-methoxyphenyl)-2-(4-pyridyl)ethanone, 2-(5-methyl-3-pyridyl)-1-phenylethanone, 1-(4-ethylphenyl)-2-(3-pyridyl)ethanone, 1-(3,4-methylenedioxyphenyl)-2-(3-pyridyl)ethanone, 1-(5-indanyl)-2 -(3-pyridyl)ethanone, 2-(3-pyridyl)-1-(5,6,7,8-tetrahydro-2-naphthyl)ethanone, 1-(1,4-benzodioxan-6-yl)-2-(3-pyridyl)ethanone, 1-(2-naphthyl)-2-(3-pyridyl)ethanone, 1-(4-methoxyphenyl)-2-(2-pyridyl)ethanone and 2-phenyl-1-(3-pyridyl)ethanone instead of using 1-(4-methoxyphenyl)-2-(3-pyridyl)ethanone, the below Reference Example Compounds 7-1 to 7-18 were obtained in the same manner as described in the above Reference Example 6.

Reference Example Compound 7-1:
2-Bromo-1-phenyl-2-(3-pyridyl)ethanone Hydrobromide
mp 208–215° C.
Reference Example Compound 7-2:
2-Bromo-1-(3,4-dimethoxyphenyl)-2-(3-pyridyl)ethanone Hydrobromide
mp 191–193° C.
Reference Example Compound 7-3:
2-Bromo-2-(3-pyridyl)-1-(3,4,5-trimethoxyphenyl)ethanone Hydrobromide
mp 184–186° C.
Reference Example Compound 7-4:
2-Bromo-1-(4-hydroxyphenyl)-2-(3-pyridyl)ethanone Hydrobromide The crude mixture without purification was used in the next reaction.

Reference Example Compound 7-5:
2-Bromo-1-(4-fluorophenyl)-2-(3-pyridyl)ethanone Hydrobromide
mp 189–191° C.
Reference Example Compound 7-6:
2-Bromo-1-phenyl-2-(2-pyridyl)ethanone Hydrobromide
mp 180–181° C.
Reference Example Compound 7-7:
2-Bromo-1-(4-methoxyphenyl)-2-(2-pyridyl)ethanone Hydrobromide
mp 170–171° C.
Reference Example Compound 7-8:
2-Bromo-1-phenyl-2-(4-pyridyl)ethanone Hydrobromide
mp 230–232° C.
Reference Example Compound 7-9:
2-Bromo-1-(4-methoxyphenyl)-2-(4-pyridyl)ethanone Hydrobromide
mp 207–209° C.
Reference Example Compound 7-10:
2-Bromo-2-(5-methyl-3-pyridyl)-1-phenylethanone Hydrobromide
mp 189–193° C.
Reference Example Compound 7-11:
2-Bromo-1-(4-ethylphenyl)-2-(3-pyridyl)ethanone Hydrobromide
mp 145–146° C.
Reference Example Compound 7-12:
2-Bromo-1-(3,4-methylenedioxyphenyl)-2-(3-pyridyl)ethanone Hydrobromide
mp 174–175° C.
Reference Example Compound 7-13:
2-Bromo-1-(5-indanyl)-2-(3-pyridyl)ethanone Hydrobromide
mp 177–178° C.
Reference Example Compound 7-14:
2-Bromo-2-(3-pyridyl)-1-(5,6,7,8-tetrahydro-2-naphthyl)ethanone Hydrobromide
mp 160–162° C.
Reference Example Compound 7-15:
1-(1,4-Benzodioxan-6-yl)-2-bromo-2-(3-pyridyl)ethanone Hydrobromide
oil.

Reference Example Compound 7-16:

2-Bromo-1-(2-naphthyl)-2-(3-pyridyl)ethanone Hydrobromide mp 197–199° C.

Reference Example Compound 7-17:

2-Bromo-1-(4-methoxyphenyl)-2-(2-pyridyl)ethanone Hydrobromide mp 170–171° C.

Reference Example Compound 7-18:

2-Bromo-2-phenyl-1-(3-pyridyl)ethanone Hydrobromide mp 213–218° C.

REFERENCE EXAMPLE 8

[4-(4-Methoxyphenyl)-5-(3-pyridyl)-1,3-thiazol-2-yl]amine

To a suspension of thiourea (516 mg) in acetonitrile (40 mL), was added 2-bromo-1-(4-methoxyphenyl)-2-(3-pyridyl)ethanone hydrobromide (2.5 g), and then triethylamine (0.95 mL) was added slowly dropwise to the mixture with stirring. After addition, the mixture was stirred at reflux for 3 h. After cooling, the crude crystalline was collected by filtration. The crystalline was washed with an aqueous saturated solution of sodium hydrogen carbonate, water, ethanol, and ethyl ether, in that order, and dried. The obtained crude crystalline was recrystallized from tetrahydrofuran to give the title compound (1.5 g, yield 90%).

mp 265–266° C.

REFERENCE EXAMPLE 9

N-Methyl[4-(4-methoxyphenyl)-5-(3-pyridyl)-1,3-thiazol-2-yl]amine

To a suspension of N-methylthiourea (242 mg) in acetonitrile (18 mL), was added 2-bromo-1-(4-methoxyphenyl)-2-(3-pyridyl)ethanone hydrobromide (1.0 g) and then triethylamine (0.4 mL) was added slowly dropwise to the mixture. After addition, the resulting mixture was stirred at reflux for 3 h, and the solvent was evaporated. An aqueous saturated solution of sodium hydrogen carbonate was added to the residue and extracted with ethyl acetate. The extracts were washed with water, dried, and the solvent was evaporated. The crystalline residue was recrystallized from ethyl acetate-isopropyl ether to afford the title compound (650 mg, yield 85%).

mp 158–159° C.

REFERENCE EXAMPLE 10

N-[4-(4-Methoxyphenyl)-5-(3-pyridyl)-1,3-thiazol-2-yl]acetamide

Using [(4-methoxyphenyl)-5-(3-pyridyl)-1,3-thiazol-2-yl]amine as starting material, the title compound was obtained in the same manner as described in below Example 3. Yield 82%.

mp 208–210° C.

REFERENCE EXAMPLE 11

2-(4-Acetylpiperazin-1-yl)-4-(4-methoxyphenyl)-5-(3-pyridyl)-1,3-thiazole

To a solution of 1-piperazinecarbothioamide (387 mg) in acetonitrile (15 mL), was added 2-bromo-1-(4-methoxyphenyl)-2-(3-pyridyl)ethanone hydrobromide (1.0 g), and then triethylamine (0.4 mL) was added slowly dropwise to the resulting mixture. After addition the mixture was stirred at reflux for3 h and the solvent was evaporated. An aqueous saturated solution of sodium hydrogen carbonate was added to the residue and extracted with ethyl acetate. The extracts were washed with water, dried and the solvent was evaporated. The residue was dissolved in pyridine (2 mL) and acetyl chloride (0.3 mL) was added to the solution under ice cooling. The resulting mixture was stood at room temperature for 1 h. The reaction mixture was poured into ice-water and the product was extracted with ethyl acetate. The extracts were washed with water, dried, and the solvent was evaporated. The residue was purified using silica-gel column chromatography (ethyl acetate-methanol, 9:1) to give the title compound (300 mg, yield 28%).

oil.

REFERENCE EXAMPLE 12

[4-(4-Methoxyphenyl)-5-(3-pyridyl)-1,3-thiazol-2-yl]amine Hydrochloride

[4-(4-Methoxyphenyl)-5-(3-pyridyl)-I,3-thiazol-2-yl]amine (200 mg) was dissolved in 1% methanol solution of hydrogen chloride (3.2 mL), and the solvent was evaporated. The crude crystalline was recrystallized from methanol-ethyl acetate to give the title compound (180 mg, yield 80%).

mp 145–150° C.

The chemical structures of the compounds obtained in the Reference Examples 8 to 12 are shown in Table 1.

TABLE 1

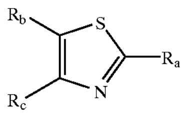

| Ref. Ex. Compd. | $R_a$ | $R_b$ | $R_c$ | Additive |
|---|---|---|---|---|
| 8 | —$NH_2$ | 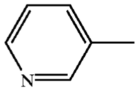 | 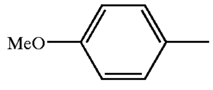 | |
| 9 | —NHMe | 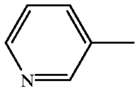 | 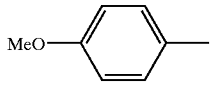 | |
| 10 | —NHCOMe | 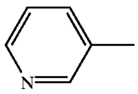 | 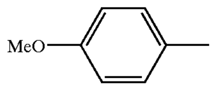 | |

TABLE 1-continued
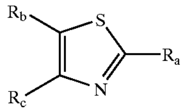
| Ref. Ex. Compd. | $R_a$ | $R_b$ | $R_c$ | Additive |
|---|---|---|---|---|
| 11 | 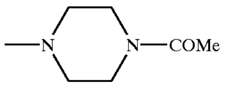 | 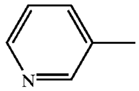 | 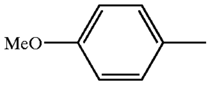 | |
| 12 | —$NH_2$ | 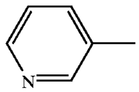 | 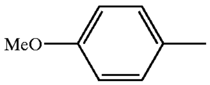 | HCl |
REFERENCE EXAMPLE 13
The following Reference Example Compounds13-1 to 13-106 shown in Tables 2 to 7 were obtained in the same manner as described in the above References 8 to 12, JP-A-61-10580 and U.S. Pat. No. 4,612,321.
TABLE 2
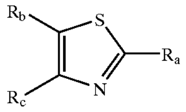
| Ref. Ex. Compd. | $R_a$ | $R_b$ | $R_c$ | mp/° C. |
|---|---|---|---|---|
| 13-1 | —NHMe | 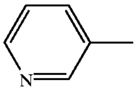 | 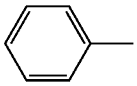 | 168–169 |
| 13-2 | —$NH_2$ | 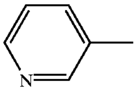 | 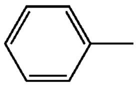 | 253–254 |
| 13-3 | —$NH_2$ | 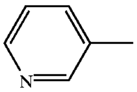 | 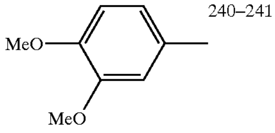 | 240–241 |
| 13-4 | —$NH_2$ | 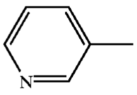 | 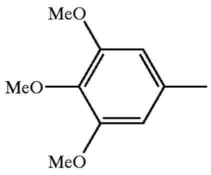 | 168–169 |
| 13-5 | —NHMe | 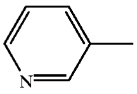 | 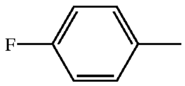 | 157–158 |

TABLE 2-continued
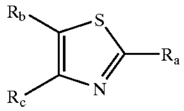
| Ref. Ex. Compd. | $R_a$ | $R_b$ | $R_c$ | mp/° C. |
|---|---|---|---|---|
| 13-6 | —NHMe | 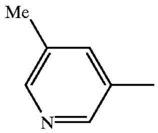 | 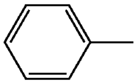 | 205–206 |
| 13-7 | $—NH_2$ | 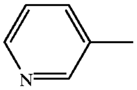 | 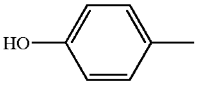 | 266–268 |
| 13-8 | $—NHCOCH_2COOCH_2Me$ | 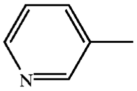 | 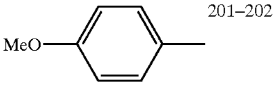 | 201–202 |
| 13-9 | $—NHCOCH_2COOMe$ | 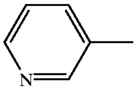 | 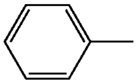 | 185–186 |
| 13-10 | $—NH_2$ | 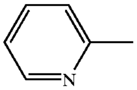 | 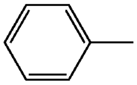 | 236–237 |
| 13-11 | —NHMe | 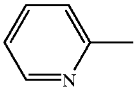 | 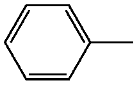 | 215–216 |
| 13-12 | —NHMe | 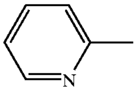 | 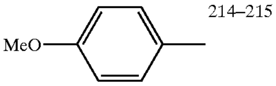 | 214–215 |
| 13-13 | $—NH_2$ | 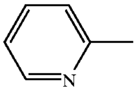 | 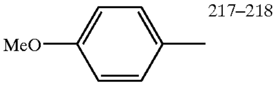 | 217–218 |
| 13-14 | $—NH_2$ | 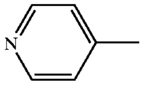 | 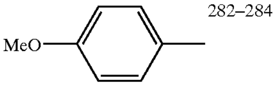 | 282–284 |
| 13-15 | $—NH_2$ | 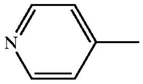 | 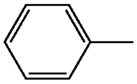 | 248–250 |
| 13-16 | —NHMe | 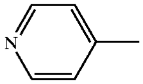 | 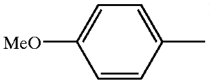 | 177–178 |
| 13-17 | 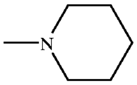 | 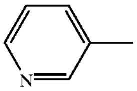 | 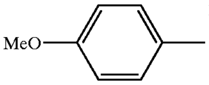 | 130–131 |
| 13-18 | 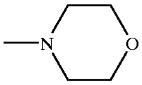 | 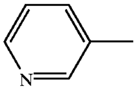 | 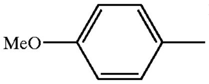 | 134–135 |

TABLE 3
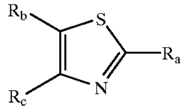
| Ref. Ex. Compd. | $R_a$ | $R_b$ | $R_c$ | mp/° C. |
|---|---|---|---|---|
| 13-19 | —$CH_2Me$ | 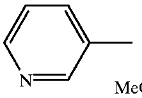 | 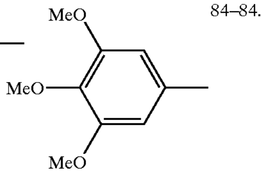 | 84–84.5 |
| 13-20 | —$CH_2Me$ | 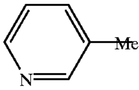 | 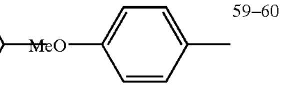 | 59–60 |
| 13-21 | —$CH_2Me$ | 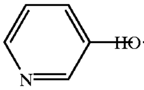 | 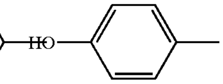 | 174–175 |
| 13-22 | —Me | 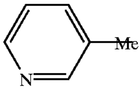 | 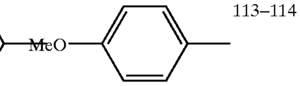 | 113–114 |
| 13-23 | —$CH_2Me$ | 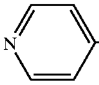 | 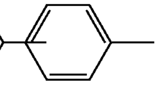 | 83–84 |
| 13-24 | 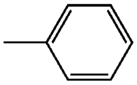 | 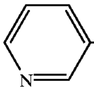 | 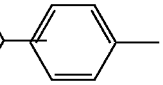 | 135–136 |
| 13-25 | 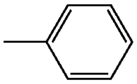 | 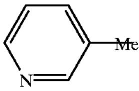 | 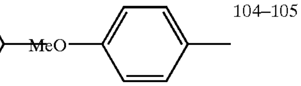 | 104–105 |
| 13-26 | 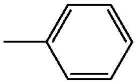 | 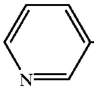 | 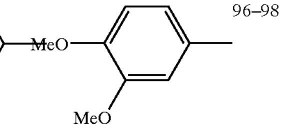 | 96–98 |
| 13-27 | 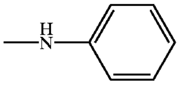 | 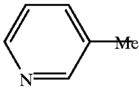 | 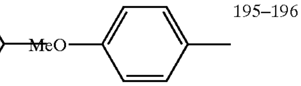 | 195–196 |
| 13-28 | 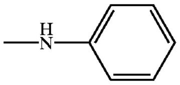 | 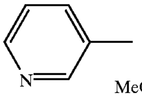 | 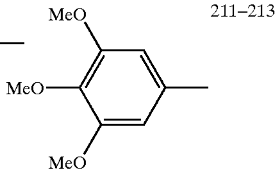 | 211–213 |
| 13-29 | 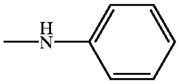 | 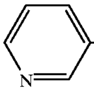 | 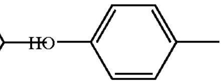 | 280–282 |

TABLE 3-continued
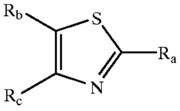
| Ref. Ex. Compd. | $R_a$ | $R_b$ | $R_c$ | mp/° C. |
|---|---|---|---|---|
| 13-30 | 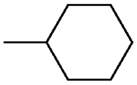 | 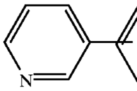 | 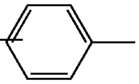 | 100–101 |
| 13-31 | 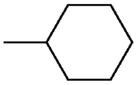 | 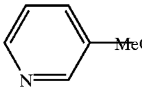 | 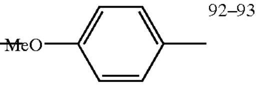 | 92–93 |
| 13-32 | 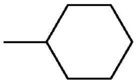 | 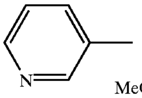 | 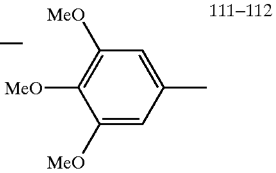 | 111–112 |
| 13-33 | 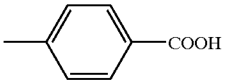 | 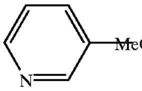 | 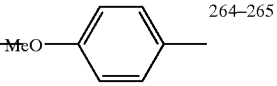 | 264–265 |
| 13-34 | 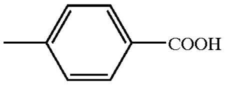 | 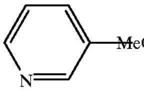 | 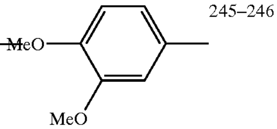 | 245–246 |
| 13-35 | 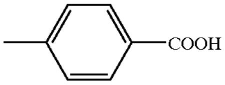 | 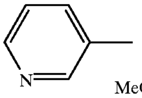 | 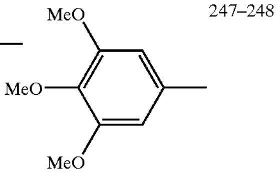 | 247–248 |
TABLE 4
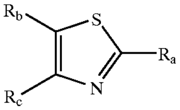
| Ref. Ex. Compd. | $R_a$ | $R_b$ | $R_c$ | mp/° C. |
|---|---|---|---|---|
| 13-36 | —Me | 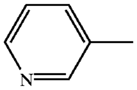 | 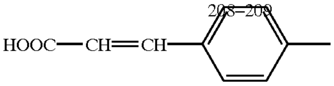 | 208–209 |
| 13-37 | 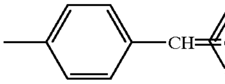 | 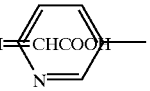 | 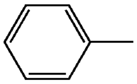 | 255–256 |

TABLE 4-continued
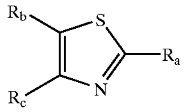
| Ref. Ex. Compd. | $R_a$ | $R_b$ | $R_c$ | mp/° C. |
|---|---|---|---|---|
| 13-38 | 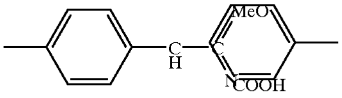 | | 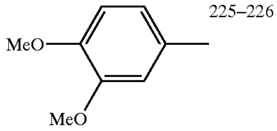 | 225–226 |
| 13-39 | —$(CH_2)_3COOH$ | 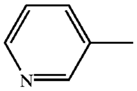 | 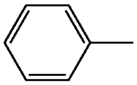 | 143–144 |
| 13-40 | —$(CH_2)_3COOH$ | 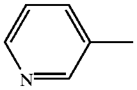 | 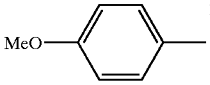 | 163–164 |
| 13-41 | —$(CH_2)_3COOH$ | 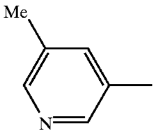 | 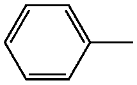 | 134–135 |
| 13-42 | —$(CH_2)_3COOH$ | 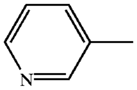 | 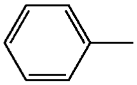 | 112–113 |
| 13-43 | —$(CH_2)_4OH$ | 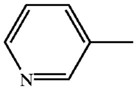 | 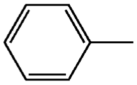 | 51–52 |
| 13-44 | —$NHCH_2Me$ | 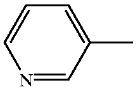 | 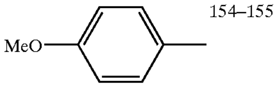 | 154–155 |
| 13-45 | —NHMe | 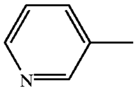 | 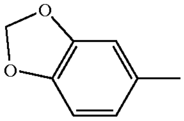 | 187–188 |
| 13-46 | —NHMe | 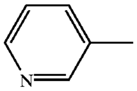 | 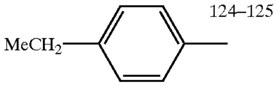 | 124–125 |
| 13-47 | —NHMe | 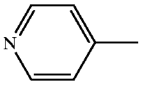 | 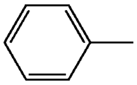 | 191–192 |
| 13-48 | —$N(CH_2Me)_2$ | 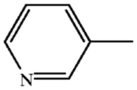 | 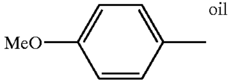 | oil |
| 13-49 | —$NME_2$ | 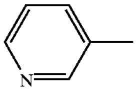 | 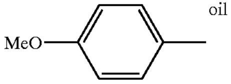 | oil |

TABLE 4-continued
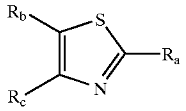
| Ref. Ex. Compd. | $R_a$ | $R_b$ | $R_c$ | mp/° C. |
|---|---|---|---|---|
| 13-50 | —$CH_2Me$ | 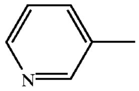 | 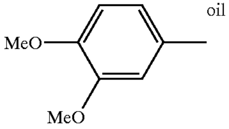 | oil |
| 13-51 | —$CH_2Me$ | 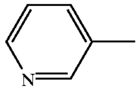 | 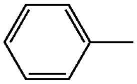 | oil |
| 13-52 | —$(CH_2)_3Me$ | 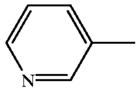 | 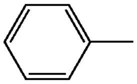 | oil |
| 13-53 | —$CH_2Me$ | 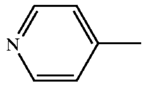 | 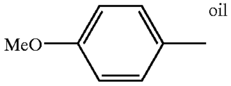 | oil |
TABLE 5
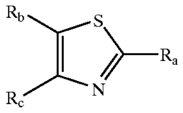
| Ref. Ex. Compd. | $R_a$ | $R_b$ | $R_c$ | mp/° C. |
|---|---|---|---|---|
| 13-54 | 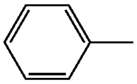 | 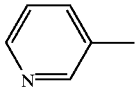 | 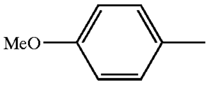 | 104–105 |
| 13-55 | —$CH_2COOH$ | 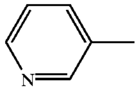 | 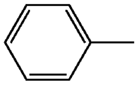 | oil |
| 13-56 | —$(CH_2)_3COOMe$ | 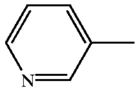 | 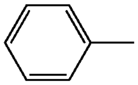 | oil |
| 13-57 | —$(CH_2)_5COOH$ | 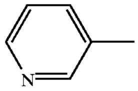 | 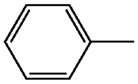 | oil |
| 13-58 | —$(CH_2)_5COOH$ | 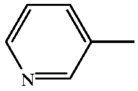 | 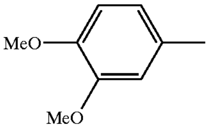 | oil |

TABLE 5-continued
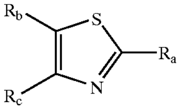
| Ref. Ex. Compd. | $R_a$ | $R_b$ | $R_c$ | mp/° C. |
|---|---|---|---|---|
| 13-59 | —$(CH_2)_4OH$ | 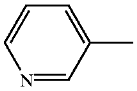 | 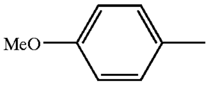 | oil |
| 13-60 | —$(CH_2)_6OH$ | 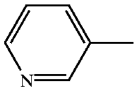 | 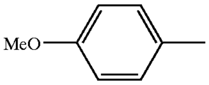 | oil |
| 13-61 | —$(CH_2)_2Me$ | 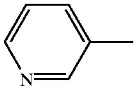 | 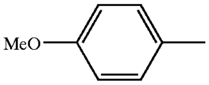 | oil |
| 13-62 | —$CHMe_2$ | 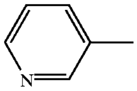 | 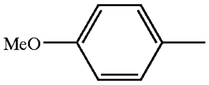 | oil |
| 13-63 | —$NMe_2$ | 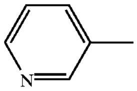 | 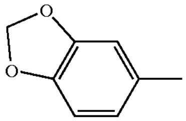 | 76–77 |
| 13-64 | —$N(CH_2Me)_2$ | 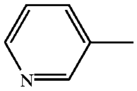 | 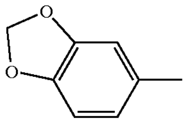 | 97–98 |
| 13-65 | —NHMe | 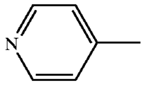 | 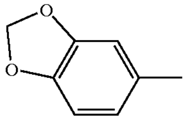 | 234–235 |
| 13-66 | —$NMe_2$ | 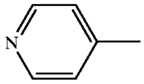 | 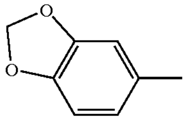 | 144–145 |
| 13-67 | —NHMe | 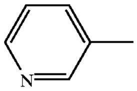 | 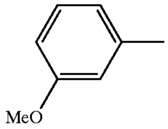 | 146–147 |
| 13-68 | —NHMe | 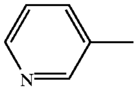 | 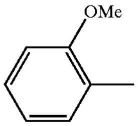 | 153–154 |
| 13-69 | —NHMe | 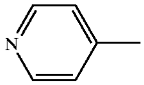 | 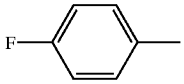 | 205–206 |

TABLE 5-continued
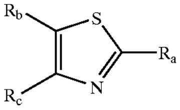
| Ref. Ex. Compd. | $R_a$ | $R_b$ | $R_c$ | mp/° C. |
|---|---|---|---|---|
| 13-70 | —NHMe | 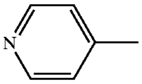 | 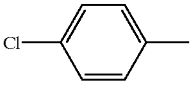 | 224–225 |
| 13-71 | —NHMe | 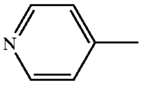 | 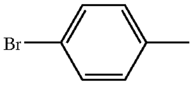 | 206–207 |
TABLE 6
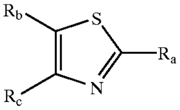
| Ref. Ex. Compd. | $R_a$ | $R_b$ | $R_c$ | Additive | mp/° C. |
|---|---|---|---|---|---|
| 13-72 | —NHMe | 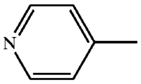 | 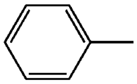 | | 191–192 |
| 13-73 | —NHMe | 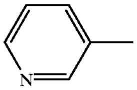 | 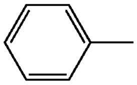 | | 168–169 |
| 13-74 | —NHMe | 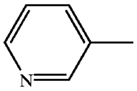 | 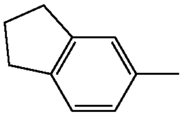 | | 172–173 |
| 13-75 | 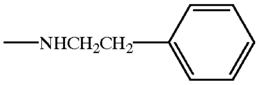 | 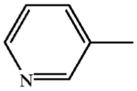 | 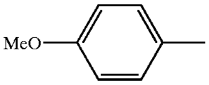 | | 126–127 |
| 13-76 | 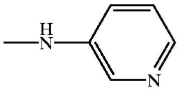 | 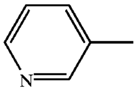 | 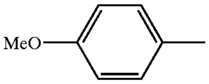 | | 222–223 |
| 13-77 | 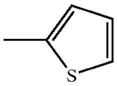 | 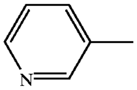 | 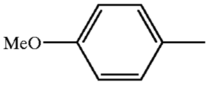 | | 132–133 |
| 13-78 | 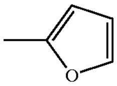 | 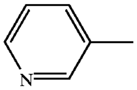 | 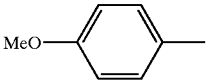 | | 90–91 |
| 13-79 | 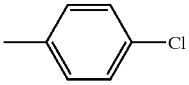 | 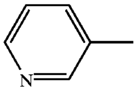 | 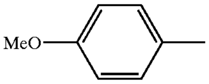 | | 148–149 |

TABLE 6-continued
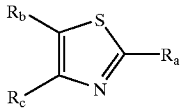
| Ref. Ex. Compd. | $R_a$ | $R_b$ | $R_c$ | Additive | mp/° C. |
|---|---|---|---|---|---|
| 13-80 | 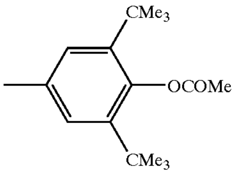 | 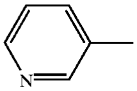 | 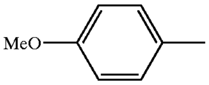 | | 180–181 |
| 13-81 | 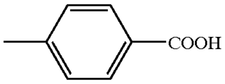 | 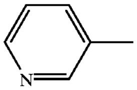 | 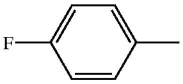 | | 240–241 |
| 13-82 | 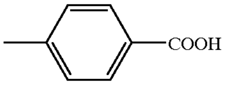 | 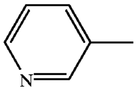 | 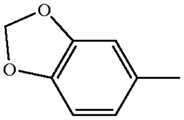 | | 258–259 |
| 13-83 | —$NMe_2$ | 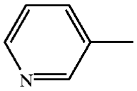 | 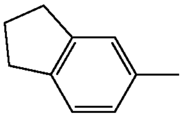 | | 85–86 |
| 13-84 | —$N(CH_2Me)_2$ | 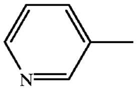 | 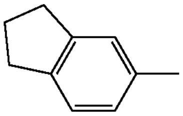 | | 56–57 |
| 13-85 | —$CH_2NH_2$ | 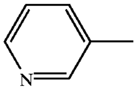 | 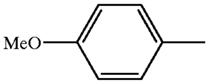 | | oil |
| 13-86 | —$CH_2NHMe$ | 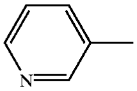 | 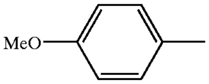 | | oil |
| 13-87 | —NHCOMe | 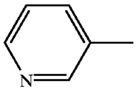 | 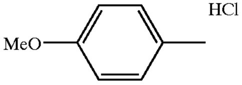 | HCl | 214–217 |
| 13-88 | —NHCOMe | 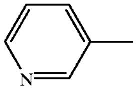 | 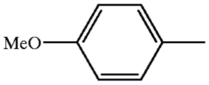 | | 228–231 |
| 13-89 | —NHCOMe | 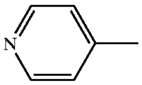 | 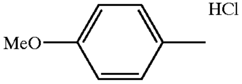 | HCl | 275–278 |
| 13-90 | —$NHCOCH_2Me$ | 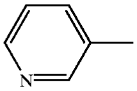 | 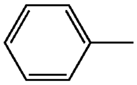 | HCl | 248–251 |

TABLE 7

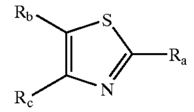

| Ref. Ex. Compd. | $R_a$ | $R_b$ | $R_c$ | mp/° C. |
|---|---|---|---|---|
| 13-91 | —$NHCOCH_2Me$ | 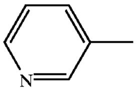 | 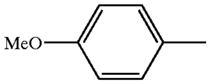 | 196–199 |
| 13-92 | —$NHCOCHMe_2$ | 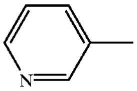 | 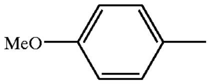 | 213–216 |
| 13-93 | —$NH_2$ | 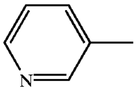 | 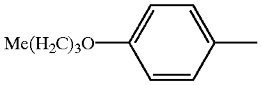 | 212–215 |
| 13-94 | —NHCOMe | 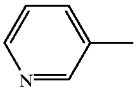 | 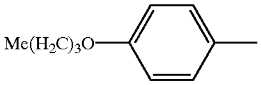 | 230–233 |
| 13-95 | —$NH_2$ | 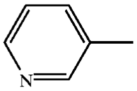 | 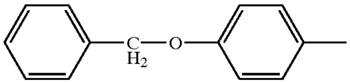 | 186–189 |
| 13-96 | —NHCOMe | 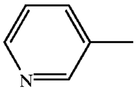 | 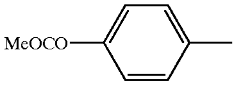 | 230–234 |
| 13-97 | 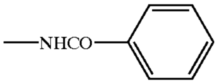 | 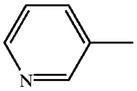 | 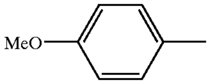 | 275–278 |
| 13-98 | —NHCOMe | 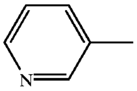 | 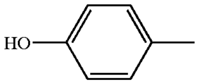 | 287–292 |
| 13-99 | —NMeCOMe | 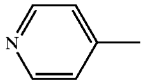 | 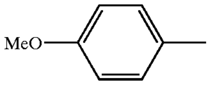 | 169–172 |
| 13-100 | —NHCOMe | 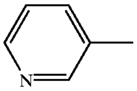 | 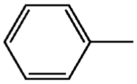 | 222–224 |
| 13-101 | —NHCOMe | 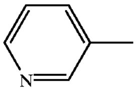 | 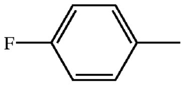 | 175–178 |
| 13-102 | —N═$CHNMe_2$ | 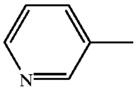 | 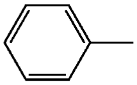 | 118–120 |

REFERENCE EXAMPLE 14

N-(4-Chlorobenzoyl)propyleneimine

A solution of propyleneimine (12.3 mL) in tetrahydrofuran (160 mL) was added to an 1N aqueous sodium hydroxide solution. To the mixture was added dropwise 4-chlorobenzoyl chloride (25 g) at 0° C. After addition, the mixture was stirred for additional 30 min. The reaction mixture was extracted with ethyl acetate. The extract was dried, concentrated under reduced pressure to afford the title compound (24.9 g, yield 89%).

oil. $^1$H-NMR ($CDCl_3$) δ: 1.39 (3H, d, J=5.5 Hz), 2.15 (1H, d, J=2.9 Hz), 2.51–2.66 (2H, m), 7.39–7.47 (2H, m), 7.93–8.01 (2H, m).

REFERENCE EXAMPLE 15

Using 3-chlorobenzoyl chloride, 2-chlorobenzoyl chloride, 2-methylbenzoyl chloride, 3-methylbenzoyl chloride, 4-methylbenzoyl chloride, 2-methoxybenzoyl chloride, 3-methoxybenzoyl chloride, 4-ethylbenzoyl chloride, 4-(1-methylethyl)benzoyl chloride, 4-(1,1-dimethylethyl)benzoyl chloride, 4-propylbenzoyl chloride, 4-butylbenzbyl chloride, 4-hexylbenzoyl chloride, 4-trifluoromethoxybenzoyl chloride, 4-trifluoromethylbenzoyl chloride, 3,4-dimethoxybenzoyl chloride, 3,4-dimethylbenzoyl chloride, 3,5-dimethylbenzoyl chloride, 3,4-methylenedioxybenzoyl chloride and 2-naphthoyl chloride instead of using 4-chlorobenzoyl chloride, the below Reference Example Compounds 15-1 to 15-20 were obtained in the same manner as described in the above Reference Example 14.

Reference Example Compound 15-1:
N-(3-Chlorobenzoyl)propyleneimine oil. $^1$H-NMR ($CDCl_3$) δ: 1.40 (3H, d, J=5.1 Hz), 2.17 (1H, d, J=3.3 Hz), 2.53–2.68 (2H, m), 7.40 (1H, dd, J=8.1, 7.7 Hz), 7.53 (1H, ddd, J=8.1, 2.2, 1.5 Hz), 7.90 (1H, dt, J=7.7, 1.5 Hz), 8.00 (1H, dd, J=2.2, 1.5 Hz).

Reference Example Compound 15-2:
N-(2-Chlorobenzoyl)propyleneimine oil. $^1$H-NMR ($CDCl_3$) δ: 1.30 (3H, d, J=5.1 Hz), 2.12 (1H, d, J=3.3 Hz), 2.53 (1H, d, J=5.5 Hz), 2.56–2.68 (1H, m), 7.28–7.48 (3H, m), 7.75–7.81 (1H, m).

Reference Example Compound 15-3:
N-(2-Methylbenzoyl)propyleneimine oil. $^1$H-NMR ($CDCl_3$) δ: 1.30 (3H, d, J=5.5 Hz), 2.08 (1H, d, J=3.3 Hz), 2.43–2.57 (5H, m), 7.20–7.31 (2H, m), 7.33–7.43 (1H, m), 7.89 (1H, d, J=7.7 Hz).

Reference Example Compound 15-4:
N-(3-Methylbenzoyl)propyleneimine oil. $^1$H-NMR ($CDCl_3$) δ: 1.39 (3H, d, J=5.5 Hz), 2.14 (1H, d, J=3.3 Hz), 2.41 (3H, s), 2.51–2.66 (2H, m), 7.32–7.39 (2H, m), 7.79–7.87 (2H, m).

Reference Example Compound 15-5:
N-(4-Methylbenzoyl)propyleneimine oil. $^1$H-NMR ($CDCl_3$) δ: 1.39 (3H, d, J=5.5 Hz), 2.12 (1H, d, J=2.9 Hz), 2.42 (3H, s), 2.50–2.62 (2H, m), 7.25 (2H, d, J=8.1 Hz), 7.92 (2H, d, J=8.1 Hz).

Reference Example Compound 15-6:
N-(2-Methoxybenzoyl)propyleneimine oil. $^1$H-NMR ($CDCl_3$) δ: 1.30 (3H, d, J=5.5 Hz), 2.10 (1H, d, J=3.3 Hz), 2.50 (1H, d, J=5.9 Hz), 2.53–2.65 (1H, m), 3.90 (3H, s), 6.95–7.05 (2H, m), 7.41–7.52 (1H, m) 7.81–7.88 (1H, m).

Reference Example Compound 15-7:
N-(3-Methoxybenzoyl)propyleneimine oil. $^1$H-NMR ($CDCl_3$) δ: 1.40 (3H, d, J=5.9 Hz), 2.14 (1H, d, J=2.9 Hz), 2.52–2.65 (2H, m), 3.86 (3H, s), 7.10 (1H, ddd, J=8.4, 2.6, 1.1 Hz), 7.37 (1H, dd, J=8.4, 7.3 Hz), 7.55 (1H, dd, J=2.6, 1.5 Hz), 7.63 (1H, ddd, J=7.3, 1.5, 1.1 Hz).

Reference Example Compound 15–8:
N-(4-Ethylbenzoyl)propyleneimine oil. $^1$H-NMR. ($CDCl_3$) δ: 1.27 (3H, t, J=7.6 Hz), 1.39 (3H, d, J=5.5 Hz), 2.13 (1H, d, J=3.3 Hz), 2.50–2.61 (2H, m), 2.71 (2H, q, J=7.6 Hz), 7.28 (2H, d, J=7.7 Hz), 7.95 (2H, d, J=7.7 Hz).

Reference Example Compound 15-9:
N-[4-(1-Methylethyl)benzoyl]propyleneimine oil. $^1$H-NMR ($CDCl_3$) δ: 1.28 (6H, d, J=7.0 Hz), 1.40 (3H, d, J=5.5 Hz), 2.13 (1H, d, J=3.3 Hz), 2.50–2.64 (2H, m), 2.90–3.05 (1H, m), 7.31 (2H, d, J=8.2 Hz), 7.96 (2H, d, J=8.2 Hz).

Reference Example Compound 15-10:
N-[4-(1,1-Dimethylethyl)benzoyl]propyleneimine oil. $^1$H-NMR ($CDCl_3$) δ: 1.35 (9H, s), 1.41 (3H, d, J=5.5 Hz), 2.12 (1H, d, J=2.9 Hz), 2.51–2.64 (2H, m), 7.47 (2H, d, J=8.8 Hz), 7.96 (2H, d, J=8.8 Hz).

Reference Example Compound 15-11:
N-(4-Propylbenzoyl)propyleneimine oil. $^1$H-NMR ($CDCl_3$) δ: 0.96 (3H, t, J=7.3 Hz), 1.39 (3H, d, J=5.5 Hz), 1.57–1.75 (2H, m), 2.12 (1H, d, J=3.3 Hz), 2.50–2.59 (2H, m), 2.65 (2H, t, J=7.7 Hz), 7.26 (2H, d, J=8.1 Hz), 7.94 (2H, d, J=8.1 Hz).

Reference Example Compound 15-12:
N-(4-Butylbenzoyl)propyleneimine oil. $^1$H-NMR ($CDCl_3$) δ: 0.94 (3H, t, J=7.1 Hz), 1.26–1.47 (5H, m), 1.54–1.73 (2H, m), 2.12 (1H, d, J=2.9 Hz), 2.51–2.62 (2H, m), 2.67 (2H, t, J=7.7 Hz), 7.26 (2H, d, J=8.1 Hz), 7.94 (2H, d, J=8.1 Hz).

Reference Example Compound 15-13:
N-(4-Hexylbenzoyl)propyleneimine oil. $^1$H-NMR ($CDCl_3$) δ: 0.89 (3H, t, J=6.6 Hz), 1.24–1.38 (6H, m), 1.39 (3H, d, J=5.5 Hz), 1.56–1.68 (2H, m), 2.12 (1H, d, J=3.3 Hz), 2.51–2.61 (2H, m), 2.66 (2H, t, J=7.7 Hz), 7.26 (2H, d, J=8.1 Hz), 7.94 (2H, d, J=8.1 Hz).

Reference Example Compound 15-14:
N-(4-Trifluoromethoxybenzoyl)propyleneimine oil. $^1$H-NMR ($CDCl_3$) δ: 1.40 (3H, d, J=5.5 Hz), 2.16 (1H, d, J=3.3 Hz), 2.53–2.68 (2H, m), 7.29 (2H, d, J=9.0 Hz), 8.08 (2H, d, J=9.0 Hz).

Reference Example Compound 15-15:
N-(4-Trifluoromethylbenzoyl)propyleneimine oil. $^1$H-NMR ($CDCl_3$) δ: 1.40 (3H, d, J=5.5 Hz), 2.19 (1H, d, J=3.7 Hz), 2.54–2.70 (2H, m), 7.73 (2H, d, J=8.0 Hz), 8.13 (2H, d, J=8.0 Hz).

Reference Example Compound 15-16:
N-(3,4-Dimethoxybenzoyl)propyleneimine oil. $^1$H-NMR ($CDCl_3$) δ: 1.41 (3H, d, J=5.5 Hz), 2.12 (1H, d, J=3.3 Hz), 2.51–2.63 (2H, m), 3.94 (3H, s), 3.95 (3H, s), 6.92 (1H, d, J=8.5 Hz), 7.56 (1H, d, J=2.2 Hz), 7.69 (1H, dd, J=8.5, 2.2 Hz).

Reference Example Compound 15-17:
N-(3,4-Dimethylbenzoyl)propyleneimine oil. $^1$H-NMR ($CDCl_3$) δ: 1.39 (3H, d, J=5.5 Hz), 2.12 (1H, d, J=3.3 Hz), 2.32 (6H, s), 2.49–2.61 (2H, m), 7.21 (1H, d, J=,7.7 Hz), 7.77 (1H, dd, J=7.7, 1.8 Hz), 7.80 (1H, d, J=1.8 Hz).

Reference Example Compound 15-18:
N-(3,5-Dimethylbenzoyl)propyleneimine oil. $^1$H-NMR ($CDCl_3$) δ: 1.39 (3H, d, J=5.5 Hz), 2.13 (1H, d, J=3.7 Hz), 2.37 (6H, s), 2.47–2.62 (2H, m), 7.19 (1H, s), 7.64 (2H, s).

Reference Example Compound 15-19:
N-(3,4-Methylenedioxybenzoyl)propyleneimine oil. $^1$H-NMR ($CDCl_3$) δ: 1.38 (3H, d, J=4.9 Hz), 2.11 (1H, d, J=3.1 Hz), 2.48–2.64 (2H, m), 6.05 (2H, s), 6.86 (1H, d, J=8.2 Hz), 7.48 (1H, d, J=1.7 Hz), 7.65 (1H, dd, J=8.2, 1.7 Hz).

Reference Example Compound 15-20:
N-(2-Naphthoyl)propyleneimine oil. $^1$H-NMR ($CDCl_3$) δ: 1.44 (3H, d, J=5.5 Hz), 2.22 (1H, d, J=3.3 Hz), 2.57–2.84 (2H, m), 7.50–7.65 (2H, m), 7.85–8.00 (3H, m), 8.06 (1H, dd, J=8.6, 1.5 Hz), 8.59 (1H, s)

REFERENCE EXAMPLE 16

1-(2-Chlorophenyl)-2-(4-pyridyl)ethanone

To a stirred solution of diisopropylamine (15.4 mL) in dry tetrahydrofuran (100 mL) cooled at −50° C., was added a solution of 1.6 M n-butyllithium in hexane (69 mL) dropwise. After addition, the resulting mixture was stirred for 10 min at the same temperature, followed by the addition of a solution of γ-picoline (20 g) in dry tetrahydrofuran (10 mL) at −30° C. After an additional 1 h stirring, a solution of N-(2-chlorobenzoyl)propyleneimine (20 g) in dry tetrahydrofuran (10 mL) was added dropwise to the resulting mixture at −10° C. After addition the mixture was stirred for another 2 h at ambient temperature. Water (100 mL) was added to the mixture and extracted with ethyl acetate. The extract was washed with water, dried, and concentrated under reduced pressure. The residue was purified using silica-gel column chromatography (hexane-ethyl acetate, 1:1) to give the title compound (16.4 g, yield 71%).

oil. $^1$H-NMR ($CDCl_3$) δ: 4.28 (2H, s), 7.20 (2H, d, J=6.2 Hz,), 7.28–7.39 (1H, m), 7.41–7.48 (3H, m), 8.56 (2H, d, J=6.2 Hz).

REFERENCE EXAMPLE 17

Using N-(3-chlorobenzoyl)propyleneimine, N-(4-chlorobenzoyl)propyleneimine, N-(2-methylbenzoyl) propyleneimine, N-(3-methylbenzoyl)propyleneimine, N-(4-methylbenzoyl)propyleneimine, N-(2-methoxybenzoyl)propyleneimine, N-(3-methoxybenzoyl) propyleneimine, N-(4-ethylbenzoyl)propyleneimine, N-(4-(1-methylethyl)benzoyl]propyleneimine, N-[4-(1,1-dimethylethyl)benzoyl]propyleneimine, N-4-(propylbenzoyl)propyleneimine, N-(4-butylbenzoyl) propyleneimine, N-(4-hexylbenzoyl)propyleneimine, N-(4-trifluoromethoxybenzoyl)propyleneimine, N-(4-trifluoromethylbenzoyl)propyleneimine, N-(3,4-dimethoxybenzoyl)propyleneimine, N-(3,4-dimethylbenzoyl)propyleneimine, N-(3,5-dimethylbenzoyl) propyleneimine, N-(3,4-methylenedioxybenzoyl) propyleneimine and N-(2-naphthoyl)propyleneimine instead of using N-(2-chlorobenzoyl)propyleneimine, the below Reference Example Compounds 17-1 to 17-20 were obtained in the same manner as described in the above Reference Example 16.

Reference Example Compound 17-1:
1-(3-Chlorophenyl)-2-(4-pyridyl)ethanone
mp 79–80° C.

Reference Example Compound 17-2:
1-(4-Chlorophenyl)-2-(4-pyridyl)ethanone
mp 93–94° C.

Reference Example Compound 17-3:
1-(2-Methylphenyl)-2-(4-pyridyl)ethanone
oil. $^1$H-NMR ($CDCl_3$) δ: 2.48 (3H, s), 4.23 (2H, s), 7.19 (2H, d, J=6.2 Hz), 7.24–7.47 (3H, m), 7.73 (1H, d, J=7.7 Hz), 8.56 (2H, d, J=6.2 Hz).

Reference Example Compound 17-4:
1-(3-Methylphenyl)-2-(4-pyridyl)ethanone
mp 115–116° C.

Reference Example Compound 17-5:
1-(4-Methylphenyl)-2-(4-pyridyl)ethanone
mp 110–111° C.

Reference Example Compound 17-6:
1(2-Methoxyphenyl)-2-(4-pyridyl)ethanone
oil. $^1$H-NMR ($CDCl_3$) δ: 3.92 (3H, s), 4.30 (2H, s), 6.95–7.07 (2H, m), 7.17 (2H, d, J=5.9 Hz), 7.50 (1H, ddd, J=8.4, 7.3, 1.8 Hz), 7.73 (1H, dd, J=7.7, 1.8 Hz), 8.53(2H, d, J=5.9 Hz).

Reference Example Compound 17-7:
1-(3-Methoxyphenyl)-2-(4-pyridyl)ethanone
oil. $^1$H-NMR ($CDCl_3$) δ: 3.86 (3H, s), 4.28 (2H, s), 7.14 (1H, ddd, J=8.1, 2.6, 1.1 Hz), 7.20 (2H, d, J=6.2 Hz) 7.36 (1H, dd, J=8.1, 7.7 Hz), 7.51 (1H, dd, J=2.6, 1.5 Hz), 7.58 (1H, ddd, J=7.7, 1.5, 1.1 Hz) 8.57 (2H, d, J=6.2 Hz).

Reference Example Compound 17-8:
1-(4-Ethylphenyl)-2-(4-pyridyl)ethanone
mp 87–89° C.

Reference Example Compound 17-9:
1-[4-(1-Methylethyl)phenyl]-2-(4-pyridyl)ethanone
mp 86–88° C.

Reference Example Compound 17-10:
1-[4-(1,1-Dimethylethyl)phenyl]-2-(4-pyridyl)ethanone
mp 75–76° C.

Reference Example Compound 17-11:
1-(4-Propylphenyl)-2-(4-pyridyl)ethanone
mp 71–72° C.

Reference Example Compound 17-12:
1-(4-Butylphenyl)-2-(4-pyridyl)ethanone
mp 41–43° C.

Reference Example Compound 17-13:
1-(4-Hexylphenyl)-2-(4-pyridyl)ethanone
mp 57–58° C.

Reference Example Compound 17-14:
2-(4-Pyridyl)-1-(4-trifluoromethoxyphenyl)ethanone
mp 65–66° C.

Reference Example Compound 17-15:
2-(4-Pyridyl)-1-(4-trifluoromethylphenyl)ethanone
mp 94–95° C.

Reference Example Compound 17-16:
1-(3,4-Dimethoxyphenyl)-2-(4-pyridyl)ethanone
mp 110–111° C.

Reference Example Compound 17-17:
1-(3,4-Dimethylphenyl)-2-(4-pyridyl)ethanone
mp 81–83° C.

Reference Example Compound 17-18:
1-(3,5-Dimethylphenyl)-2-(4-pyridyl)ethanone
mp 90–91° C.

Reference Example Compound 17-19:
1-(3,4-Methylenedioxyphenyl)-2-(4-pyridyl)ethanone
mp 126–127° C.

Reference Example Compound 17-20:
1-(2-Naphthyl)-2-(4-pyridyl)ethanone
mp 114–115° C.

REFERENCE EXAMPLE 18

Using α-picoline instead of using γ-picoline, the below Reference Example Compounds 18-1 to 18-9 were obtained in the same manner as described in the above Reference Example 17.

Reference Example Compound 18-1:
1-(2-Chlorophenyl)-2-(3-pyridyl)ethanone
oil. $^1$H-NMR ($CDCl_3$) δ: 4.28 (2H, s), 7.18–7.49 (5H, m), 7.59–7.67(1H, m), 8.47–8.56 (2H, m).

Reference Example Compound 18-2:
1-(3-Chlorophenyl)-2-(3-pyridyl)ethanone
oil. $^1$H-NMR ($CDCl_3$) δ: 4.29 (2H, s), 7.25–7.34 (1H, m), 7.44 (1H, t, J=7.7 Hz), 7.54–7.63 (2H, m), 7.90 (1H, dt, J=7.7, 1.5 Hz), 8.00 (1H, dd, J=1.8, 1.5 Hz), 8.49–8.57 (2H, m).

Reference Example Compound 18-3:
1-(4-Chlorophenyl)-2-(3-pyridyl)ethanone
$^1$H-NMR ($CDCl_3$) δ: 4.27 (2H, s), 7.24–7.31 (1H, m), 7.47 (2H, d, J=8.8 Hz), 7.55–7.63 (1H, m), 7.96 (2H, d, J=8.8 Hz), 8.46–8.53 (2H, m).

Reference Example Compound 18-4:
1-(2-Methylphenyl)-2-(3-pyridyl)ethanone
oil. $^1$H-NMR ($CDCl_3$) δ: 2.47 (3H, s), 4.23 (2H, s), 7.18–7.47 (5H, m), 7.73 (1H, d, J=7.7 Hz), 8.47–8.56 (2H, m).

Reference Example Compound 18-5:
1-(3-Methylphenyl)-2-(3-pyridyl)ethanone oil. $^1$H-NMR ($CDCl_3$) δ: 2.43 (3H, s), 4.29 (2H, s), 7.17–7.36 (1H, m), 7.36–7.46 (2H, m), 7.58–7.65 (1H, m), 7.78–7.86 (2H, m), 8.50–8.56 (2H, m).

Reference Example Compound 18-6:
1-(4-Methylphenyl)-2-(3-pyridyl)ethanone mp 72–74° C.

Reference Example Compound 18-7:
1-(3-Methoxyphenyl)-2-(3-pyridyl)ethanone oil. $^1$H-NMR ($CDCl_3$) δ: 3.86 (3H, s), 4.29 (2H, s), 7.14 (1H, ddd, J=8.1, 2.6, 1.8 Hz), 7.28 (1H, dd, J=7.3, 4.8 Hz), 7.40 (1H, dd, J=8.1, 7.7 Hz), 7.53 (1H, dd, J=2.6, 1.8 Hz), 7.58–7.65 (2H, m), 8.50–8.55 (2H, m).

Reference Example Compound 18-8:
1-[4-(1,1-Dimethylethyl)phenyl]-2-(3-pyridyl)ethanone oil. $^1$H-NMR ($CDCl_3$) δ: 1.34 (9H, s), 4.28 (2H, s), 7.22–7.31 (1H, m), 7.50 (2H, d, J=8.4 Hz), 7.56–7.65 (1H, m), F 7.96 (2H, d, J=8.4 Hz), 8.48–8.55 (2H, m).

Reference Example Compound 18-9:
1-(3,5-Dimethylphenyl)-2-(3-pyridyl)ethanone oil. $^1$H-NMR ($CDCl_3$) δ: 2.38 (6H, s), 4.27 (2H, s), 7.24–7.30 (2H, m), 7.58–7.63 (3H, m), 8.50–8.52 (2H, m).

REFERENCE EXAMPLE 19

Using ethyl 4-dimethylaminobenzoate instead of using ethyl p-anisate, the below Reference Example Compound 19 was obtained in the same manner as described in the above Reference Example 1.

Reference Example Compound 19:
1-(4-Dimethylaminophenyl)-2-(4-pyridyl)ethanone mp 189–192° C.

REFERENCE EXAMPLE 20

2-[4-(1,1-Dimethylethyl)phenyl]-1-(4-pyridyl)ethanone

To a solution of ethyl isonicotinate (12 g) and 4-(1,1-Dimethylethyl)phenylacetonitrile (9.1 g) in tert-butyl alcohol (36 mL), was added potassium tert-butoxide (7.3 g), and the mixture was stirred at 100° C. for 3 h. After cooling, the resulting mixture was dissolved in water and washed with isopropyl ether. The aqueous phase was adjusted to pH 7.0 with 2 N hydrochloric acid and extracted with ethyl acetate. The extract was washed with water, dried, And the solvent was evaporated. The crystalline residue was recrystallized from ethyl acetate-isopropyl ether to obtain 2-cyano-2-[4-(1,1-dimethylethyl)phenyl]-1-(4-pyridyl)ethanone (5.09 g, yield 35%).

2-Cyano-2-[4-(1,1-dimethylethyl)phenyl]-1-(4-pyridyl) ethanone (5.0 g) obtained above was dissolved in 48% hydrobromic acid (50 mL) and the solution was stirred at 140° C. for 5 h. After the mixture was cooled, the mixture was neutralized with an aqueous saturated solution of sodium hydrogen carbonate and the product was extracted with ethyl acetate. The extract was washed with water, dried, and the solvent was evaporated. The residue was purified using silica-gel column chromatography (hexane-ethyl acetate, 1:1) to obtain the title compound (3.1 g, yield 68%).

oil $^1$H-NMR ($CDCl_3$) δ: 1.30 (9H, s), 4.25 (2H, s), 7.18 (2H, d, J=8.4 Hz), 7.36 (2H, d, J=8.4 Hz), 7.78 (2H, d, J=6.2 Hz), 8.81 (2H, d, J=6.2 Hz).

REFERENCE EXAMPLE 21

2-(3,5-Dimethylphenyl)-1-(4-pyridyl)ethanone

Using 3,5-dimethylphenylacetonitrile instead of using 4-(1,1-Dimethylethyl)phenylacetonitrile, the title compound was obtained in the same manner as described in the above Reference Example 20.

mp 96–97C.

REFERENCE EXAMPLE 22

Using 1-(2-chlorophenyl)-2-(3-pyridyl)ethanone, 1-(3-chlorophenyl)-2-(3-pyridyl)ethanone, 1-(4-chlorophenyl)-2-(3-pyridyl)ethanone, 1-(2-methylphenyl)-2-(3-pyridyl) ethanone, 1-(3-methylphenyl)-2-(3-pyridyl)ethanone, 1-(4-methylphenyl)-2-(3-pyridyl)ethanone, 1-(3-methoxyphenyl)-2-(3-pyridyl)ethanone, 1-[4-(1,1-dimethylethyl)phenyl]-2-(3-pyridyl)ethanone, 1-(3,5-dimethylphenyl)-2-(3-pyridyl)ethanone, 1-(2-chlorophenyl)-2-(4-pyridyl)ethanone, 1-(3-chlorophenyl)-2-(4-pyridyl)ethanone, 1-(4-chlorophenyl)-2-(4-pyridyl) ethanone, 1-(2-methylphenyl)-2-(4-pyridyl)ethanone, 1-(3-methylphenyl)-2-(4-pyridyl)ethanone, 1-(4-methylphenyl)-2-(4-pyridyl)ethanone, 1-(2-methoxyphenyl)-2-(4-pyridyl) ethanone, 1-(3-methoxyphenyl)-2-(4-pyridyl)ethanone, 1-(4-ethylphenyl)-2-(4-pyridyl)ethanone, 1-[4-(1-methylethyl)phenyl]-2-(4-pyridyl)ethanone, 1-[4-(1,1-dimethylethyl)phenyl]-2-(4-pyridyl)ethanone, 1-(4-propylphenyl)-2-(4-pyridyl)ethanone, 1-(4-butylphenyl)-2-(4-pyridyl)ethanone, 1-(4-hexylphenyl)-2-(4-pyridyl) ethanone, 2-(4-pyridyl)-1-(4-trifluoromethoxyphenyl) ethanone, 2-(4-pyridyl)-1-(4-trifluoromethylphenyl) ethanone, 1-(4-dimethylaminophenyl)-2-(4-pyridyl) ethanone hydrobromide, 1-(3,4-dimethoxyphenyl)-2-(4-pyridyl)ethanone, 1-(3,4-dimethylphenyl)-2-(4-pyridyl) ethanone, 1-(3,5-dimethylphenyl)-2-(4-pyridyl)ethanone, 1-(3,4-methylenedioxyphenyl)-2-(4-pyridyl)ethanone, 1-(2-naphthyl)-2-(4-pyridyl)ethanone, 2-[4-(1,1-dimethylethyl) phenyl]-1-(4-pyridyl)ethanone and 2-(3,5-dimethylphenyl)-1-(4-pyridyl)ethanone instead of using 1-(4-methoxyphenyl)-2-(3-pyridyl)ethanone, the below Reference Example Compounds 22-1 to 22-33 were obtained in the same manner as described in the above Reference Example 6.

Reference Example Compound 22-1:
2-Bromo-1-(2-chlorophenyl)-2-(3-pyridyl)ethanone Hydrobromide mp 88–90° C.

Reference Example Compound 22-2:
2-Bromo-1-(3-chlorophenyl)-2-(3-pyridyl)ethanone Hydrobromide mp 164–166° C.

Reference Example Compound 22-3:
2-Bromo-1-(4-chlorophenyl)-2-(3-pyridyl)ethanone Hydrobromide The crude mixture without purification was used in the next reaction.

Reference Example Compound 22-4:
2-Bromo-1-(2-methylphenyl)-2-(3-pyridyl)ethanone Hydrobromide The crude mixture without purification was used in the next reaction.

Reference Example Compound 22-5:
2-Bromo-1-(3-methylphenyl)-2-(3-pyridyl)ethanone Hydrobromide The crude mixture without purification was used in the next reaction.

Reference Example Compound 22-6:
2-Bromo-1-(4-methylphenyl)-2-(3-pyridyl)ethanone Hydrobromide mp 96–98° C.

Reference Example Compound 22-7:
2-Bromo-1-(3-methoxyphenyl)-2-(3-pyridyl)ethanone Hydrobromide The crude mixture without purification was used to next reaction.

Reference Example Compound 22-8:
2-Bromo-1-[4-(1,1-dimethylethyl)phenyl]-2-(3-pyridyl) ethanone Hydrobromide mp 190–194° C.

Reference Example Compound 22-9:
2-Bromo-1-(3,5-dimethylphenyl)-2-(3-pyridyl)ethanone Hydrobromide mp 195–197° C.

Reference Example Compound 22-10:
2-Bromo-1-(2-chlorophenyl)-2-(4-pyridyl)ethanone Hydrobromide mp 157–159° C.

Reference Example Compound 22-11:
2-Bromo-1-(3-chlorophenyl)-2-(4-pyridyl)ethanone Hydrobromide mp 178–181° C.

Reference Example Compound 22-12:
2-Bromo-1-(4-chlorophenyl)-2-(4-pyridyl)ethanone Hydrobromide mp 189–193° C.

Reference Example Compound 22-13:
2-Bromo-1-(2-methylphenyl)-2-(4-pyridyl)ethanone Hydrobromide mp 183–186° C.

Reference Example Compound 22-14:
2-Bromo-1-(3-methylphenyl)-2-(4-pyridyl)ethanone Hydrobromide The crude mixture without purification was used to next reaction.

Reference Example Compound 22-15:
2-Bromo-1-(4-methylphenyl)-2-(4-pyridyl)ethanone Hydrobromide mp 111–113° C.

Reference Example Compound 22-16:
2-Bromo-1-(2-methoxyphenyl)-2-(4-pyridyl)ethanone Hydrobromide mp 168–171° C.

Reference Example Compound 22-17:
2-Bromo-1-(3-methoxyphenyl)-2-(4-pyridyl)ethanone Hydrobromide The crude mixture without purification was used t next reaction.

Reference Example Compound 22-18:
2-Bromo-1-(4-ethylphenyl)-2-(4-pyridyl)ethanone Hydrobromide mp 170–173° C.

Reference Example Compound 22-19:
2-Bromo-1-[4-(1-methylethyl)phenyl]-2-(4-pyridyl) ethanone Hydrobromide mp 185–188° C.

Reference Example Compound 22-20:
2-Bromo-1-[4-(1,1-dimethylethyl)phenyl]-2-(4-pyridyl) ethanone Hydrobromide mp 209–212° C.

Reference Example Compound 22-21:
2-Bromo-1-(4-propylphenyl)-2-(4-pyridyl)ethanone Hydrobromide mp 167–170° C.

Reference Example Compound 22-22:
2-Bromo-1-(4-butylphenyl)-2-(4-pyridyl)ethanone Hydrobromide mp 158–161° C.

Reference Example Compound 22-23:
2-Bromo-1-(4-hexylphenyl)-2-(4-pyridyl)ethanone Hydrobromide mp 153–155° C.

Reference Example Compound 22-24:
2-Bromo-2-(4-pyridyl)-1-(4-trifluoromethoxyphenyl) ethanone Hydrobromide The crude mixture without purification was used to next reaction.

Reference Example Compound 22-25:
2-Bromo-2-(4-pyridyl)-1-(4-trifluoromethylphenyl) ethanone Hydrobromide mp 190–194° C.

Reference Example Compound 22-26:
2-Bromo-1-(4-dimethylaminophenyl)-2-(4-pyridyl) ethanone Dihydrobromide mp 163–167° C.

Reference Example Compound 22-27:
2-Bromo-1-(3,4-dimethoxyphenyl)-2-(4-pyridyl)ethanone Hydrobromide mp 174–175° C.

Reference Example Compound 22-28:
2-Bromo-1-(3,4-dimethylphenyl)-2-(4-pyridyl)ethanone Hydrobromide mp 196–199° C.

Reference Example Compound 22-29:
2-Bromo-1-(3,5-dimethylphenyl)-2-(4-pyridyl)ethanone Hydrobromide mp 216–219° C.

Reference Example Compound 22-30:
2-Bromo-1-(3,4-methylenedioxyphenyl)-2-(4-pyridyl) ethanone Hydrobromide mp 211–214° C.

Reference Example Compound 22-31:
2-Bromo-1-(2-naphthyl)-2-(4-pyridyl)ethanone Hydrobromide mp 149–152° C.

Reference Example Compound 22-32:
2-Bromo-2-[4-(1,1-dimethylethyl)phenyl]-1-(4-pyridyl) ethanone Hydrobromide The crude mixture without purification was used in the next reaction.

Reference Example Compound 22-33:
2-Bromo-2-(3,5-dimethylphenyl)-1-(4-pyridyl)ethanone Hydrobromide mp 186–188° C.

REFERENCE EXAMPLE 23

The following Reference Example Compounds 23-1 to 23-222 shown in Tables 8 to 21 were obtained in the same manner as described in the above References 5 to 9, JP-A-61-10580 and U.S. Pat. No. 4,612,321.

TABLE 8
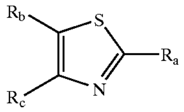
| Ref. Ex. Compd. | $R_a$ | $R_b$ | $R_c$ | Additive | mp/° C. |
|---|---|---|---|---|---|
| 23-1 | 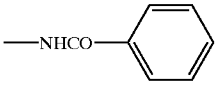 | 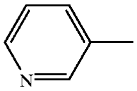 | 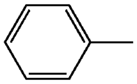 | HCl | 260 |
| 23-2 | 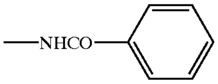 | 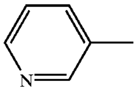 | 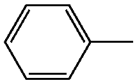 | HCl | 244–246 |
| 23-3 | 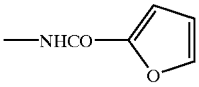 | 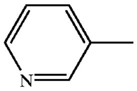 | 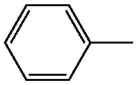 | HCl | 255–256 |
| 23-4 | 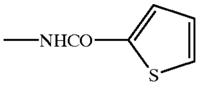 | 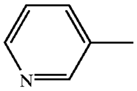 | 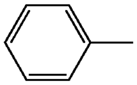 | HCl | 275 |
| 23-5 | 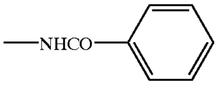 | 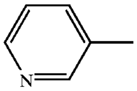 | 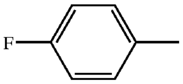 | | 233 |
| 23-6 | —NHCOMe | 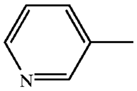 | 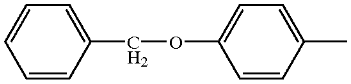 | | 218–220 |
| 23-7 | —NHCOMe | | 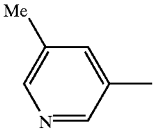 | 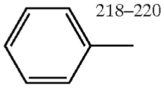 | 218–220 |
| 23-8 | 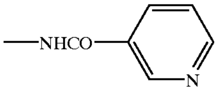 | 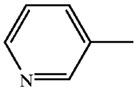 | 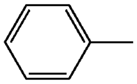 | 2HCl | 145–148 |
| 23-9 | 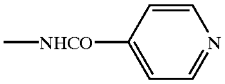 | 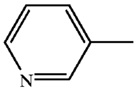 | 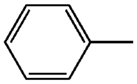 | | 238 |
| 23-10 | 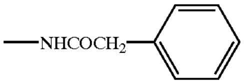 | 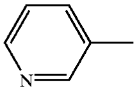 | 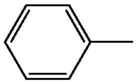 | | 228–230 |
| 23-11 | 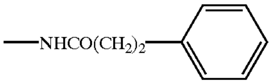 | 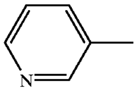 | 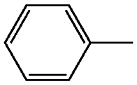 | | 215–217 |
| 23-12 | —NHCO($CH_2$)$_2$Me | 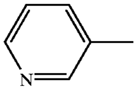 | 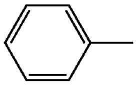 | | 198–200 |
| 23-13 | —NHCO($CH_2$)$_3$Me | 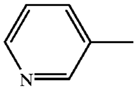 | 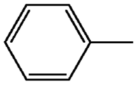 | | 205–206 |

TABLE 8-continued
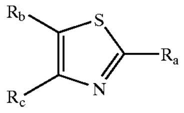
| Ref. Ex. Compd. | $R_a$ | $R_b$ | $R_c$ | Additive | mp/° C. |
|---|---|---|---|---|---|
| 23-14 | $—NHCO(CH_2)_4Me$ | 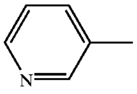 | 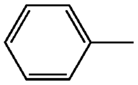 | | 175–177 |
| 23-15 | $—NHCOCMe_3$ | 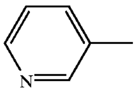 | 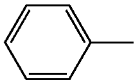 | | 219–220 |
| 23-16 | 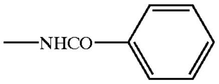 | 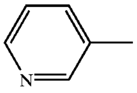 | 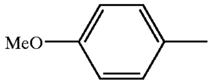 | HCl | 268–270 |
| 23-17 | 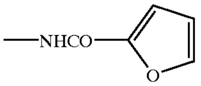 | 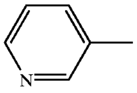 | 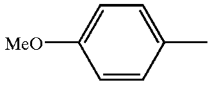 | HCl | 243–246 |
TABLE 9
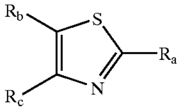
| Ref. Ex. Compd. | $R_a$ | $R_b$ | $R_c$ | Additive | mp/° C. |
|---|---|---|---|---|---|
| 23-18 | 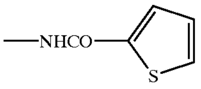 | 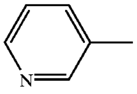 | 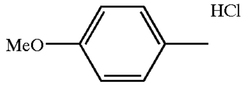 | HCl | 237–239 |
| 23-19 | 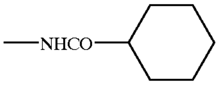 | 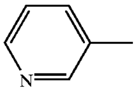 | 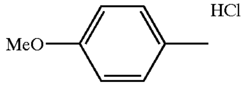 | HCl | 220–223 |
| 23-20 | 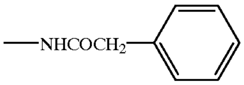 | 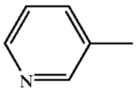 | 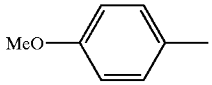 | | 184–185 |
| 23-21 | 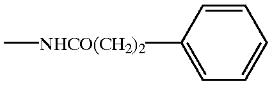 | 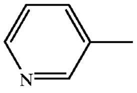 | 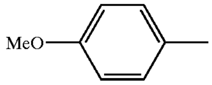 | | 214–216 |
| 23-22 | $—NHCO(CH_2)_2Me$ | 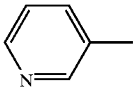 | 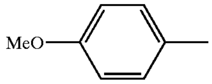 | | 197–198 |
| 23-23 | $—NHCO(CH_2)_3Me$ | 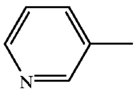 | 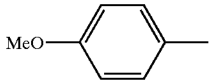 | | 188–190 |

TABLE 9-continued
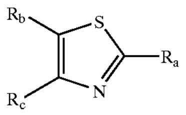
| Ref. Ex. Compd. | $R_a$ | $R_b$ | $R_c$ | Additive | mp/° C. |
|---|---|---|---|---|---|
| 23-24 | $—NHCO(CH_2)_4Me$ | 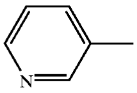 | 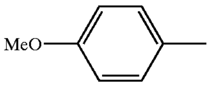 | | 167–169 |
| 23-25 | $—NHCOCMe_3$ | 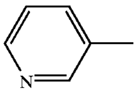 | 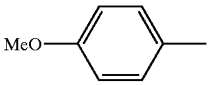 | | 245–246 |
| 23-26 | 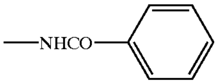 | 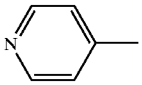 | 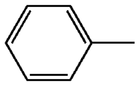 | | 237–238 |
| 23-27 | 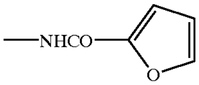 | 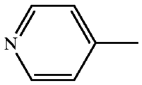 | 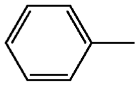 | | 240 |
| 23-28 | 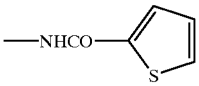 | 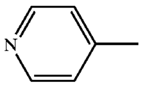 | 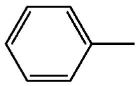 | | 240 |
| 23-29 | 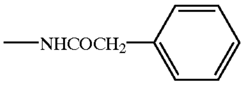 | 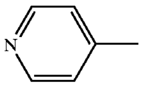 | 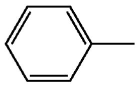 | | 233–234 |
| 23-30 | 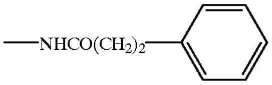 | 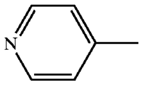 | 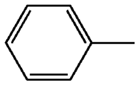 | | 214–216 |
| 23-31 | $—NHCOCMe_3$ | 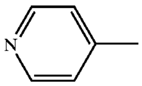 | 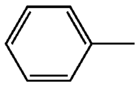 | | 206–208 |
| 23-32 | 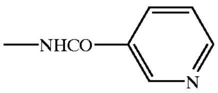 | 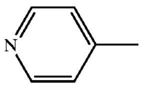 | 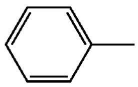 | | 247 |
| 23-33 | $—NHCO(CH_2)_2Me$ | 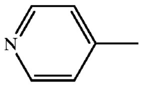 | 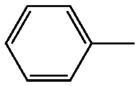 | | 212–214 |
| 23-34 | $—NHCO(CH_2)_3Me$ | 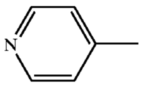 | 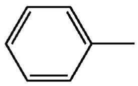 | | 232–234 |
| 23-35 | $—NHCO(CH_2)_4Me$ | 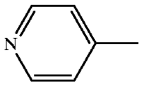 | 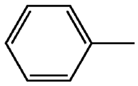 | | 245–246 |

TABLE 10
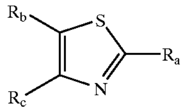
| Ref. Ex. Compd. | $R_a$ | $R_b$ | $R_c$ | mp/° C. |
|---|---|---|---|---|
| 23-36 | 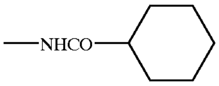 | 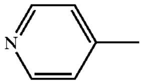 | 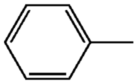 | 219–220 |
| 23-37 | —$NHCOCH_2Me$ | 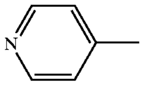 | 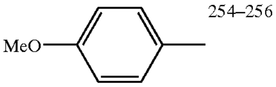 | 254–256 |
| 23-38 | 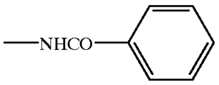 | 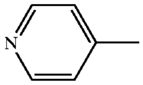 | 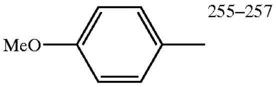 | 255–257 |
| 23-39 | —$NH_2$ | 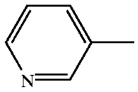 | 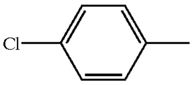 | 278–280 |
| 23-40 | —NHCOMe | 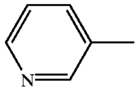 | 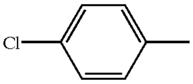 | 266–268 |
| 23-41 | —$NHCOCH_2Me$ | 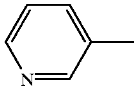 | 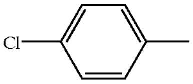 | 241–242 |
| 23-42 | —$NH_2$ | 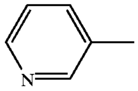 | 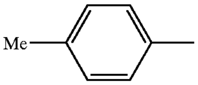 | 286–288 |
| 23-43 | —NHCOMe | 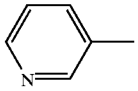 | 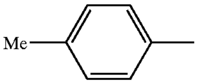 | 260–261 |
| 23-44 | —$NHCOCH_2Me$ | 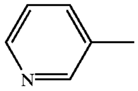 | 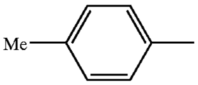 | 226–227 |
| 23-45 | —NHCOMe | 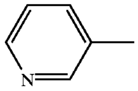 | 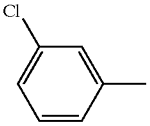 | 217–219 |
| 23-46 | —$NHCOCH_2Me$ | 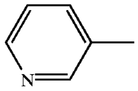 | 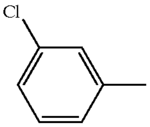 | 228–229 |
| 23-47 | —NHCOMe | 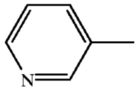 | 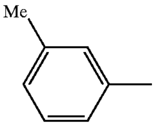 | 235–236 |

TABLE 10-continued
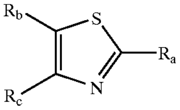
| Ref. Ex. Compd. | $R_a$ | $R_b$ | $R_c$ | mp/° C. |
|---|---|---|---|---|
| 23-48 | —$NHCOCH_2Me$ | 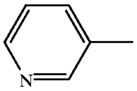 | 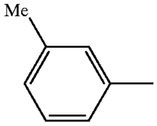 | 239–241 |
| 23-49 | —NHCOMe | 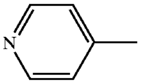 | 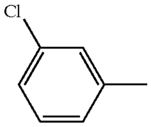 | 290–293 |
| 23-50 | —$NHCOCH_2Me$ | 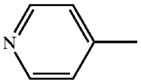 | 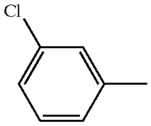 | 289–290 |
| 23-51 | —NHCOMe | 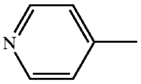 | 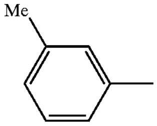 | 287–289 |
TABLE 11
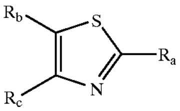
| Ref. Ex. Compd. | $R_a$ | $R_b$ | $R_c$ | mp/° C. |
|---|---|---|---|---|
| 23-52 | —$NHCCCH_2Me$ | 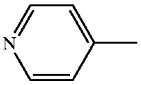 | 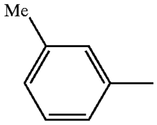 | 258–260 |
| 23-53 | —NHCOMe | 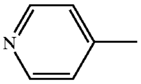 | 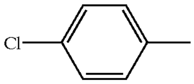 | 317–320 |
| 23-54 | —$NHCOCH_2Me$ | 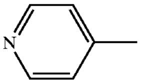 | 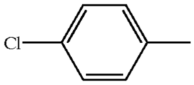 | 257–259 |
| 23-55 | —NHCOMe | 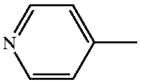 | 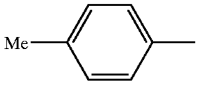 | 308–309 |

TABLE 11-continued
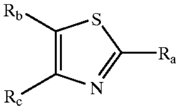
| Ref. Ex. Compd. | $R_a$ | $R_b$ | $R_c$ | mp/° C. |
|---|---|---|---|---|
| 23-56 | —$NHCOCH_2Me$ | 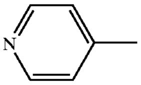 | 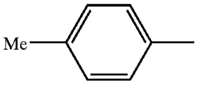 | 249–250 |
| 23-57 | —$NH_2$ | 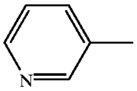 | 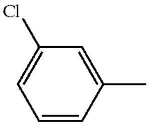 | 228–230 |
| 23-58 | —$NH_2$ | 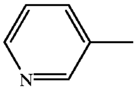 | 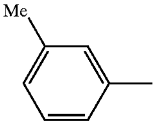 | 231–232 |
| 23-59 | —$NH_2$ | 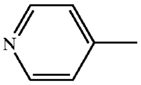 | 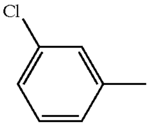 | 256–258 |
| 23-60 | —$NH_2$ | 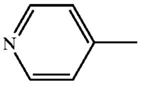 | 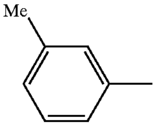 | 255–258 |
| 23-61 | —$NH_2$ | 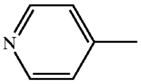 | 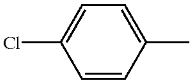 | >300 |
| 23-62 | —$NH_2$ | 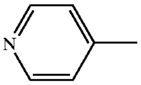 | 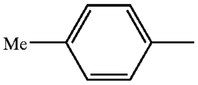 | 296–298 |
| 23-63 | —N═C(Me)$NMe_2$ | 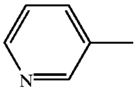 | 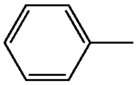 | 129–131 |
| 23-64 | —NHCOMe | 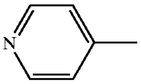 | 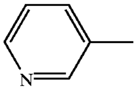 | 282–284 |
| 23-65 | —NHCOMe | 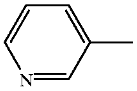 | 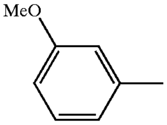 | 236–239 |
| 23-66 | —$NHCOCH_2Me$ | 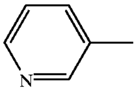 | 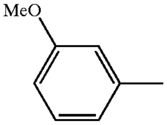 | 222–224 |

TABLE 11-continued
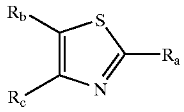
| Ref. Ex. Compd. | $R_a$ | $R_b$ | $R_c$ | mp/° C. |
|---|---|---|---|---|
| 23-67 | 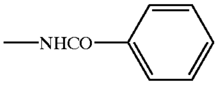 | 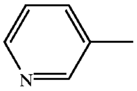 | 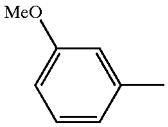 | 236–239 |
TABLE 12
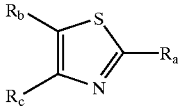
| Ref. Ex. Compd. | $R_a$ | $R_b$ | $R_c$ | mp/° C. |
|---|---|---|---|---|
| 23-68 | —NHCOMe | 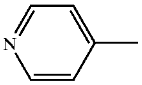 | 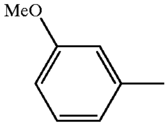 | 234–236 |
| 23-69 | —$NHCOCH_2Me$ | 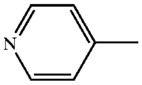 | 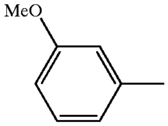 | 237–239 |
| 23-70 | 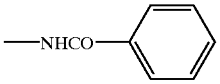 | 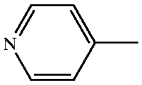 | 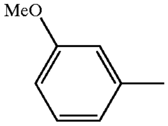 | 220–222 |
| 23-71 | —NHCOMe | 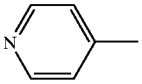 | 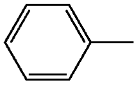 | 294–297 |
| 23-72 | —$NHCOCH_2Me$ | 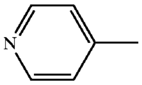 | 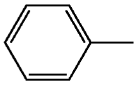 | 267–269 |
| 23-73 | —$N(CH_2Me)COMe$ | 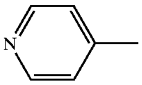 | 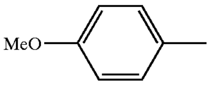 | 143–144 |
| 23-74 | —$N((CH_2)_4Me)COMe$ | 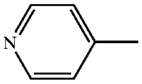 | 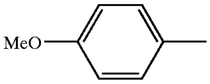 | 111–113 |
| 23-75 | 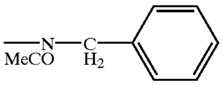 | 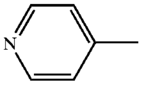 | 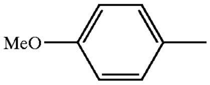 | 162–164 |

TABLE 12-continued
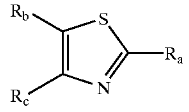
| Ref. Ex. Compd. | $R_a$ | $R_b$ | $R_c$ | mp/° C. |
|---|---|---|---|---|
| 23-76 | —$NH_2$ | 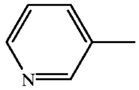 | 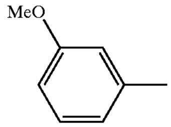 | 206–209 |
| 23-77 | —$NH_2$ | 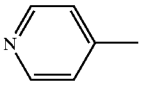 | 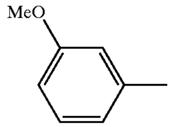 | 232–234 |
| 23-78 | —$NH_2$ | 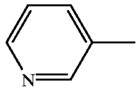 | 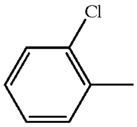 | 236–239 |
| 23-79 | —$NH_2$ | 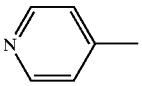 | 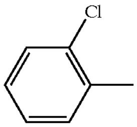 | 232–235 |
| 23-80 | 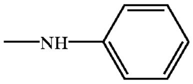 | 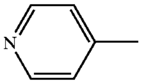 | 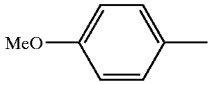 | 287–289 |
| 23-81 | 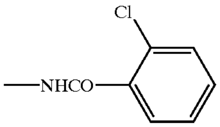 | 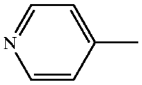 | 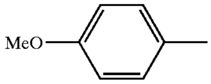 | 330–333 |
| 23-82 | 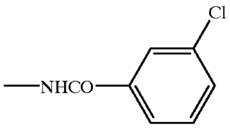 | 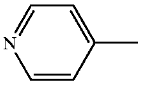 | 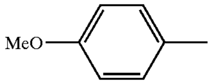 | 292–294 |
TABLE 13
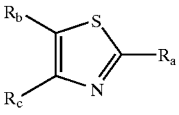
| Ref. Ex. Compd. | $R_a$ | $R_b$ | $R_c$ | mp/° C. |
|---|---|---|---|---|
| 23-83 | 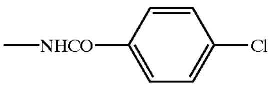 | 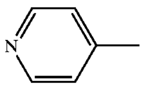 | 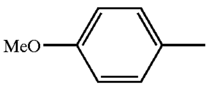 | 346–348 |

TABLE 13-continued
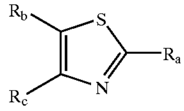
| Ref. Ex. Compd. | $R_a$ | $R_b$ | $R_c$ | mp/° C. |
|---|---|---|---|---|
| 23-84 | 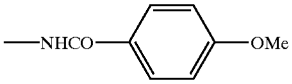 | 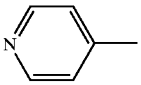 | 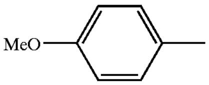 | 308–310 |
| 23-85 | —$NH_2$ | 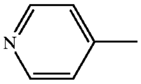 | 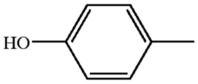 | 323–326 |
| 23-86 | —NHCOMe | 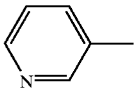 | 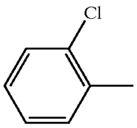 | 259–261 |
| 23-87 | —NHCOMe | 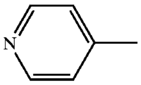 | 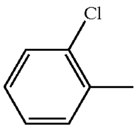 | 292–293 |
| 23-88 | 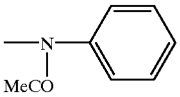 | 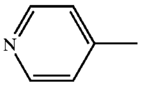 | 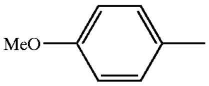 | 161–163 |
| 23-89 | —$NH_2$ | 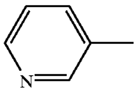 | 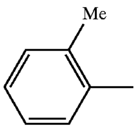 | 235–237 |
| 23-90 | —NHCOMe | 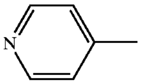 | 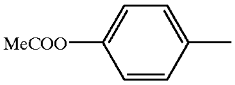 | 254–257 |
| 23-91 | 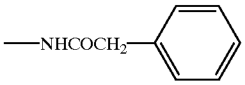 | 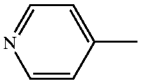 | 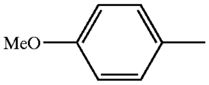 | 274–277 |
| 23-92 | —NHCOMe | 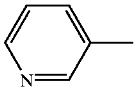 | 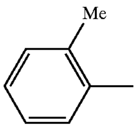 | 237–239 |
| 23-93 | —NHCOMe | 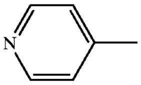 | 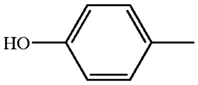 | 285–287 |
| 23-94 | —$NH_2$ | 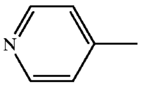 | 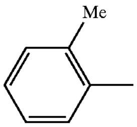 | 235—238 |

TABLE 13-continued
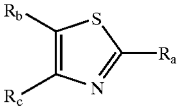
| Ref. Ex. Compd. | $R_a$ | $R_b$ | $R_c$ | mp/° C. |
|---|---|---|---|---|
| 23-95 | —NHCOMe | 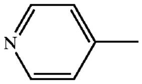 | 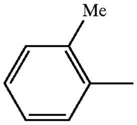 | 272–274 |
| 23-96 | —$NH_2$ | 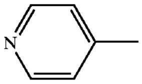 | 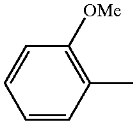 | 213–215 |
| 23-97 | —NHCOMe | 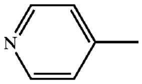 | 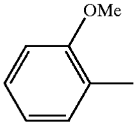 | 259–261 |
| 23-98 | —$NHCO(CH_2)_4Cl$ | 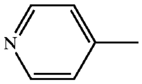 | 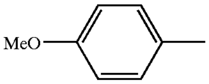 | 228–229 |
TABLE 14
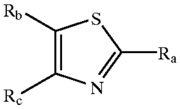
| Ref. Ex. Compd. | $R_a$ | $R_b$ | $R_c$ | mp/° C. |
|---|---|---|---|---|
| 23-99 | —NHCOMe | 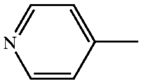 | 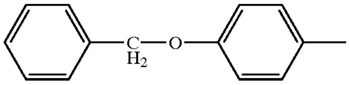 | 254–257 |
| 23-100 | 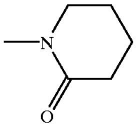 | 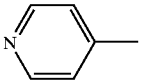 | 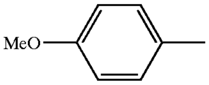 | 159–160 |
| 23-101 | 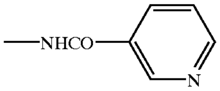 | 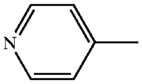 | 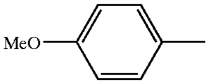 | 278–281 |
| 23-102 | 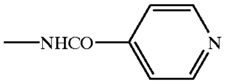 | 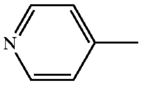 | 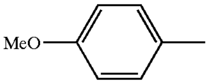 | 295–297 |
| 23-103 | 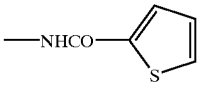 | 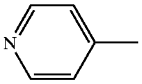 | 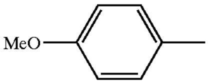 | 262–264 |

TABLE 14-continued
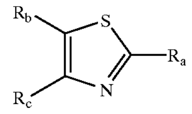
| Ref. Ex. Compd. | $R_a$ | $R_b$ | $R_c$ | mp/° C. |
|---|---|---|---|---|
| 23-104 | 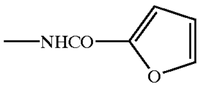 | 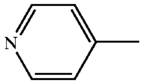 | 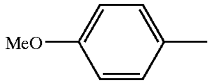 | 266–269 |
| 23-105 | —NHCOCHMe$_2$ | 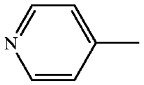 | 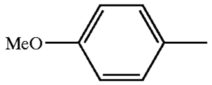 | 227–230 |
| 23-106 | —NHCOCMe$_3$ | 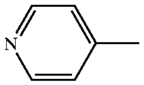 | 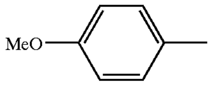 | 254–256 |
| 23-107 | —NHCOCH$_2$CHMe$_2$ | 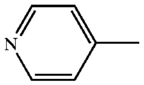 | 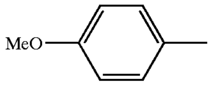 | 261–262 |
| 23-108 | —NHCONH(CH$_2$)$_2$Me | 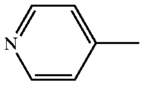 | 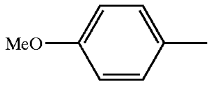 | 215–219 |
| 23-109 | —NH$_2$ | 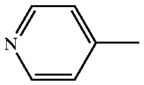 | 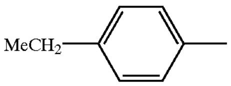 | 285–288 |
| 23-110 | —NHCOMe | 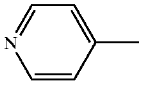 | 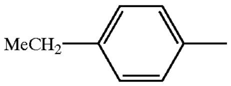 | 294–295 |
| 23-111 | —NHCOMe | 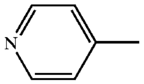 | 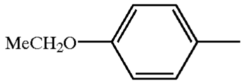 | 206–209 |
| 23-112 | —NHCOMe | 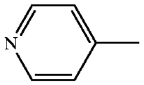 | 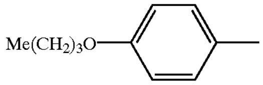 | 201–203 |
| 23-113 | —NHCOMe | 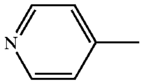 | 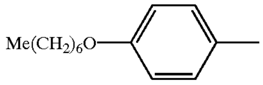 | 210–212 |
| 23-114 | —NHCO(CH$_2$)$_3$Cl | 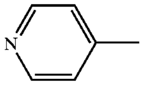 | 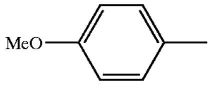 | 191–194 |
| 23-115 | 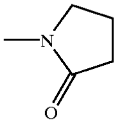 | 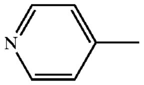 | 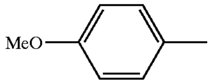 | 133–135 |

TABLE 15
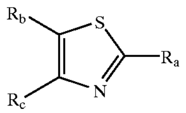
| Ref. Ex. Compd. | $R_a$ | $R_b$ | $R_c$ | mp/° C. |
|---|---|---|---|---|
| 23-116 | —$NHCO(CH_2)_5Cl$ | 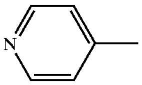 | 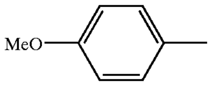 | 223–225 |
| 23-117 | 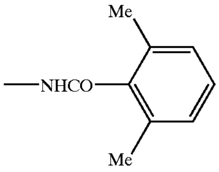 | 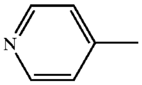 | 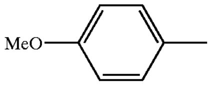 | 351–352 |
| 23-118 | —NHCOMe | 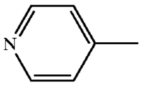 | 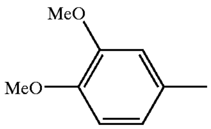 | 265–267 |
| 23-119 | —NHCOMe | 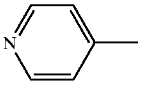 | 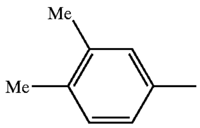 | 248–250 |
| 23-120 | —NHCOMe | 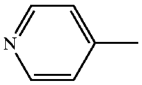 | 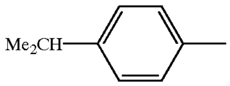 | 295–297 |
| 23-121 | —$NHCO(CH_2)_2COOCH_2Me$ | 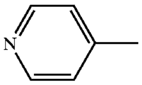 | 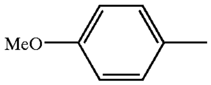 | 261–264 |
| 23-122 | —$NHCO(CH_2)_2COOH$ | 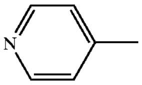 | 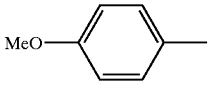 | 334–336 |
| 23-123 | —$NH_2$ | 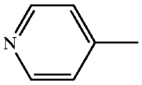 | 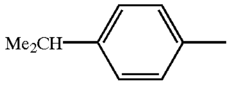 | 267–269 |
| 23-124 | —$NH_2$ | 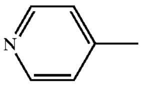 | 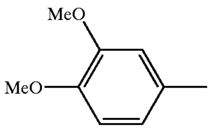 | 218–219 |
| 23-125 | —$NH_2$ | 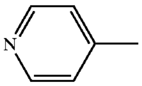 | 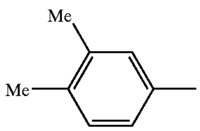 | 248–250 |
| 23-126 | —$NH_2$ | 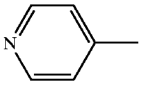 | 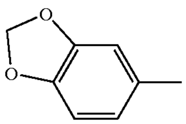 | 273–275 |

TABLE 15-continued
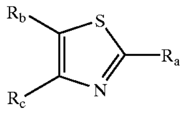
| Ref. Ex. Compd. | $R_a$ | $R_b$ | $R_c$ | mp/° C. |
|---|---|---|---|---|
| 23-127 | —NHCOMe | 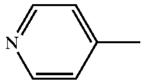 | 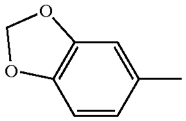 | 295–296 |
| 23-128 | —NHCOMe | 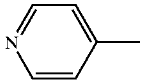 | 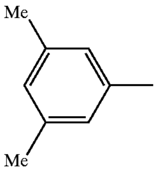 | 284–286 |
| 23-129 | —NHCOMe | 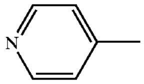 | 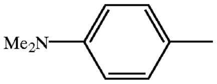 | 289–291 |
TABLE 16
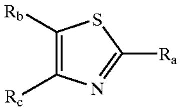
| Ref. Ex. Compd. | $R_a$ | $R_b$ | $R_c$ | Additive | mp/° C. |
|---|---|---|---|---|---|
| 23-130 | —$NHCOCHMe_2$ | 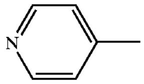 | 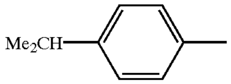 | | 284–285 |
| 23-131 | —$NHCOCMe_3$ | 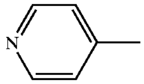 | 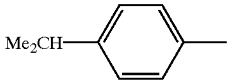 | | 293–295 |
| 23-132 | —$NHCONH(CH_2)_2Me$ | 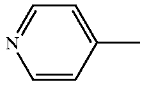 | 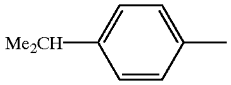 | | 287–288 |
| 23-133 | —$NH_2$ | 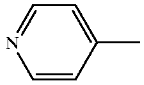 | 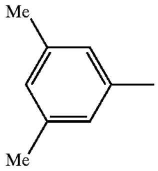 | | 242–244 |
| 23-134 | —$NH_2$ | 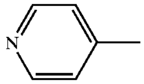 | 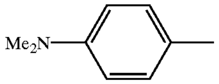 | | 309–311 |

TABLE 16-continued
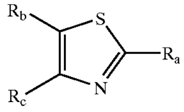
| Ref. Ex. Compd. | $R_a$ | $R_b$ | $R_c$ | Additive | mp/° C. |
|---|---|---|---|---|---|
| 23-135 | —$CH_2COOCH_2Me$ | 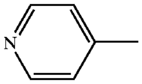 | 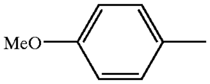 | HCl | 150–152 |
| 23-136 | 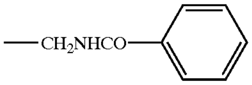 | 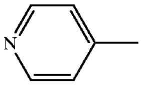 | 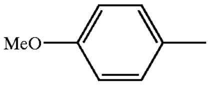 | | 150–151 |
| 23-137 | —NHCOMe | 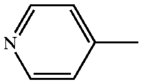 | 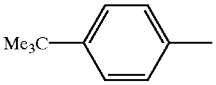 | | 280–281 |
| 23-138 | —$NHCOCHMe_2$ | 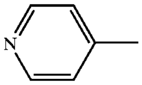 | 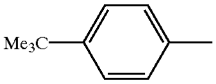 | | 303–304 |
| 23-139 | —$NHCOCMe_3$ | 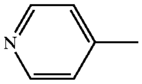 | 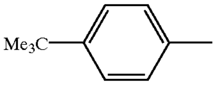 | | 317–319 |
| 23-140 | —NHCOMe | 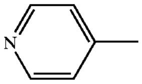 | 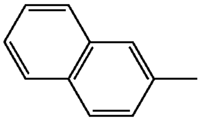 | | 342–345 |
| 23-141 | —$NHCOCHMe_2$ | 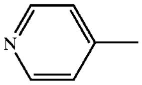 | 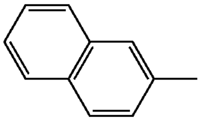 | | 297–298 |
| 23-142 | —$NHCOCMe_3$ | 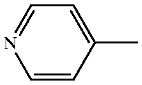 | 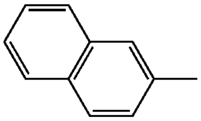 | | 313–315 |
| 23-143 | —$NH_2$ | 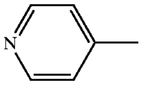 | 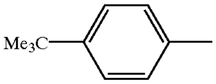 | | 254–257 |
| 23-144 | —$NH_2$ | 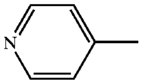 | 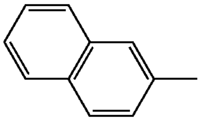 | | 261–264 |
| 23-145 | —$CH_2COOH$ | 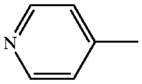 | 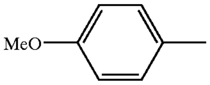 | | 135–137 |
| 23-146 | —$CH_2CONHMe$ | 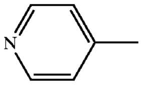 | 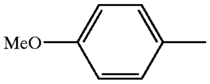 | | 129–130 |

TABLE 17
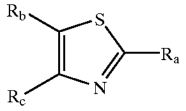
| Ref. Ex. Compd. | $R_a$ | $R_b$ | $R_c$ | mp/° C. |
|---|---|---|---|---|
| 23-147 | -Me | 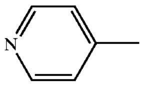 | 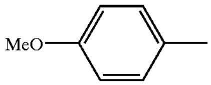 | 132–133 |
| 23-148 | —NHCOMe | 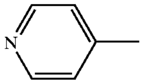 | 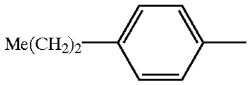 | 256–258 |
| 23-149 | —$NHCOCHMe_2$ | 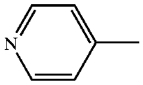 | 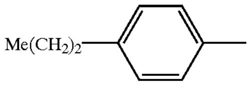 | 269–272 |
| 23-150 | 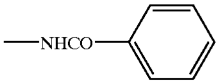 | 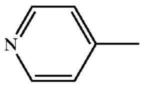 | 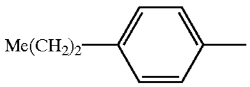 | 240–242 |
| 23-151 | —NHCOMe | 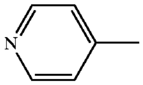 | 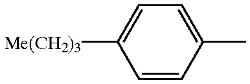 | 259–261 |
| 23-152 | —NHCOMe | 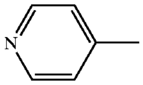 | 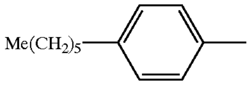 | 237–239 |
| 23-153 | —NHCOMe | 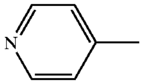 | 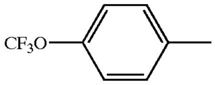 | 296–298 |
| 23-154 | —$NHCOCHMe_2$ | 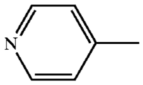 | 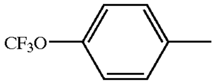 | 285–286 |
| 23-155 | —$NHCOCF_3$ | 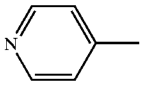 | 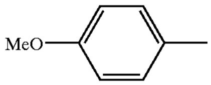 | 260–262 |
| 23-156 | —$NHCONHCH_2Me$ | 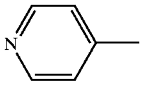 | 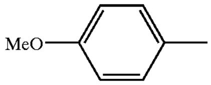 | 224–226 |
| 23-157 | —$NHCONHCH_2Me$ | 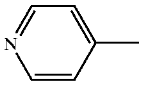 | 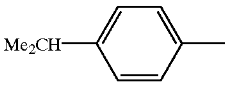 | 181–183 |
| 23-158 | —$NH_2$ | 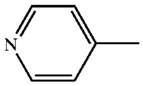 | 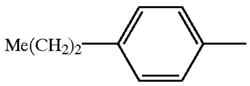 | 240–242 |
| 23-159 | —$NH_2$ | 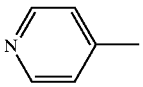 | 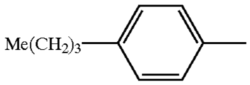 | 204–206 |

TABLE 17-continued
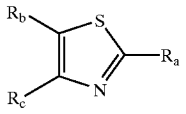
| Ref. Ex. Compd. | $R_a$ | $R_b$ | $R_c$ | mp/° C. |
|---|---|---|---|---|
| 23-160 | —$NH_2$ | 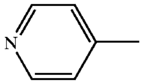 | 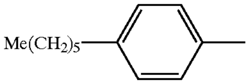 | 178–179 |
| 23-161 | —$NH_2$ | 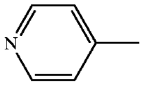 | 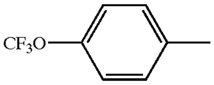 | 262–264 |
| 23-162 | —COOH | 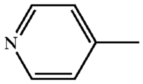 | 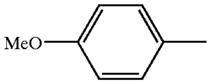 | 141–143 |
| 23-163 | —$NHCOCH_2Me$ | 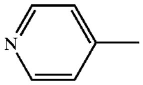 | 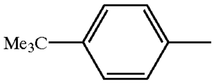 | 295–297 |
| 23-164 | 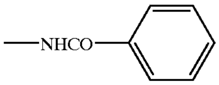 | 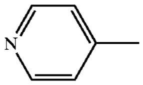 | 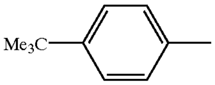 | 292–294 |
| 23-165 | 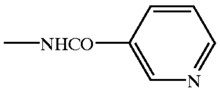 | 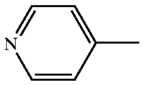 | 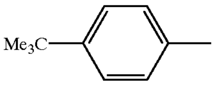 | 326–328 |
TABLE 18
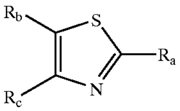
| Ref. Ex. Compd. | $R_a$ | $R_b$ | $R_c$ | mp/° C. |
|---|---|---|---|---|
| 23-166 | 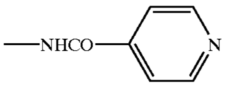 | 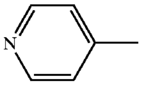 | 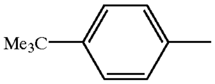 | 326–329 |
| 23-167 | 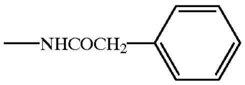 | 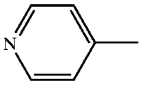 | 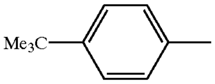 | 277–279 |
| 23-168 | 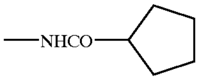 | 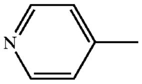 | 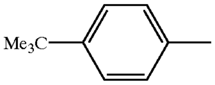 | 309–311 |
| 23-169 | —$NHCONHCH_2Me$ | 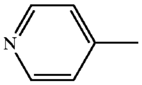 | 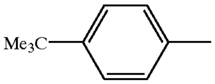 | 289–292 |

TABLE 18-continued
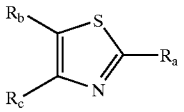
| Ref. Ex. Compd. | $R_a$ | $R_b$ | $R_c$ | mp/° C. |
|---|---|---|---|---|
| 23-170 | —NHCONH$(CH_2)_2$Me | 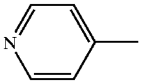 | 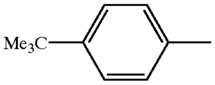 | 212–214 |
| 23-171 | —NHCOCH$_2$OMe | 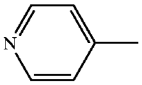 | 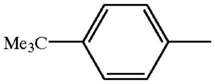 | 248–249 |
| 23-172 | —NHCOMe | 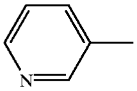 | 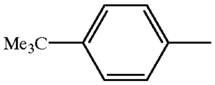 | 228–230 |
| 23-173 | —NHCOCH$_2$Me | 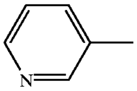 | 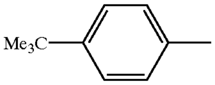 | 244–246 |
| 23-174 | —NHCOCHMe$_2$ | 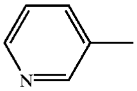 | 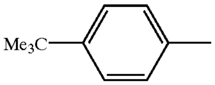 | 228–229 |
| 23-175 | 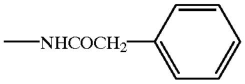 | 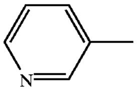 | 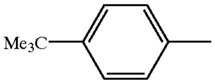 | 204–206 |
| 23-176 | 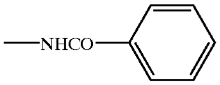 | 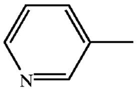 | 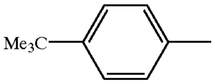 | 216–218 |
| 23-177 | 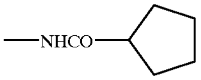 | 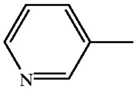 | 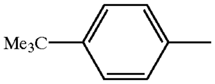 | 218–220 |
| 23-178 | 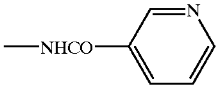 | 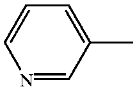 | 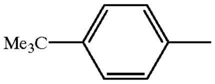 | 251–253 |
| 23-179 | 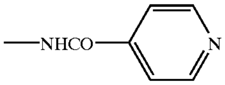 | 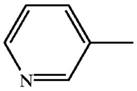 | 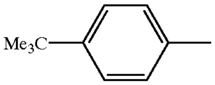 | 271–273 |
| 23-180 | —NHCONHCH$_2$Me | 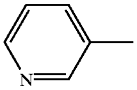 | 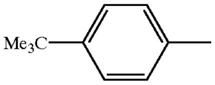 | 302–305 |
| 23-181 | —NHCONH$(CH_2)_2$Me | 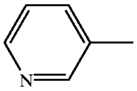 | 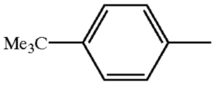 | 190–192 |
| 23-182 | —NH$_2$ | 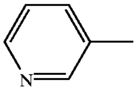 | 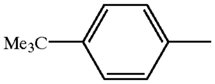 | 239–241 |

TABLE 18-continued
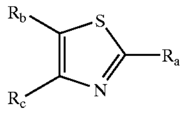
| Ref. Ex. Compd. | $R_a$ | $R_b$ | $R_c$ | mp/° C. |
|---|---|---|---|---|
| 23-183 | —$NH_2$ | 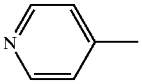 | 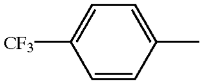 | 304–306 |
TABLE 19
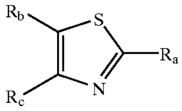
| Ref. Ex. Compd. | $R_a$ | $R_b$ | $R_c$ | mp/° C. |
|---|---|---|---|---|
| 23-184 | —NHCOMe | 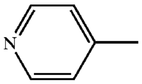 | 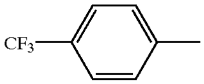 | 328–330 |
| 23-185 | —$NHCOCH_2Me$ | 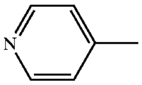 | 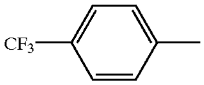 | 284–286 |
| 23-186 | —$NHCOCHMe_2$ | 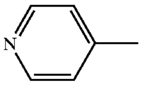 | 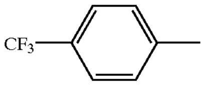 | 274–275 |
| 23-187 | 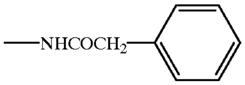 | 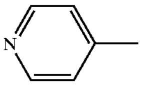 | 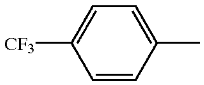 | 295–296 |
| 23-188 | 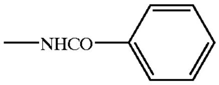 | 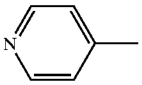 | 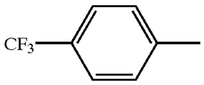 | 254–255 |
| 23-189 | 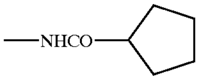 | 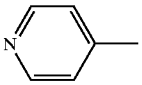 | 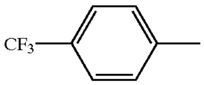 | 272–273 |
| 23-190 | 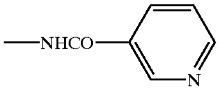 | 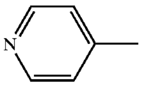 | 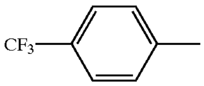 | 262–264 |
| 23-191 | 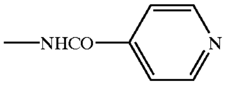 | 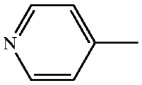 | 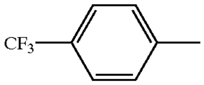 | 263–264 |
| 23-192 | —$NHCONHCH_2Me$ | 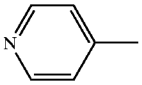 | 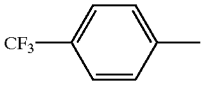 | 206–207 |

TABLE 19-continued
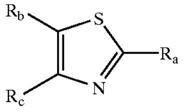
| Ref. Ex. Compd. | $R_a$ | $R_b$ | $R_c$ | mp/° C. |
|---|---|---|---|---|
| 23-193 | —NHCONH$(CH_2)_2$Me | 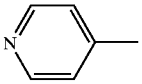 | 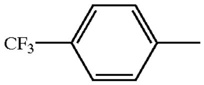 | 208–210 |
| 23-194 | —NHCO$CH_2$Me | 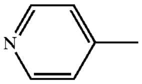 | 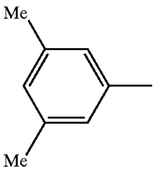 | 291–293 |
| 23-195 | —NHCOCH$Me_2$ | 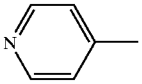 | 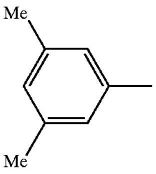 | 270–272 |
| 23-196 | 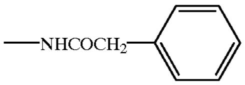 | 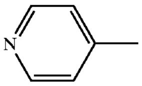 | 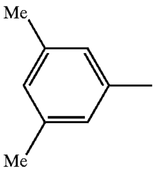 | 226–229 |
| 23-197 | 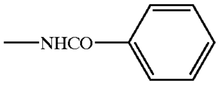 | 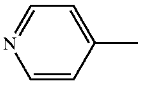 | 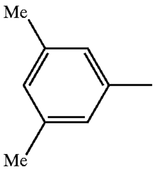 | 285–286 |
| 23-198 | 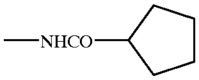 | 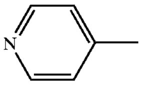 | 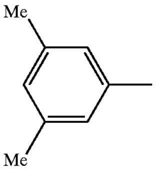 | 275–278 |

TABLE 20
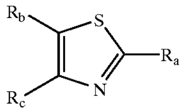
| Ref. Ex. Compd. | $R_a$ | $R_b$ | $R_c$ | mp/° C. |
|---|---|---|---|---|
| 23-199 | 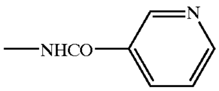 | 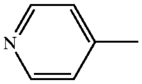 | 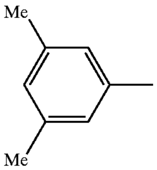 | 267–270 |
| 23-200 | 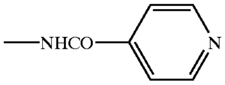 | 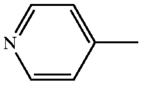 | 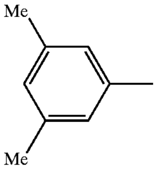 | 302–304 |
| 23-201 | —NHCONHCH$_2$Me | 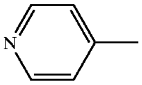 | 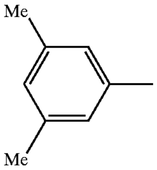 | 202–203 |
| 23-202 | —NHCONH(CH$_2$)$_2$Me | 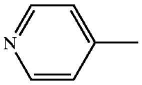 | 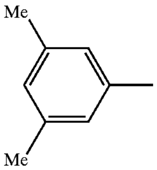 | 128–130 |
| 23-203 | —NHCOCH$_2$OMe | 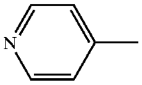 | 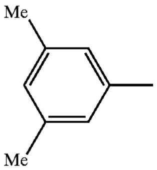 | 220–222 |
| 23-204 | —NH$_2$ | 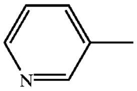 | 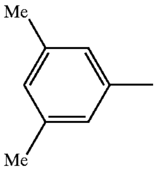 | 237–240 |
| 23-205 | —NHCOMe | 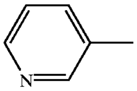 | 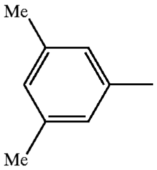 | 288–289 |

TABLE 20-continued
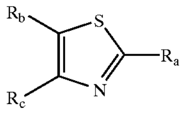
| Ref. Ex. Compd. | $R_a$ | $R_b$ | $R_c$ | mp/° C. |
|---|---|---|---|---|
| 23-206 | —NHCOCH$_2$Me | 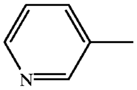 | 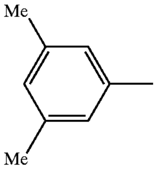 | 292–293 |
| 23-207 | —NHCOCHMe$_2$ | 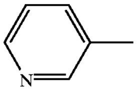 | 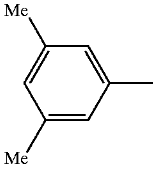 | 253–254 |
| 23-208 | 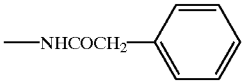 | 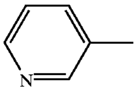 | 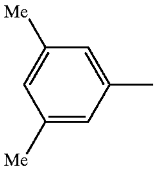 | 235–238 |
TABLE 21
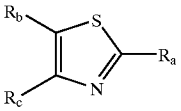
| Ref. Ex. Compd. | $R_a$ | $R_b$ | $R_c$ | Additive | mp/° C. |
|---|---|---|---|---|---|
| 23-209 | 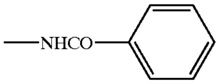 | 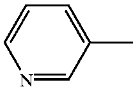 | 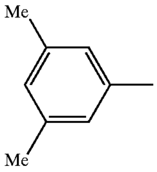 | | 300–301 |
| 23-210 | 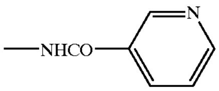 | 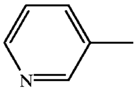 | 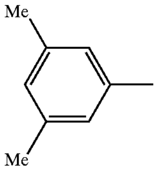 | | 277–278 |
| 23-211 | 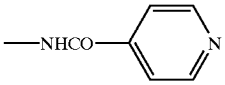 | 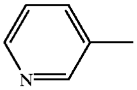 | 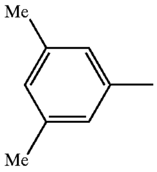 | | 278–280 |

TABLE 21-continued
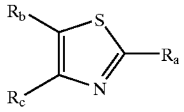
| Ref. Ex. Compd. | $R_a$ | $R_b$ | $R_c$ | Additive | mp/° C. |
|---|---|---|---|---|---|
| 23-212 | —$NHCONHCH_2Me$ | 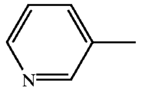 | 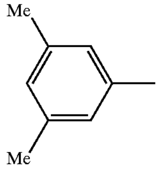 | | 220–224 |
| 23-213 | —$NHCONH(CH_2)_2Me$ | 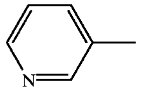 | 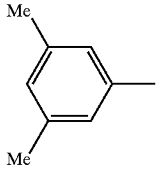 | | 204–206 |
| 23-214 | —$COOCH_2Me$ | 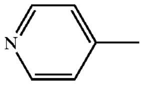 | 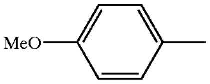 | | 149–150 |
| 23-215 | —$NHCOCH_2NMe_2$ | 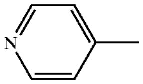 | 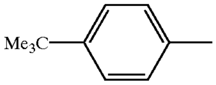 | | 230–231 |
| 23-216 | —$NH_2$ | 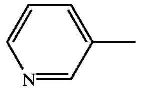 | 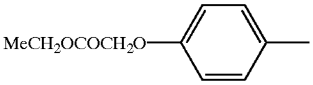 | | 167–169 |
| 23-217 | —NHCOMe | 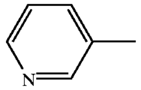 | 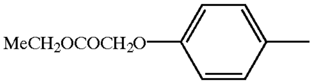 | | 195–197 |
| 23-218 | —NHCOMe | 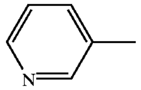 | 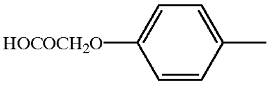 | | 266–270 |
| 23-219 | —$NH_2$ | 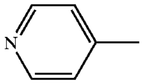 | 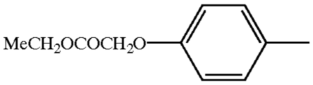 | | 181–185 |
| 23-220 | —NHCOMe | 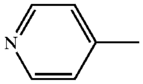 | 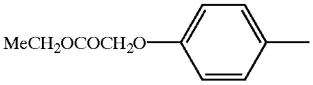 | | 239–244 |
| 23-221 | —NHCOMe | 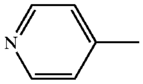 | 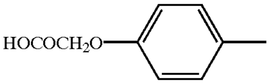 | HCl | 237–242 |
| 23-222 | 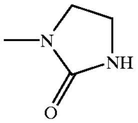 | 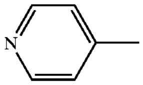 | 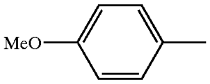 | | 248–250 |

EXAMPLE 1

N-Methyl[5-phenyl-4-(3-pyridyl)-1,3-thiazol-2-yl]amine

To a solution of N-methylthiourea (484 mg) in acetonitrile (40 mL), was added 2-bromo-2-phenyl-1-(3-pyridyl)ethanone hydrobromide (2.0 g), and then triethylamine (0.8 mL) was added dropwise to the mixture with stirring. After addition, the resulting mixture was stirred at reflux for 3 h and the solvent was evaporated. An aqueous saturated solution of sodium hydrogen carbonate was added to the residue and extracted with ethyl acetate. The extracts were washed with water, dried and the solvent was evaporated. The crystalline residue was recrystallized from ethyl acetate-isopropyl ether to give the title compound (1.2 g, yield 80%).

mp 144–145° C.

EXAMPLE 2

[5-Phenyl-4-(3-pyridyl)-1,3-thiazol-2-yl]amine

To a mixture of 2-bromo-2-phenyl-1-(3-pyridyl)ethanone hydrobromide (2.00 g) and thiourea (432 mg) in acetonitrile (30 mL), was added triethylamine (0.80 mL) dropwise and the resulting mixture was stirred at 80° C. for 3 h. The solvent was removed under reduced pressure and an aqueous saturated solution of sodium hydrogen carbonate was added to the residue. The mixture was extracted with ethyl acetate.

The organic phases were washed with water, dried and concentrated under reduced pressure to give the amorphous title compound (1.10 g, yield 84%).

$^1$H-NMR ($CDCl_3$) δ: 5.31 (2H, br s), 7. 13–7.29 (6H, m), 7.76 (1H, dt, J=7.8, 1.8 Hz), 8.46 (1H, dd, J=5.0, 1.8 Hz), 8.70 (1H, d, J=1.8 Hz).

EXAMPLE 3

N-[5-Phenyl-4-(3-pyridyl)-1,3-thiazol-2-yl]acetamide

To a solution of [5-phenyl-4-(3-pyridyl)-1,3-thiazol-2-yl]amine (1.10 g, 4.34 mmol) in N,N-dimethylacetamide (20 mL) was added acetyl chloride (680 mg, 8.68 mmol) and stirred at 80° C. for 3 h. Water was added to the reaction mixture and extracted with ethyl acetate twice. The combined organic phases were washed with water, dried over magnesium sulfate, filtered and concentrated under reduced pressure. The residue was recrystallized from chloroform-ethyl ether to give the title compound (750 mg, yield 59%).

mp 264–267° C.

EXAMPLE 4

Using 2-bromo-2-[4-(1,1-dimethylethyl)phenyl]-1-(4-pyridyl)ethanone hydrobromide and 2-bromo-2-(3,5-dimethylphenyl)-1-(4-pyridyl)ethanone hydrobromide instead of using 2-bromo-2-phenyl-1-(3-pyridyl)ethanone hydrobromide, the below Example Compounds 4-1 and 4-2 were obtained in the same manner as described in above Example 2.

Example Compound 4-1:

[5-[4-(1,1-dimethylethyl)phenyl]-4-(4-pyridyl)-1,3-thiazol-2-yl]amine mp 275–277° C.

Example Compound 4-2:

[5-(3,5-dimethylphenyl)-4-(4-pyridyl)-1,3-thiazol-2-yl]amine mp 262–263° C.

EXAMPLE 5

Using [5-[4-(1,1-dimethylethyl)phenyl]-4-(4-pyridyl)-1,3-thiazol-2-yl]amine and [5-(3,5-dimethylphenyl)-4-(4-pyridyl)-1,3-thiazol-2-yl]amine instead of using [5-phenyl-4-(3-pyridyl)-1,3-thiazol-2-yl]amine, the below Example Compounds 5-1 and 5-2 were obtained in the same manner as described in above Example 3.

Example Compound 5-1:

N-[5-[4-(1,1-dimethylethyl)phenyl]-4-(4-pyridyl)-1,3-thiazol-2-yl]acetamide mp 245–246° C.

Example Compound 5-2:

N-[5-(3,5-dimethylphenyl)-4-(4-pyridyl)-1,3-thiazol-2-yl]acetamide mp 304–308° C.

EXAMPLE 6

2-Ethyl-5-phenyl-4-(3-pyridyl)-1,3-thiazole

Using propanethioamide instead of using N-methylthiourea, the title compound was obtained in the same manner as described in the above Example 1.

mp 144–145° C.

EXAMPLE 7

4-[5-Phenyl-4-(3-pyridyl)-1,3-thiazol-2-yl]butyric acid

A solution of methyl 4-[5-phenyl-4-(3-pyridyl)-1,3-thiazol-2-yl]butyrate (4.1 g), which was obtained in the same manner as described in the above Example 1 using 4-(methoxycarbonyl)butanethioamide instead of using N-methylthiourea, in methanol (15 mL) was added to an 8N aqueous sodium hydroxide solution (20 mL) and stirred at 80° C. for 2 h. The mixture was adjusted to pH 6.0 with 2N hydrochloric acid and the product was extracted with ethyl acetate. The extract was washed with water, dried and the solvent was evaporated. The residue was recrystallized from ethyl acetate to afford the title compound (3.4 g, yield 87%).

mp 141–142° C.

EXAMPLE 8

4-[2-Acetylamino-4-(3,5-dimethylphenyl)-1,3-thiazol-5-yl]pyridine 1-Oxide

To a suspension of N-[4-(3,5-dimethylphenyl)-5-(4-pyridyl)-1,3-thiazol-2-yl]acetamide (1.0 g) in chloroform (30 mL), was added 70% m-chloroperbenzoic acid (0.80 g), and the mixture was stirred at room temperature for 1 h. The solvent was removed under reduced pressure, and the residue was treated with an aqueous saturated solution of sodium hydrogen carbonate. The formed crystalline residue was washed with water, dried and recrystallized from ethanol to obtain the title compound (0.55 g, yield 53%).

mp 332–334° C.

The chemical structures obtained in Examples 1 to 8 are shown in Table 22.

TABLE 22
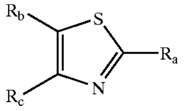
| Ex. Compd. | $R_a$ | $R_b$ | $R_c$ |
|---|---|---|---|
| 1 | —NHMe | 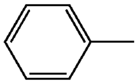 | 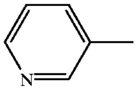 |
| 2 | —$NH_2$ | 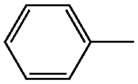 | 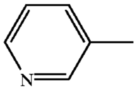 |
| 3 | —NHCOMe | 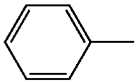 | 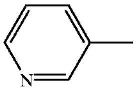 |
| 4-1 | —$NH_2$ | 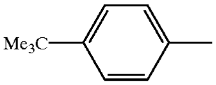 | 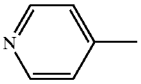 |
| 4-2 | —$NH_2$ | 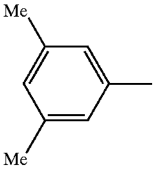 | 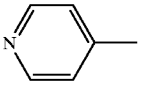 |
| 5-1 | —NHCOMe | 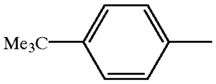 | 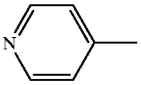 |
| 5-2 | —NHCOMe | 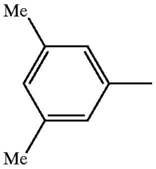 | 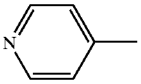 |
| 6 | —$CH_2Me$ | 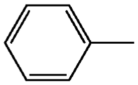 | 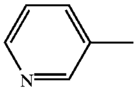 |
| 7 | —$(CH_2)_3COOH$ | 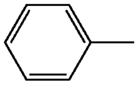 | 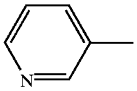 |
| 8 | —NHCOMe | 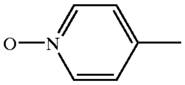 | 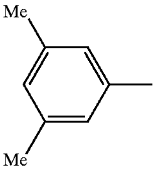 |

| | |
|---|---|
| (1) Reference: Example Compound 13–89 | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Calcium carboxymethyl cellulose | 20 mg |
| Total | 120 mg |

(1) to (6) were mixed in an ordinary manner, and tabletted into tablets using a tabletting machine.

EXPERIMENTAL EXAMPLE 1

The following procedures in this Example were carried out according to the methods described in Molecular Cloning—Cold Spring Harbor Laboratory (1989) or protocol specified by manufacturers.

(1) Cloning of Human Adenosine $A_3$ Receptor

Cloning of the human adenosine $A_3$ receptor gene was carried out by the polymerase chain reaction (PCR) from human brain cDNA. Using 1 ng of brain cDNA (Quick-Clone cDNA, TOYOBO, Osaka) as template, PCR was performed in DNA Thermal Cycler 480 (Perkin Elmer, Foster, Calif.) (reaction conditions: 35 cycles of 1 min at 95° C., 1 min at 66° C., and 2 min at 75° C.) by mixing primers (50 pmol each), 5'-CGCCTCTAGACAAGATGCCCAACAACAGCACTGC-3' [Sequence No. 1] and 5'-CGGGGTCGACACTACTCAGAATTCTTCTCAATGC-3' [Sequence No. 2], which were designed referring to nucleotide sequence of adenosine $A_3$ receptor gene reported by Salvatore et. al., (Proc. Natl. Acad. Sci. U.S.A., 90:10365–10369, 1993) and TaKaRa LA PCR Kit Ver.2 (TaKaRa Shuzo Co. Ltd., Kyoto) in a Thermal cycler 480 (Parkin Elmer). The PCR product was electrophoresed and 1.0 kb DNA fragment was recovered. The DNA fragment encoding adenosine $A_3$ receptor was cloned using Original TA Cloning Kit (FUNAKOSHI, Tokyo).

Thus obtained plasmid was digested with Xba I (TaKaRa Shuzo Co. Ltd., Kyoto), blunted with T4 DNA polymerase (TaKaRa Shuzo Co. Ltd., Kyoto) and digested with Sal I (TaKaRa Shuzo Co. Ltd., Kyoto) to obtain adenosine $A_3$ receptor gene fragment.

(2) Construction of Human Adenosine $A_3$ Receptor Expression Plasmid

The SRα promoter from pTB1411 disclosed in JP-A-5-076385 was ligated into the pCI vector (Promega, Tokyo). which was digested with Bgl II (TaKaRa Shuzo Co. Ltd., Kyoto), blunted and digested with EcoRI (TaKaRa Shuzo Co. Ltd., Kyoto) subsequently. The resulting plasmid, designated as pCI-SRα, was then digested with Cla I (TaKaRa Shuzo Co. Ltd., Kyoto) and blunted with T4 DNA polymerase (TaKaRa Shuzo Co. Ltd., Kyoto). On the other hand, pGFP-C1 (TOYOBO, Osaka) was digested with Bsu 36I (DAIICHIKAGAKUYAKUHIN, Tokyo) and the 1.63 kb fragment was recovered after the blunting with T4 DNA polymerase to ligate to the pCI-SRα vector using DNA Ligation kit (TaKaRa Shuzo Co. Ltd., Kyoto). The ligation mixture was used to transform *E.coli* JM109 competent cells (TaKaRa Shuzo Co. Ltd., Kyoto). The resulting plasmid thus obtained was designated as pMSRαneo.

pMSRαneo was digested with EcoRI (TaKaRa Shuzo Co. Ltd., Kyoto), blunted with T4 DNA polymerase (TaKaRa Shuzo Co. Ltd., Kyoto) and then digested with Sal I (TaKaRa Shuzo Co. Ltd., Kyoto). After the reaction mixture was fractionated on agarose gel, the DNA at size of 5.4 kb was ligated with adenosine $A_3$ receptor obtained in the above (1) by using DNA Ligation kit (TaKaRa Shuzo Co. Ltd., Kyoto). The ligation mixture was used to transform *E.coli* JM109 competent cells (TaKaRa Shuzo Co. Ltd., Kyoto). The plasmid thus obtained was designated as pA3SRα.

(3) Transfection of Adenosine $A_3$ Receptor Expression Plasmid into CHO ($dhfr^-$) and the Expression CHO ($dhfr^-$) cells were grown on Ham's F-12 medium (Nihon Selyaku, Tokyo) supplement with 10% fetal bovine serum (Life Tech Oriental; Life Technologies, Inc., Rockville, Md., USA) in a 750 ml Tissue culture flask (Becton Dickinson, Mt. View, Calif.). The growing cells were treated with 0.5 g/l trypsin-0.2 g/l EDTA (Life Technologies, Inc., Rockville, Md., USA) to harvest, washed with PBS (Life Technologies, Inc., Rockville, Md., USA), centrifugated at 1000 rpm for 5 min, and suspended in PBS. Transfection with pA3SRα into the cell was performed by electroporation using a Bio-Rad/Gene Pulser (Bio-Rad, Tokyo) at 0.25 V/960 μF ($8\times10^6$ cells/10 μg DNA/0.4 cm electrode gap cuvette). The transfected cells were transferred into Ham's F-12 medium containing 10% fetal bovine serum, cultivated for 24 hours, harvested, suspended in Ham's F-12 media supplement with 10% fetal bovine serum and 500 μg/ml geneticin (Life Technologies Inc., Rockville, Md., USA) at a cell density of $10^4$ cells/ml. The cells were plated onto 96 well plates (Becton Dickinson, Mt. View, Calif.) containing Ham's F-12 media supplement with 10% fetal bovine serum and 500 μg/ml geneticin (Life Technologies Inc., Rockville, Md., USA) at a cell density of $10^4$ cells/ml. The geneticin resistant cells thus obtained were further cultivated on 24 well plates (Becton Dickinson, Mt. View, Calif.) and the cells expressing adenosine $A_3$ receptor were selected from them as follows. The cells were incubated in assay buffer I (HBSS (Wako chemicals, Osaka) containing 0.1% BSA, 0.25 mM PMSF, 1 μg/ml pepstatin, and 20 μg/ml leupeptin) to which was added 50 pM $^{125}$I-AB-MECA (Amersham) as ligand, for 1 hour, and washed with assay buffer I. The radioactivity associated with the:.cell was measured in a γ-counter to select A3AR/CHO cells which specifically bind to the ligand.

(4) Cell Membrane Preparation of the Transfectant Expressing Adenosine $A_3$ Receptor After A3AR/CHO cells obtained in the above (3) were cultivated in Ham's F-12 medium containing 10% fetal bovine serum for 2 days, the cells were treated with PBS plus 0.02% EDTA, centrifuged to collect, resuspended in assay buffer II (50 mM Tris-HCl (pH7.5), 1 mM EDTA, 10 mM $MgCl_2$, 0.25 mM PMSF, 1 μg/ml pepstatin, and 20 μg/ml leupeptin) and homogenized using Polytron homogenizer (PT-3000, KINEMATICA AG: 20,000 rpm, 20 sec, 3 times). This suspension was centrifuged at 2,000 rpm for 10 min and supernatant fraction containing cell membranes was obtained. The supernatant fraction was ultra-centrifuged at 30,000 rpm (model L8-70M, rotor 70Ti, Beckman) for 1 hour. Thus obtained pellet was resuspended in assay buffer II containing 2 unit/ml adenosine deaminase (Boehriger Mannheim, Tokyo) and incubated at 30° C. for 30 min. The suspension was ultra-centrifuged under the same condition as above and the cell membrane fraction was obtained as the pellet.

(5) Binding Assays with Adenosine $A_3$ Receptor 10 nM of [$^3$H]-NECA (Amersham Life Sciences, Inc., Tokyo) as ligand was added to the reaction mixture including test compound at various concentration and 100 μg/ml of membranes obtained in (4) in assay buffer II. The reaction mixture was incubated for 1 hour at room temperature and filtrated through the Unifilter GF/C (Packard Instrument Company, Tokyo) to transfer the membrane onto the filter, using Cell Harvester (Packard Instrument Company, Tokyo). The filter was washed three times with ice-cold 50 mM Tris-HCl (pH 7.5), and dried. Then, Microscint-0 was placed on the filter and radioactivity retained on the filter was determined by Top-Count (Packard Instrument Company, Tokyo). Curve-fit and the concentration that inhibits 50% specific binding ($IC_{50}$) to the membrane of [$^3$H]-NECA were calculated by program Prizm 2.01 (Graph Pad Software, San Diego).

TABLE 23

| Reference Compound No. | $IC_{50}$ (nM) |
|---|---|
| 10 | 0.27 |
| 13–89 | 0.55 |
| 13–92 | 0.70 |

This result shows that the compound (I) has a high affinity for adenosine $A_3$ receptor.

INDUSTRIAL APPLICABILITY

Since compound (I) containing compounds (Ia), (Ib) and (Ic) has a potent $A_3$ adenosine receptor antagonistic activity and low toxicity, it is useful as $A_3$ adenosine receptor antagonist and can be used as a prophylactic and therapeutic agent for asthma, allergosis, inflammation, Addison's diseases, autoallergic hemolytic anemia, Crohn's diseases, psoriasis, rheumatism, diabetes and so on.

What is claimed is:

1. A method for preventing and/or treating asthma, allergosis or inflammation in a mammal in need thereof, which comprises administering to said mammal an effective asthma, allergosis or inflammation treating amount of a compound of the formula:

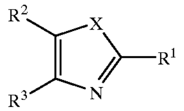

wherein $R^1$ represents (i) a hydrogen atom, (ii) a $C_{1-8}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents, (iii) a 5- to 14-membered heterocyclic group containing 1 to 4 hetero atoms selected from the group consisting of nitrogen, sulfur and oxygen atoms in addition to carbon atoms, which group may be substituted by 1 to 5 substituents, (iv) an amino which may be substituted by 1 or 2 substituents selected from the group consisting of (a) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents (b) a $C_{1-6}$ alkylidene group which may be substituted by 1 to 5 substituents, (c) a 5- to 14-membered heterocyclic group containing 1 to 4 hetero atoms selected from the group consisting of nitrogen, sulfur and oxygen atoms in addition to carbon atoms, which group may be substituted by 1 to 5 substituents, and (d) an acyl of the formula: —(C═O)—$R^5$, —(C═O)—O$R^5$, —(C═O)—N$R^5R^6$, —(C═S)—NH$R^5$ or —$SO_2$—$R^7$ wherein $R^5$ is (i') a hydrogen atom, (ii') a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents or (iii') a 5- to 14-membered heterocyclic group containing 1 to 4 hetero atoms selected from the group consisting of nitrogen, sulfur and oxygen atoms in addition to carbon atoms, which group may be substituted by 1 to 5 substituents; $R^6$ is a hydrogen atom or $C_{1-6}$ alkyl; and $R^7$ is (i') a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents or (ii') a 5- to 14-membered heterocyclic group containing 1 to 4 hetero atoms selected from the group consisting of nitrogen, sulfur and oxygen atoms in addition to carbon atoms, which group may be substituted by 1 to 5 substituents, (v) a 5–7-membered non-aromatic cyclic amino optionally containing 1 to 4 hetero atoms selected from the group consisting of nitrogen, sulfur and oxygen atoms in addition to carbon atoms and at least one nitrogen atom, which may be substituted by 1 to 3 substituents selected from the group consisting of $C_{1-6}$ alkyl, $C_{6-14}$ aryl or $C_{1-6}$ alkyl-carbonyl, 5- to 10-membered heterocyclic group and oxo, or (vi) an acyl of the formula: —(C═O)—$R^5$, —(C═O)—$OR^5$, —(C═O)—$NR^5R^6$, —(C═S)—$NHR^5$ or —$SO_2$—$R^7$ wherein each symbol is as defined above;

$R^2$ is a pyridyl which may be substituted by 1 to 5 substituents; and $R^3$is (i) a pyridyl which may be substituted by 1 to 5 substituents or (ii) a $C_{6-14}$ aryl which may be substituted by 1 to 5 substituents in which a substituent can form, together with a neighboring substituent, a 4–7-membered non-aromatic carbocyclic ring;

wherein the above "substituents" are selected from the group consisting of (1) halogen atoms, (2) $C_{1-3}$ alkylenedioxy, (3) nitro, (4) cyano, (5) optionally halogenated $C_{1-6}$ alkyl, (6) optionally halogenated $C_{2-6}$ alkenyl, (7) carboxy $C_{2-6}$ alkenyl, (8) optionally halogenated $C_{2-6}$ alkynyl, (9) optionally halogenated $C_{3-6}$ cycloalkyl, (10) $C_{6-14}$ aryl, (11) optionally halogenated $C_{1-8}$ alkoxy, (12) $C_{1-6}$ alkoxy-carbonyl-$C_{1-6}$ alkoxy, (13) hydroxy, (14) $C_{6-14}$ aryloxy, (15) $C_{7-16}$ aralkyloxy, (16) mercapto, (17) optionally halogenated $C_{1-6}$ alkylthio, (18) $C_{6-14}$ arylthio, (19) $C_{7-16}$ aralkylthio, (20) amino, (21) mono-$C_{1-6}$ alkylamino, (22) mono-$C_{6-14}$ arylamino, (23) di-$C_{1-6}$ alkylamino, (24) di-$C_{6-14}$ arylamino, (25) formyl, (26) carboxy, (27) $C_{1-6}$ alkyl-carbonyl, (28) $C_{3-6}$ cycloalkyl-carbonyl, (29) $C_{1-6}$ alkoxy-carbonyl, (30) $C_{6-14}$ aryl-carbonyl, (31) $C_{7-16}$ aralkyl-carbonyl, (32) $C_{6-14}$ carbonyl, (33) $C_{7-16}$ aralkyloxy-carbonyl, (34) 5- or 6-membered heterocycle carbonyl, (35) carbamoyl, (36) mono-$C_{1-6}$ alkyl-carbamoyl, (37) di-$C_{1-6}$ alkyl-carbamoyl, (38) $C_{6-14}$ aryl-carbamoyl, (39) 5- or 6-membered heterocycle carbamoyl, (40) $C_{1-6}$ alkylsulfonyl, (41) $C_{6-14}$ arylsulfonyl, (42) formylamino, (43) $C_{1-6}$ alkyl-carbonylamino, (44) $C_{6-14}$ aryl-carbonylamino, (45) $C_{1-6}$ alkoxy-carbonylamino, (46) $C_{1-6}$ alkylsulfonylamino, (47) $C_{6-14}$ arylsulfonylamino, (48) $C_{1-6}$ alkylcarbonyloxy, (49) $C_{6-14}$ aryl-carbonyloxy, (50) $C_{1-6}$ alkoxy-carbonyloxy, (51) mono-$C_{1-6}$ alkyl-carbamoyloxy, (52) di-$C_{1-6}$ alkyl-carbamoyloxy, (53) $C_{6-14}$ aryl-carbamoyloxy, (54) nicotinoyloxy, (55) 5- to 7-membered saturated cyclic amino which may be substituted by 1 to 3 substituents selected from the group consisting of $C_{1-6}$ alkyl, $C_{6-14}$ aryl, $C_{1-6}$ alkyl-carbonyl, 5- to 10-membered aromatic heterocyclic group and oxo, (56) 5- to 10-membered aromatic heterocyclic group and (57) sulfo;

X represents a sulfur atom;

or a pharmaceutically acceptable salt thereof, which may be N-oxidized, with a pharmaceutically acceptable excipient, carrier or diluent.

2. A method of claim 1, wherein $R^1$ is an amino which may be substituted.

3. A method of claim 1, wherein $R^1$ is an amino which may be substituted by 1 or 2 acyl of the formula: —(C═O)—$R^5$, —(C═O)—$OR^5$, —(C═O)—$NR^5R^6$, —(C═S)—$NHR^5$ or —$SO_2$—$R^7$.

4. A method of claim 1, wherein $R^1$ is an amino which may be substituted by 1 or 2 acyl of the formula: —(C═O)—$R^5$ or —(C═O)—$NR^5R^6$.

5. A method of claim 1, wherein $R^1$ is an amino which may be substituted by 1 or 2 acyl of the formula: —(C═O)—$R^5$ or —(C═O)—$NR^5R^6$;

$R^2$ is a pyridyl which may be substituted by 1 to 5 $C_{1-6}$ alkyl; and $R^3$ is a $C_{6-14}$ aryl which may be substituted by 1 to 5 substituents selected from the group consisting of halogen atoms, optionally halogenated $C_{1-6}$ alkoxy and carboxy.

6. A method of claim 1, wherein $R^1$ is (i) a $C_{1-8}$ alkyl, $C_{3-6}$ cycloalkyl or $C_{6-10}$ aryl group which may be substituted by 1 to 5 substituents selected from the group consisting of halogen atoms, optionally halogenated $C_{1-6}$ alkyl, carboxy $C_{2-6}$ alkenyl, optionally halogenated $C_{1-6}$ alkoxy, $C_{1-6}$ alkoxy-carbonyl-$C_{1-6}$ alkoxy, hydroxy, hydroxy, amino, mono-$C_{1-6}$alkylamino, carboxy, $C_{1-6}$ alkoxy-carbonyl, mono-$C_{1-6}$ alkyl-carbamoyl and $C_{6-14}$ aryl-carbonylamino, (ii) a 5-membered heterocyclic group, (iii) an amino which may be substituted by 1 or 2 substituents selected from the group consisting of (1) $C_{1-6}$ alkyl, (2) $C_{6-14}$ aryl, (3) $C_{7-16}$ aralkyl, (4) 6-membered group, (5) a $C_{1-6}$ alkyl-carbonyl, $C_{3-6}$ cycloalkyl-carbonyl, $C_{6-14}$ aryl-carbonyl, $C_{7-16}$ aralkyl-carbonyl, $C_{1-6}$ alkyl-carbamoyl or 5–6-membered heterocycle carbonyl group which may be substituted by 1 to 3 substituents selected from the group consisting of halogen atoms, $C_{1-6}$ alkyl, $C_{1-6}$ alkoxy, carboxy and $C_{1-6}$ alkoxy-carbonyl, and (6) di-$C_{1-6}$ alkylamino-$C_{1-6}$ alkylidene, (iv) a 5- or 6-membered non-aromatic cyclic amino which may be substituted by $C_{1-6}$ alkyl-carbonyl or oxo, or (v) carboxy;

$R^2$ is a pyridyl which may be substituted by 1 to 3 $C_{1-6}$ alkyl; and $R^3$ is a $C_{6-10}$ aryl which may be substituted by 1 to 3 substituents selected from the group consisting of halogen atoms, $C_{1-3}$ alkylenedioxy, optionally halogenated $C_{1-6}$ alkyl, carboxy $C_{2-6}$ alkenyl, optionally halogenated $C_{1-8}$ alkoxy, hydroxy, $C_{7-16}$ aralkyloxy and $C_{1-6}$ alkyl-carbonyloxy, in which the alkyl group can form, together with a neighboring alkyl group, a 5-membered non-aromatic carbocyclic ring.

7. A compound of the formula:

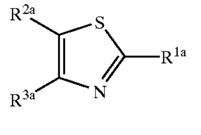

wherein $R^{1a}$ is an amino which may be substituted by 1 or 2 substituents selected from the group consisting of $C_{1-6}$ alkyl, $C_{1-6}$ alkyl-carbonyl, $C_{6-14}$ aryl-carbonyl and $C_{1-6}$ alkyl-carbamoyl;

$R^{2a}$ is a phenyl which may be substituted by 1 to 3 substituents selected from the group consisting of halogen atoms, optionally halogenated $C_{1-6}$ alkyl and optionally halogenated $C_{1-6}$ alkoxy; and $R^{3a}$ is a pyridyl, or a salt thereof.

8. A process for producing of a compound claim 7, which comprises reacting a compound of the formula:

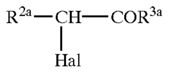

wherein Hal represents halogen atoms and other symbols are as defined in claim 7, or a salt thereof with a compound of the formula:

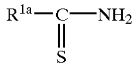

wherein $R^{1a}$ is as defined in claim 7, or a salt thereof, optionally in the presence of a base.

9. A pharmaceutical composition which comprises a compound of claim 7.

* * * * *

SEQUENCE LISTING

<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: primer DNA sequence based on adenosine A3 receptor gene sequence

<400> SEQUENCE: 1
cgcctctaga caagatgccc aacaacagca ctgc 34

<210> SEQ ID NO 2
<211> LENGTH: 34
<212> TYPE: DNA
<213> ORGANISM: Artificial Sequence
<220> FEATURE:
<223> OTHER INFORMATION: primer DNA sequence based on adenosine A3 receptor gene sequence

<400> SEQUENCE: 2
cggggtcgac actactcaga attcttctca atgc 34